US012595473B2

(12) United States Patent
Maubourguet et al.

(10) Patent No.: US 12,595,473 B2
(45) Date of Patent: Apr. 7, 2026

(54) GENETICALLY MODIFIED BACILLUS SUBTILIS STRAIN, OPTIMIZED VECTORS, AND USES THEREOF

(71) Applicant: ROQUETTE FRÈRES, Lestrem (FR)

(72) Inventors: Sébastien Maubourguet, Lompret (FR); Sophie Huchette, Betbune (FR); Claudia Borgmeier, Bensheim (DE); Guido Meurer, Seeheim-Jugenheim (DE)

(73) Assignee: ROQUETTE FRERES, Lestrem (FR)

( * ) Notice: Subject to any disclaimer, the term of this patent is extended or adjusted under 35 U.S.C. 154(b) by 27 days.

(21) Appl. No.: 18/613,291

(22) Filed: Mar. 22, 2024

(65) Prior Publication Data

US 2024/0301387 A1 Sep. 12, 2024

Related U.S. Application Data

(62) Division of application No. 16/762,030, filed as application No. PCT/EP2018/080328 on Nov. 6, 2018, now Pat. No. 12,012,624.

(30) Foreign Application Priority Data

Nov. 6, 2017 (EP) .................................... 17306533

(51) Int. Cl.
*C12N 9/90* (2006.01)

(52) U.S. Cl.
CPC .............. *C12N 9/90* (2013.01); *C12Y 501/03* (2013.01)

(58) Field of Classification Search
CPC ........ C12N 9/90; C12N 15/75; C12Y 501/03; C12Y 501/01001; C07K 14/32; C12P 19/02; C12P 19/24
See application file for complete search history.

(56) References Cited

U.S. PATENT DOCUMENTS

2007/0154988 A1 7/2007 Andersen et al.

FOREIGN PATENT DOCUMENTS

| | | | |
|---|---|---|---|
| CN | 104894047 | A | 9/2015 |
| CN | 105368767 | A | 3/2016 |
| CN | 106967659 | A | 7/2017 |
| WO | 2015/032761 | A1 | 3/2015 |
| WO | 2016/099388 | A1 | 6/2016 |

OTHER PUBLICATIONS

Mar. 14, 2019 International Search Report issued in International Patent Application No. PCT/EP2018/080328.

Mar. 14, 2019 Written Opinion issued in International Patent Application No. PCT/EP2018/080328.

Franziska Huff et al. "The Restriction Modification System of *Bacillus licheniformis* MS1 and Generation of a Readily Transformable Deletion Mutant". Applied Microbiology and Biotechnology, Springer, DE, vol. 101, No. 21, Sep. 23, 2017, pp. 7933-7944.

Stephanie Wemhoff et al. "Generation of Biologically Contained, Readily Transformable, and Genetically Manageable Mutants of the Biotechnologically Important *Bacillus pumilus*". Applied Microbiology and Biotechnology, Springer, DE, vol. 97, No. 17, May 5, 2013, pp. 7805-7819.

Yoann Le Breton et al. "In Vivo Random Mutagenesis of *Bacillus subtilis* by Use of TnYLB-1, a Mariner-Based Transposon". Applied and Environmental Microbiology, vol. 72, No. 1, Jan. 1, 2006, pp. 327-333.

Andrea Feucht et al. "Identification of Sporulation Genes by Genome-Wide Analysis of the E Regulon of *Bacillus subtilis*". Microbiology, vol. 149, No. 10, Oct. 1, 2003, pp. 3023-3034.

Jeff Errington. "Regulation of Endospore Formation in *Bacillus subtilis*". Nature Reviews, Microbiology, vol. 1, No. 2, Nov. 1, 2003, pp. 117-126.

Howard M Salis et al. "Automated Design of Synthetic Ribosome Binding Sites to Control Protein Expression". Nature Biotechnology, vol. 27, No. 10, Oct. 1, 2009, pp. 946-950.

Eichenberger et al. "The σE regulon and the identification of additional sporulation genes in *Bacillus subtilis*." J. Mol. Biol. (2003), 327: 945-972 (Year: 2003).

*Primary Examiner* — Iqbal H Chowdhury
(74) *Attorney, Agent, or Firm* — Oliff PLC

(57) ABSTRACT

A genetically modified *Bacillus subtilis* strain has been transformed with an optimized vector, mainly for producing a D-psicose 3-epimerase.

4 Claims, 10 Drawing Sheets

Specification includes a Sequence Listing.

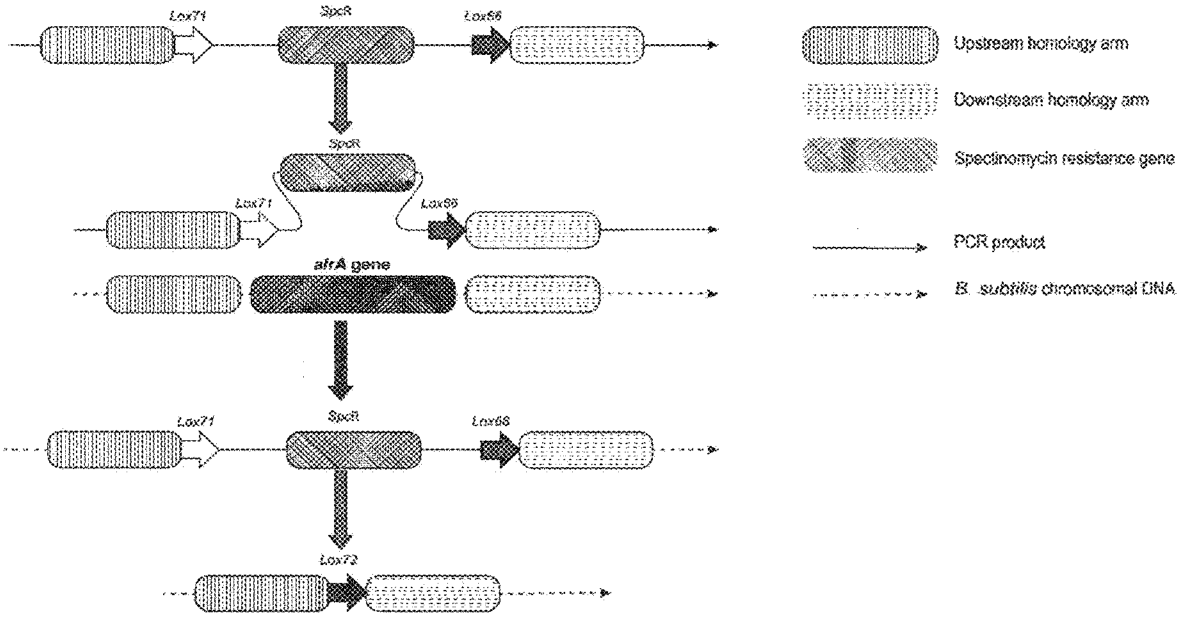
Figure 1. Strategy for the deletion of the *alrA* structural gene

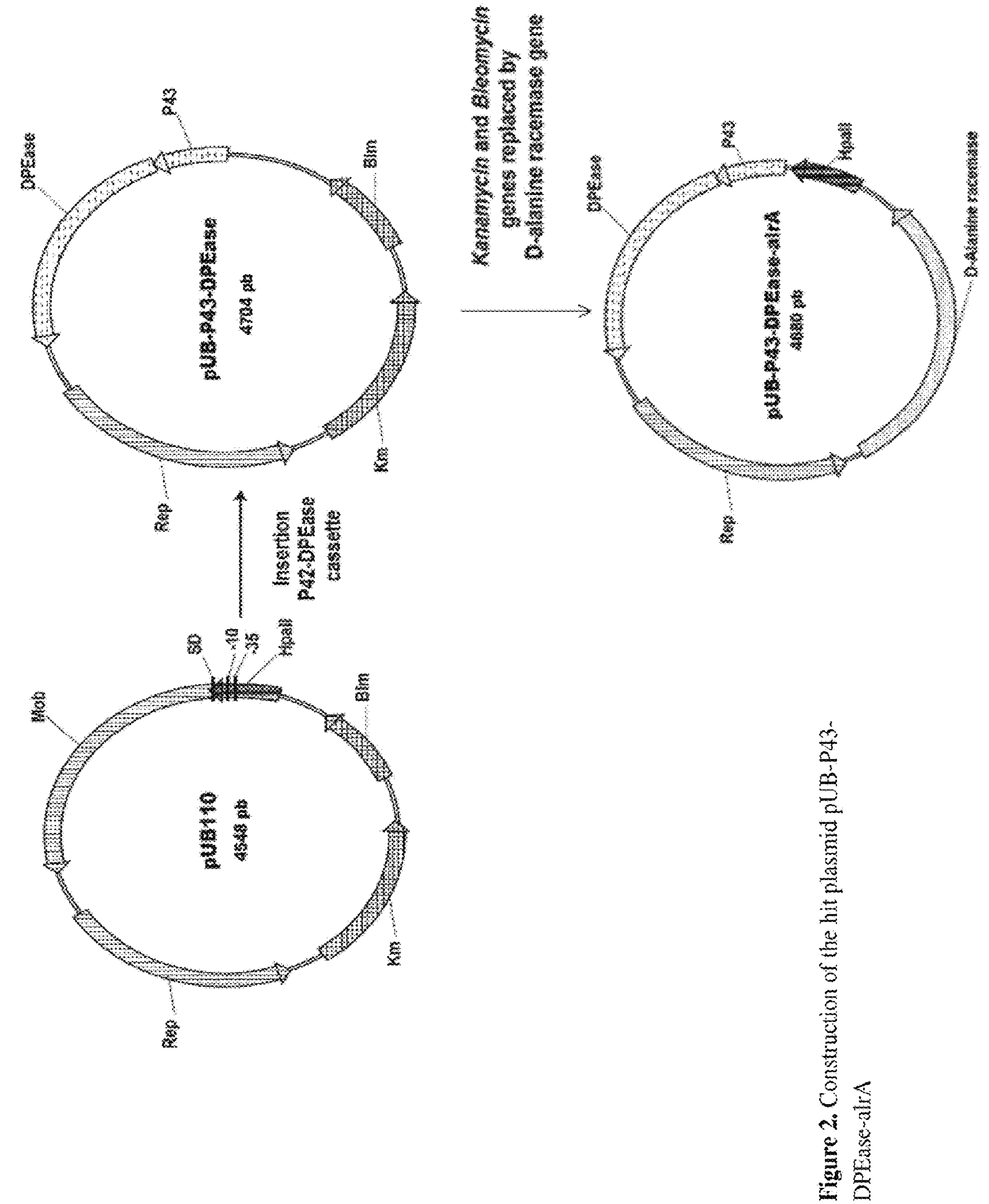
Figure 2. Construction of the hit plasmid pUB-P43-DPEase-alrA

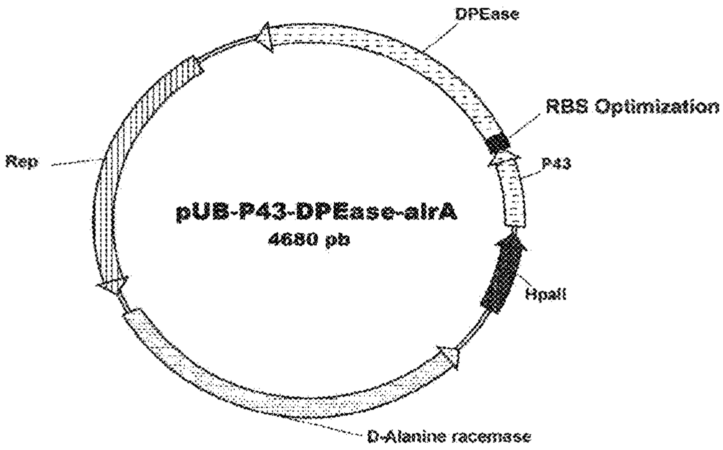
Figure 3. Outline of the pR1/pR2/pR3 vector. The sequence region modified with respect to translational efficiency in pR2/pR3 is outlined as a black box

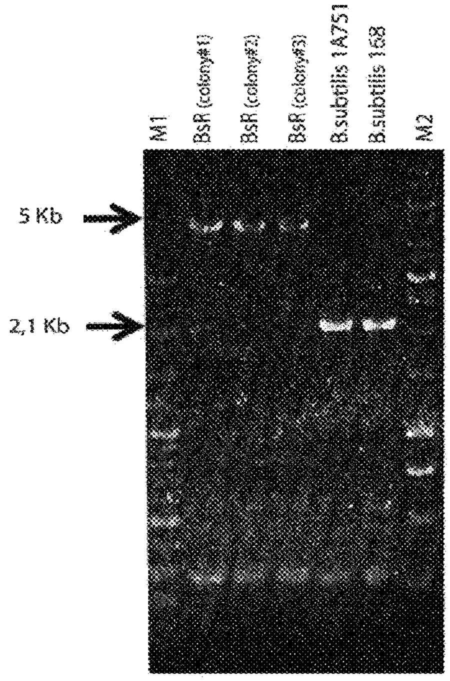
Figure 4. PCR analysis of the beta-galactosidase genomic locus

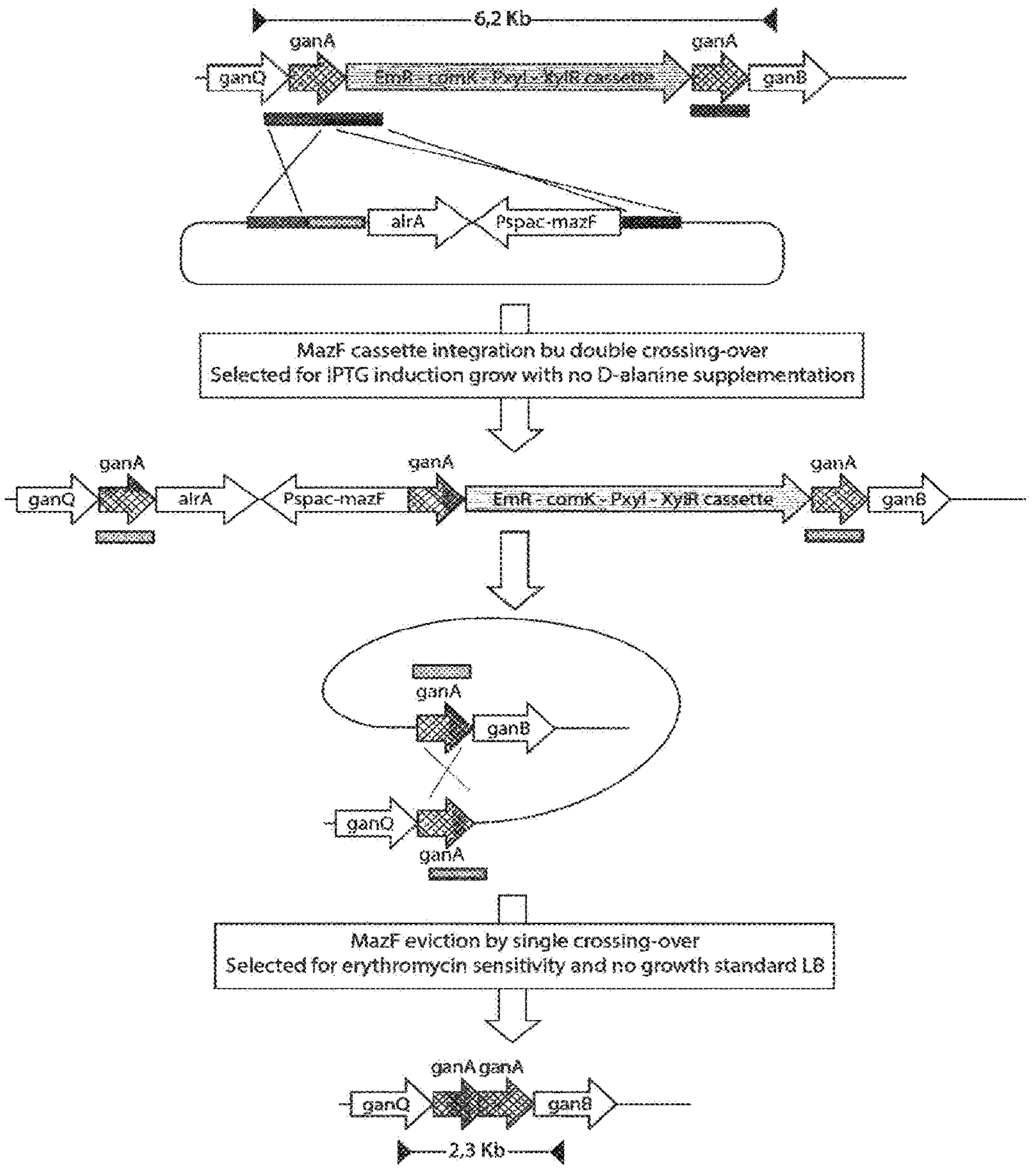
Figure 5. Flow scheme for the cassette EmR-ComK removal using MazF cassette. X indicates on crossing-over event

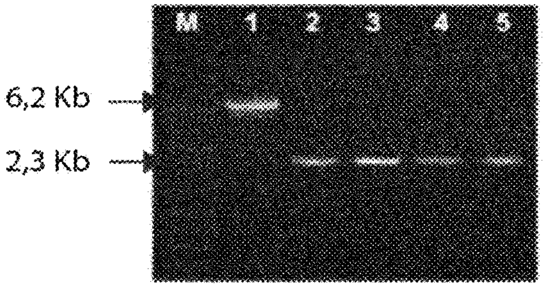
Figure 6. PCR analysis
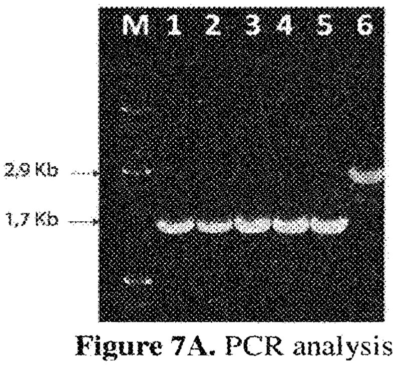
Figure 7A. PCR analysis
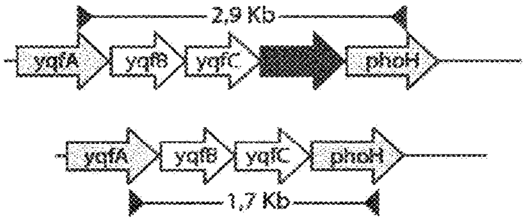
Figure 7B. genetic setup of sporulation locus *yqfD*

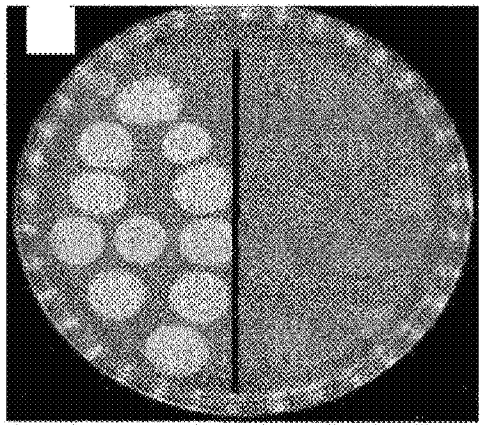
Figure 8A.
Phenotype analysis of *ΔyqfD* (BsR4).
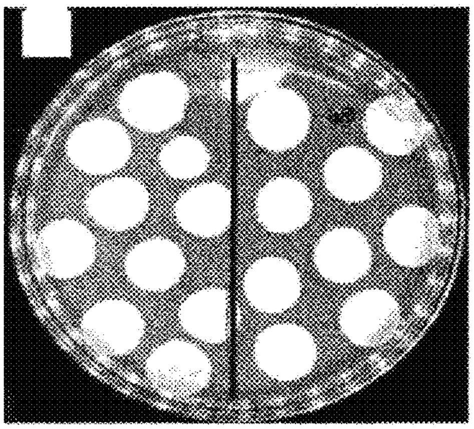
Figure 8B.
Phenotype analysis of *ΔyqfD* (BsR).
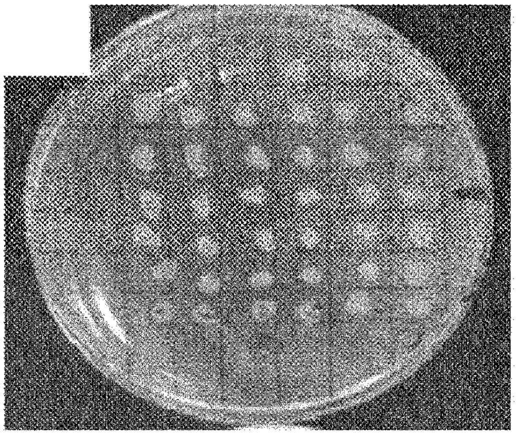
Figure 9A. Phenotypic screening of BsR5 mutant candidates on LB medium supplemented with D-alanine.
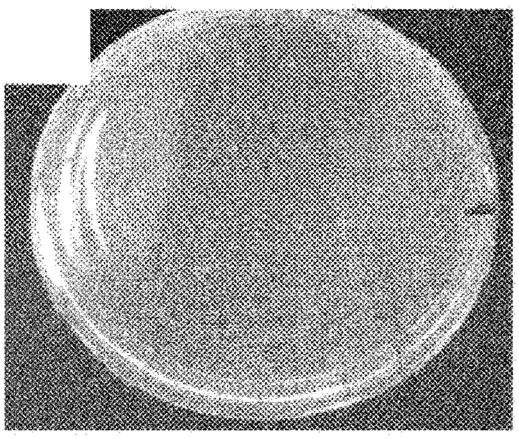
Figure 9B. Phenotypic screening of BsR5 mutant candidates on LB medium.

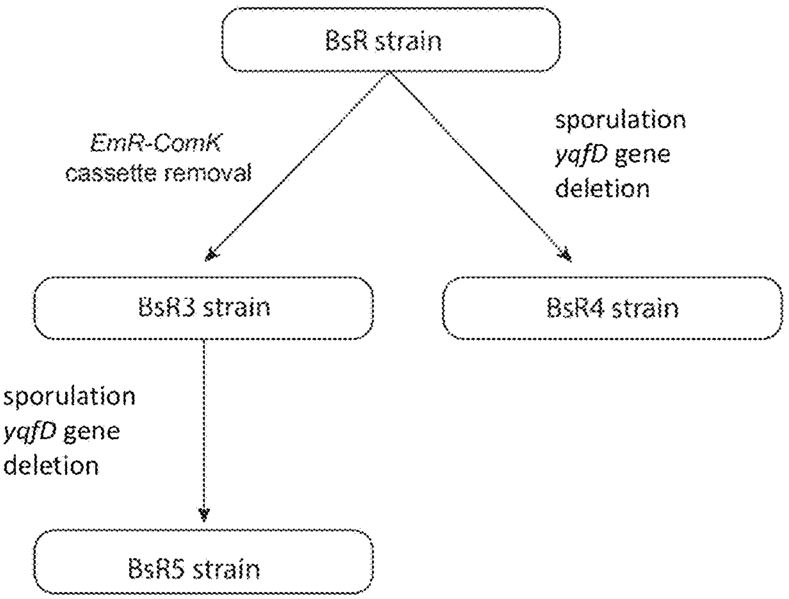
Figure 10. Schematic overview of the strain platform filiation and genetic events applied

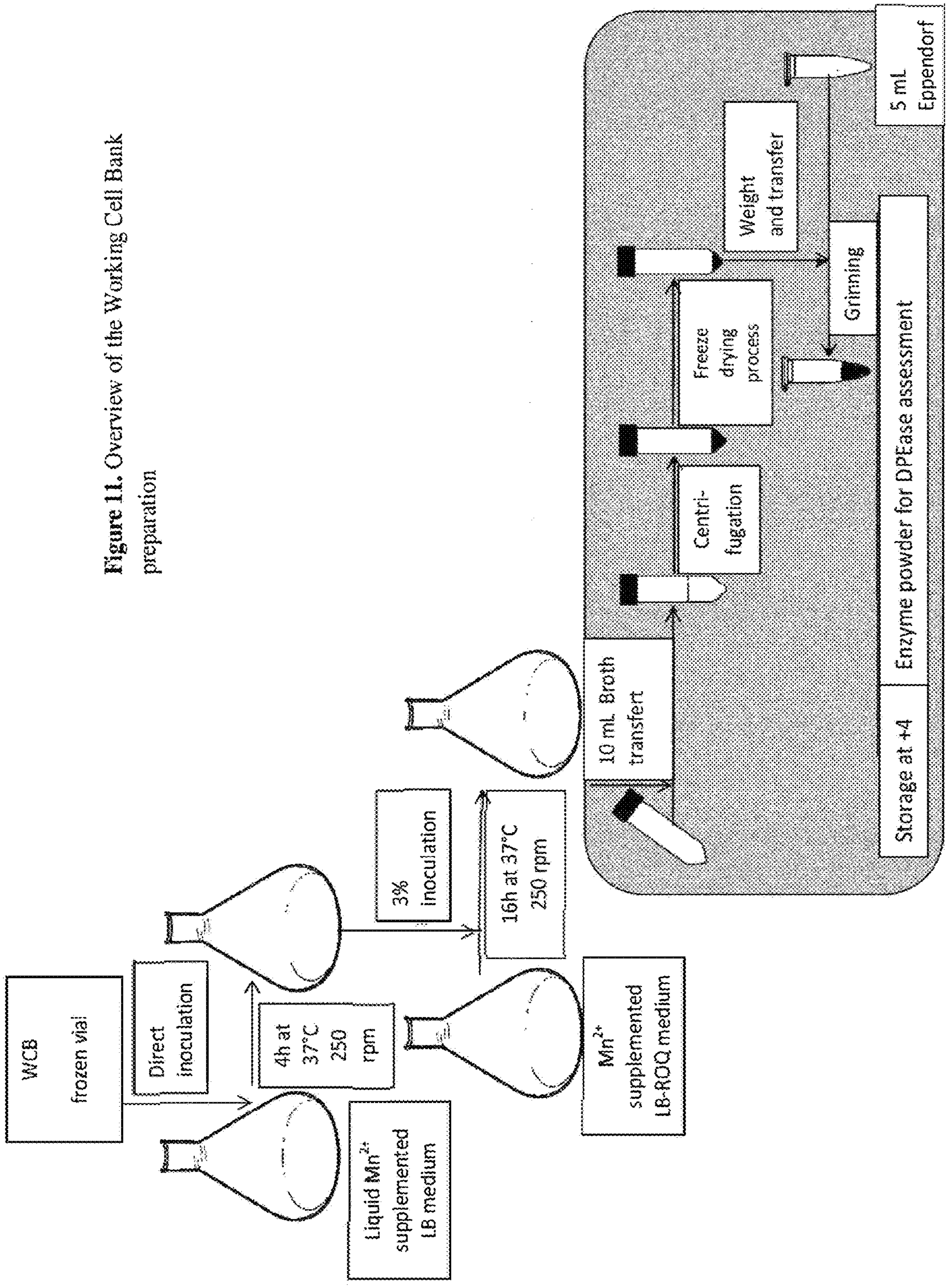
Figure 11. Overview of the Working Cell Bank preparation

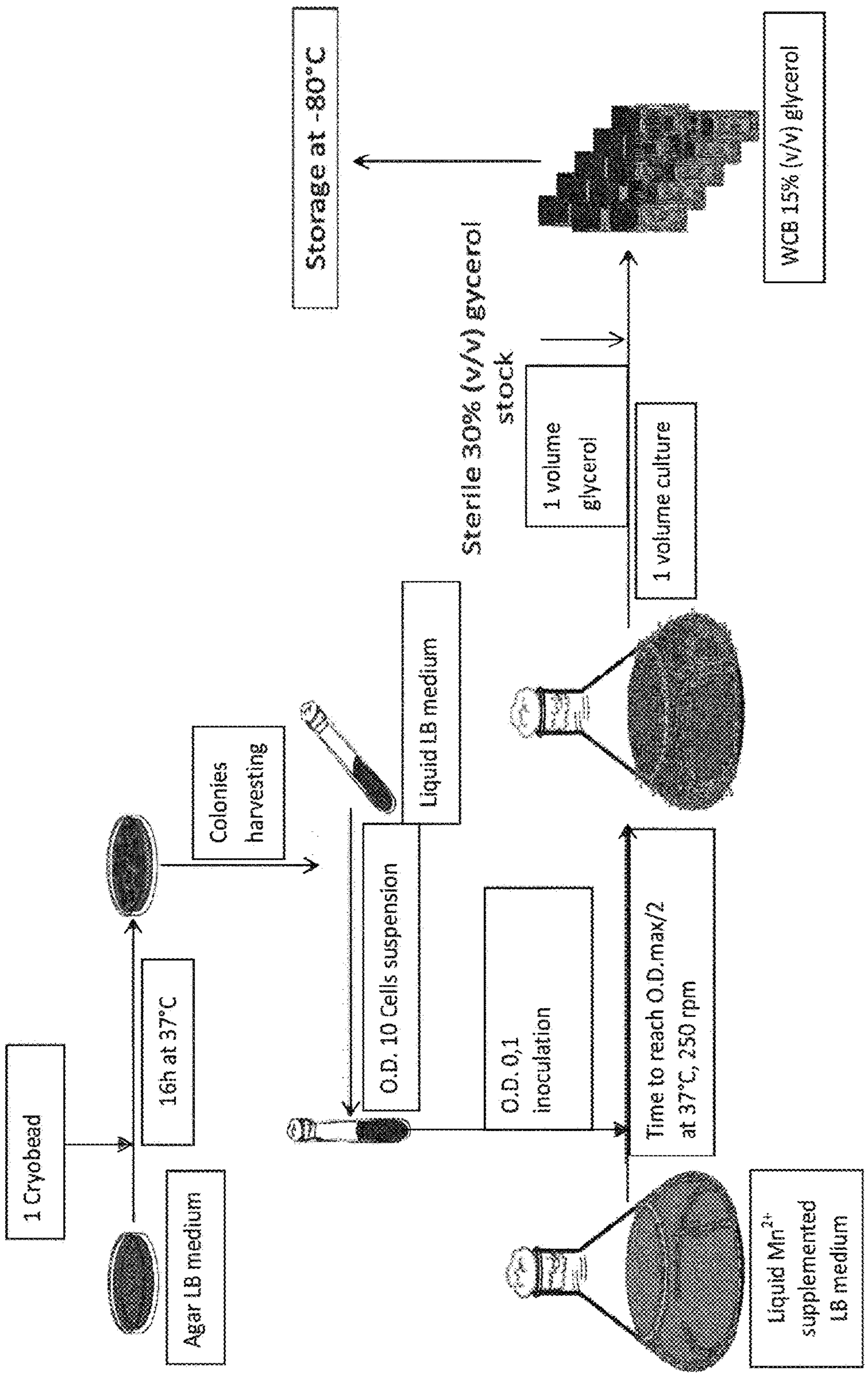
Figure 12. Overview of the strain cultivation providing the DPEase enzyme and its stabilization step (blue tab)

SEQUENCE LISTING

```
Sequence total quantity: 49
SEQ ID NO: 1            moltype = DNA  length = 17
FEATURE                 Location/Qualifiers
misc_feature            1..17
                        note = Optimized RBS
source                  1..17
                        mol_type = other DNA
                        organism = synthetic construct
SEQUENCE: 1
agaaaggagg attacat                                          17

SEQ ID NO: 2            moltype = DNA  length = 17
```

-continued

```
FEATURE                Location/Qualifiers
misc_feature           1..17
                       note = Optimized translation initiation region
source                 1..17
                       mol_type = other DNA
                       organism = synthetic construct
SEQUENCE: 2
agaaaggagg attcgaa                                                17

SEQ ID NO: 3           moltype = DNA  length = 882
FEATURE                Location/Qualifiers
source                 1..882
                       mol_type = genomic DNA
                       organism = Clostridium cellulolyticum
SEQUENCE: 3
atgaaacatg gtatatacta cgcatattgg gaacaagaat gggaagctga ttacaaatac  60
tatattgaga aggttgcaaa gcttggtttt gatattctag agattgcagc ttcaccgcta  120
cctttttaca gtgacattca gattaatgag ctcaaggcat gtgcccatgg caatggaatt  180
acacttacgg taggccatgg gcctagtgca gaacaaaacc tgtcttctcc cgaccccgat  240
attcgcaaaa atgctaaagc tttttatacc gatttactca aacgacttta caagctggat  300
gtacatttga taggtggggc tttatattct tattggccga tagattacac aaagacaatt  360
gataaaaaag gcgattggga acgcagcgtt gaaagtgttc gagaagttgc taaggtggcc  420
gaagcctgtg gagtggattt ctgcctagag gttcttaata gatttgagaa ttatttaatt  480
aacacagcac aagagggtgt agattttgta aaacaggttg accataacaa tgtaaaggta  540
atgcttgata ccttccatat gaatattgag gaagatagta tcggaggtgc aatcaggact  600
gcgggctctt acttgggaca tttacacact ggcgaatgta atcgtaaagt tcccggcaga  660
ggaagaattc catgggtaga aattggtgag gctcttgctg acataggtta taacggtagt  720
gttgttatgg aaccttttgt tagaatgggc ggaactgtcg gatctaatat taaggtttgg  780
cgtgacatta gtaacggtgc agatgagaaa atgctggata gagaagcaca ggccgcactt  840
gatttctcca gatatgtatt agaatgtcat aaacactcct ga                   882

SEQ ID NO: 4           moltype = DNA  length = 888
FEATURE                Location/Qualifiers
misc_feature           1..888
                       note = DPEase H10 de novo synthetized
source                 1..888
                       mol_type = other DNA
                       organism = synthetic construct
SEQUENCE: 4
catatgaaac atggtatata ctacgcatat tgggaacaag aatgggaagc tgattacaaa  60
tactatattg agaaggttgc aaagcttggt tttgatattc tagagattgc agcttcaccg  120
ctaccttttt acagtgacat tcagattaat gagctcaagg catgtgccca tggcaatgga  180
attacactta cggtaggcca tgggcctagt gcagaacaaa acctgtcttc tcccgacccc  240
gatattcgca aaaatgctaa agctttttat accgatttac tcaaacgact ttacaagctg  300
gatgtacatt tgataggtgg ggctttatat tcttattggc cgatagatta cacaaagaca  360
attgataaaa aaggcgattg ggaacgcagc gttgaaagtg ttcgagaagt tgctaaggtg  420
gccgaagcct gtggagtgga tttctgccta gaggttctta atagatttga gaattattta  480
attaacacag cacaagaggg tgtagatttt gtaaaacagg ttgaccataa caatgtaaag  540
gtaatgcttg ataccttcca catgaatatt gaggaagata gtatcggagg tgcaatcagg  600
actgcgggct cttacttggg acatttacac actggcgaat gtaatcgtaa agttcccggc  660
agaggaagaa ttccatgggt agaaattggt gaggctcttg ctgacatagg ttataacggt  720
agtgttgtta tggaaccttt tgttagaatg ggcggaactg tcggatctaa tattaaggtt  780
tggcgtgaca ttagtaacgg tgcagatgag aaaatgctgg atagagaagc acaggccgca  840
cttgatttct ccagatatgt attagaatgt cataaacact ccctcgag              888

SEQ ID NO: 5           moltype = AA  length = 293
FEATURE                Location/Qualifiers
REGION                 1..293
                       note = Artificial construct
source                 1..293
                       mol_type = protein
                       organism = synthetic construct
SEQUENCE: 5
MKHGIYYAYW EQEWEADYKY YIEKVAKLGF DILEIAASPL PFYSDIQINE LKACAHGNGI  60
TLTVGHGPSA EQNLSSPDPD IRKNAKAFYT DLLKRLYKLD VHLIGGALYS YWPIDYTKTI  120
DKKGDWERSV ESVREVAKVA EACGVDFCLE VLNRFENYLI NTAQEGVDFV KQVDHNNVKV  180
MLDTFHMNIE EDSIGGAIRT AGSYLGHLHT SECNRKVPGR GRIPWVEIGE ALADIGYNGS  240
VVMEPFVRMG GTVGSNIKVW RDISNGADEK MLDREAQAAL DFSRYVLECH KHS         293

SEQ ID NO: 6           moltype = AA  length = 293
FEATURE                Location/Qualifiers
REGION                 1..293
                       note = Artificial construct
source                 1..293
                       mol_type = protein
                       organism = synthetic construct
SEQUENCE: 6
MKHGIYYAYW EQEWEADYKY YIEKVAKLGF DILEIAASPL PFYSDIQINE LKACAHGNGI  60
TLTVGHGPSA EQNLSSPDPD IRKNAKAFYT DLLKRLYKLD VHLIGGALYS YWPIDYTKTI  120
```

-continued

```
DKKGDWERSV ESVREVAKVA EACGVDFCLE VLNRFENYLI NTAQEGVDFV KQVDHNNVKV  180
MLDTFHMNIE EDSIGGAIRT AGSYLGHLHT SECNRKVPGR GRIPWVEIGE ALADIGYNGS  240
VVMEPFVRMG GTVGSNIKVW RDISNGADEK MLDREAQAAL DFSRYVLECH KHS         293

SEQ ID NO: 7           moltype = AA  length = 292
FEATURE                Location/Qualifiers
REGION                 1..292
                       note = Artificial construct
source                 1..292
                       mol_type = protein
                       organism = synthetic construct
SEQUENCE: 7
MKHGIYYAYW EQEWEADYKY YIEKVAKLGF DILEIAASPL PFYSDNQINE LKACARGNGI  60
TLTVGHGPSA EQNLSSPDPY IRKNAKAFYT DLLKRLYKLD VHLIGGAIYS YWPVDYTKTI  120
DKKGDWERSV ESVREVAQVA EACGVDFCLE VLNRFENYLI NTAQEGVDFV KQVGHDNVKV  180
MLDTFHMNIE EDSIGGAIRT AGSYLGHLHT SECNRKVPGK GRIPWIEIGE ALADIGYNGS  240
VVMEPFVRMG GTVGSNIKVW RDISNGADEE KLDREAQAAL NFSRYVLGNR KL          292

SEQ ID NO: 8           moltype = AA  length = 289
FEATURE                Location/Qualifiers
REGION                 1..289
                       note = Artificial construct
source                 1..289
                       mol_type = protein
                       organism = synthetic construct
SEQUENCE: 8
MKHGIYYAYW EQEWAADYKR YVEKAAKLGF DILEVGAAPL PDYSAQEVKE LKKCADDNGI  60
QLTAGYGPAF NHNMGSSDPK IREEALQWYK RLFEVMAGLD IHLIGGALYS YWPVDFATAN  120
KEEDWKHSVE GMQILAPIAS QYGINLGMEV LNRFESHILN TSEEGVKFVT EVGMDNVKVM  180
LDTFHMNIEE SSIGDAIRHA GKLLGHFHTS ECNRMVPGKG RTPWREIGDA LREIEYDGTV  240
VMEPFVRMGG QVGSDIKVWR DISKGAGEDR LDEDARRAVE FQRYMLEWK               289

SEQ ID NO: 9           moltype = AA  length = 288
FEATURE                Location/Qualifiers
REGION                 1..288
                       note = Artificial construct
source                 1..288
                       mol_type = protein
                       organism = synthetic construct
SEQUENCE: 9
MKHGIYYSYW EHEWSAKFGP YIEKVAKLGF DIIEVAAHHI NEYSDAELAT IRKSAKDNGI  60
ILTAGIGPSK TKNLSSEDAA VRAAGKAFFE RTLSNVAKLD IHTIGGALHS YWPIDYSQPV  120
DKAGDYARGV EGINGIADFA NDLGINLCIE VLNRFENHVL NTAAEGVAFV KDVGKNNVKV  180
MLDTFHMNIE EDSFGDAIRT AGPLLGHFHT SESNRRVPGK GRMPWHEIGL ALRDINYTGA  240
VIMEPFVKTG GTIGSDIKVW RDLSGGADIA KMDEDARNAL AFSRFVLG                288

SEQ ID NO: 10          moltype = AA  length = 291
FEATURE                Location/Qualifiers
REGION                 1..291
                       note = Artificial construct
source                 1..291
                       mol_type = protein
                       organism = synthetic construct
SEQUENCE: 10
MKYGIYYAYW EKEWNGDYKY YIDKISKLGF DILEISCGAF SDYYTKDQEL IDIGKYAKEK  60
GVTLTAGYGP HFNESLSSSE PNTQKQAISF WKETLRKLKL MDIHIVGGAL YGYWPVDYSK  120
PFDKKRDLEN SIKNMKIISQ YAEEYDIMMG MEVLNRFEGY MLNTCDEALA YVEEVGSSNV  180
GVMLDTFHMN IEEDNIAAAI RKAGDRLYHF HISEGNRKVP GKGMLPWNEI GQALRDINYQ  240
HAAVMEPFVM QGGTVGHDIK IWRDIIGNCS EVTLDMDAQS ALHFVKHVFE V             291

SEQ ID NO: 11          moltype = AA  length = 301
FEATURE                Location/Qualifiers
REGION                 1..301
                       note = Artificial construct
source                 1..301
                       mol_type = protein
                       organism = synthetic construct
SEQUENCE: 11
MRYFKEEVAG MKYGIYFAYW TKEWFADYKK YMDKVSALGF DVLEISCAAL RDVYTTKEQL  60
IELREYAKEK GLVLTAGYGP TKAENLCSED PEAVRRAMTF FKDLLPKLQL MDIHILGGGL  120
YSYWPVDFTI NNDKQGDRAR AVRNLRELSK TAEECDVVLG MEVLNRYEGY ILNTCEEAID  180
FVDEIGSSHV KIMLDTFHMN IEETNMADAI RKAGDRLGHL HLSEQNRLVP GKGSLPWAEI  240
GQALRDINYQ GAAVMEPFVM QGGTIGSEIK VWRDMVPDLS EEALDRDAKG ALEFCRHVFG  300
I                                                                   301

SEQ ID NO: 12          moltype = AA  length = 290
FEATURE                Location/Qualifiers
REGION                 1..290
                       note = Artificial construct
```

```
source                  1..290
                        mol_type = protein
                        organism = synthetic construct
SEQUENCE: 12
MNKVGMFYTY WSTEWMVDFP ATAKRIAGLG FDLMEISLGE FHNLSDAKKR ELKAVADDLG  60
LTVMCCIGLK SEYDFASPDK SVRDAGTEYV KRLLDDCHLL GAPVFAGLTF CAWPQSPPLD  120
MKDKRPYVDR AIESVRRVIK VAEDYGIIYA LEVVNRFEQW LCNDAKEAIA FADAVDSPAC  180
KVQLDTFHMN IEETSFRDAI LACKGKMGHF HLSEANRLPP GEGRLPWDEI FGALKEIGYD  240
GTIVMEPFMR KGGSVSRAVG VWRDMSNGAT DEEMDERARR SLQFVRDKLA             290

SEQ ID NO: 13           moltype = AA  length = 295
FEATURE                 Location/Qualifiers
REGION                  1..295
                        note = Artificial construct
source                  1..295
                        mol_type = protein
                        organism = synthetic construct
SEQUENCE: 13
MKNPVGIISM QFIRPFTSES LHFLKKSRAL GFDFIELLVP EPEDGLDAAE VRRICEGEGL  60
GLVLAARVNL QRSIASEEAA ARAGGRDYLK YCIEAAEALG ATIVGGPLYG EPLVFAGRPP  120
FPWTAEQIAT RAARTVEGLA EVAPLAASAG KVFGLEPLNR FETDIVNTTA QAIEVVDAVG  180
SPGLGVMLDT FHMNMEERSI PDAIRATGAR LVHFQANENH RGFPGTGTMD WTAIARALGQ  240
AGYAGPVSLE PFRRDDERVA LPIAHWRAPH EDEDEKLRAG LGLIRSAITL AEVTH       295

SEQ ID NO: 14           moltype = DNA  length = 4681
FEATURE                 Location/Qualifiers
misc_feature            1..4681
                        note = Plasmid pR1
source                  1..4681
                        mol_type = other DNA
                        organism = synthetic construct
SEQUENCE: 14
cttaaggaac gtacagacgg cttaaaagcc tttaaaaacg tttttaaggg gtttgtagac  60
aaggtaaagg ataaaacagc acaattccaa gaaaaacacg atttagaacc taaaaagaac  120
gaatttgaac taactcataa ccgagaggta aaaaaagaac gaagtcgaga tcagggaatg  180
agtttataaa ataaaaaaag cacctgaaaa ggtgtctttt tttgatggtt ttgaacttgt  240
tctttcttat cttgatacat atagaaataa cgtcattttt attttagttg ctgaaaggtg  300
cgttgaagtg ttggtatgta tgtgttttaa agtattgaaa acccttaaaa ttggttgcac  360
agaaaaaccc catctgttaa agttataagt gactaaacaa ataactaaat agatgggggt  420
ttcttttaat attatgtgtc ctaatagtag catttattca gatgaaaaat caagggtttt  480
agtggacaag acaaaaagtg gaaaagtgag accatggaga gaaaagaaaa tcgctaatgt  540
tgattacttt gaacttctgc atattcttga atttaaaaag gctgaaagag taaaagattg  600
tgctgaaata ttagagtata aacaaaatcg tgaaacaggc gaaagaaagt tgtatcgagt  660
gtggttttgt aaatccaggc tttgtccaat gtgcaactgg aggagagcaa tgaaacatgg  720
cattcagtca caaaaggttg ttgctgaagt tattaaacaa aagccaacag ttcgttggtt  780
gtttctcaca ttaacagtta aaaatgttta tgatggcgaa gaattaaata agagtttgtc  840
agatatggct caaggatttc gccgaatgat gcaatataaa aaaattaata aaaatcttgt  900
tggttttatg cgtgcaacgg aagtgacaat aaataataaa gataattctt ataatcagca  960
catgcatgta ttggtatgtg tggaaccaac ttattttaag aatacagaaa actacgtgaa  1020
tcaaaaacaa tggattcaat tttggaaaaa ggcaatgaaa ttagactatg atccaaatgt  1080
aaaagttcaa atgattcgac cgaaaaataa atataaatcg gatatacaat cggcaattga  1140
cgaaactgca aaatatcctg taaaggatac ggattttatg accgatgatg aagaaaagaa  1200
tttgaaacgt ttgtctgatt tggaggaagg tttacaccgt aaaaggttaa tctcctatgg  1260
tggtttgtta aaagaaatac ataaaaaatt aaaccttgat gacacagaag aaggcgattt  1320
gattcataca gatgatgacg aaaaagccga tgaagatgga ttttctatta ttgcaatgtg  1380
gaattgggaa cggaaaaatt attttattaa agagtagttc aacaaacggg ccagtttgtt  1440
gaagattaga tgctataatt gttattaaaa ggattgaagg atgcttagga agacgagtta  1500
ttaatagctg aataagaacg gtgctctcca aatattctta tttagaaaag caaatctaaa  1560
attatctgaa aagggaagat ctttctaaag aggaaatggt gacagtagcg aaaagcatgc  1620
agggacaatc atcgaaataa ccgccaaagg ccaaacatga tttggccttt ttttcgttag  1680
acatcgtttc cctttagcct ttaattttag tatgatatgt aaatgatatt gaataaaagc  1740
taggaagtgt cgtaatgagc acaaaacctt tttacagaga tacgtgggcg gaaattgact  1800
tgtccgcgat aaaggaaaat gtcagcaata tgaaaaaaca tatcggtgaa catgtccact  1860
tgatggcagt tgtgaaagca aacgcctacg ggcatggtga tgcagaaaca gcaaaggctg  1920
ctcttgacgc aggtgcttca tgcttggccg tggccatttt ggatgaagcg atttcactgc  1980
gcaaaaaggg attgaaggcg cctatattgg tgcttggcgc ggttcccccg gagtatgtgg  2040
caatcgctgc tgagtatgac gtgaccttaa caggttattc tgttgaatgg cttcaggagg  2100
cagcccgcca cacgaaaaaa ggttctcttc attttcatct gaaggtcgat acggggatga  2160
acagacttgg tgtaaaaaca gaggaagaag ttcagaacgt gatggcaatt cttgaccgca  2220
accctcgttt aaagtgcaaa ggggtattta cccattttgc gacagcggat gaaaaagaaa  2280
gaggctattt cttaatgcag tttgagcgct ttaaagagct gattgctccg ctgccgttaa  2340
agaatctaat ggtccactgc gcgaacagcg ccgctggact ccggctgaaa aaaggctttt  2400
ttaatgcagt cagattcggc atcggcatgt atggccttcg cccgtctgct gacatgtcgg  2460
acgagatacc gtttcagctg cgtccggcat ttaccctgca ttcgacactg tcacatgtca  2520
aactgatcag aaaaggcgag agcgtcagct acggagccga gtacacagcg gaaaaagaca  2580
catggatcgg gacggtgcct gtaggctatg cggacggctg gctccgaaaa ttgaaaggga  2640
ccgacatcct tgtgaaggga aaacgcctga aaattgccgg ccgaatttgc atggaccaat  2700
ttatggtgga gctggatcag gaatatccgc cgggcacaaa agtcacatta ataggccggc  2760
agggggatga atatatttcc atggatgaga ttgcaggaag gctcgaaacc attaactatg  2820
```

-continued

```
aggtggcctg tacaataagt tcccgtgttc cccgtatgtt tttggaaaat gggagtataa  2880
tggaagtaag aaatccttta ttgcaggtaa atataagcaa ttaacttacc taaatggaga  2940
attcaatcta ttattaatct gttcagcaat cgggcgcgat tgctgaataa aagatacgag  3000
agacctctct tgtatctttt ttattttgag tggttttgtc cgttacacta gaaaaccgaa  3060
agacaataaa aattttattc ttgctgagtc tggctttcgg taagctagac aaaacggaca  3120
aaataaaaat tggcaagggt ttaaaggtgg agatttttg agtgatcttc tcaaaaaata  3180
ctacctgtcc cttgctgatt tttaaacgag cacgagagca aaacccccct ttgctgaggt  3240
ggcagagggc aggtttttt gtttctttt tctcgtaaaa aaaagaaagg tcttaaaggt  3300
tttatggttt tggtcggcac tgccgacagc ctcgcagagc acacacttta tgaatataaa  3360
gtatagtgtg ttatacttta cttggaagtg gttgccggaa agagcgaaaa tgcctcacat  3420
ttgtgccacc taaaaaggag cgatttacat atgagttatg cagtttgtag aatgcaaaaa  3480
gtgaaatcat aatgataggt ggtatgtttt cgcttgaact tttaaataca gccattgaac  3540
atacggttga tttaataact gacaaacatc accctcttgc taaagcggcc aaggacgctg  3600
ccgccggggc tgtttgcgtt tttgccgtga tttcgtgtat cattggttta cttattttt  3660
tgccaaagct gtaatggctg aaaattctta catttatatt tacattttta gaaatgggcg  3720
tgaaaaaaag cgcgcgatta tgtaaaatat aaagtgatag cggtaccatt ataggtaaga  3780
gaggaatgta cacatgaaac atggtatata ctacgcatat tgggaacaag aatgggaagc  3840
tgattacaaa tactatattg agaaggttgc aaagcttggt tttgatattc tagagattgc  3900
agcttcaccg ctaccttttt acagtgacat tcagattaat gagctcaagg catgtgccca  3960
tggcaatgga attacactta cggtaggcca tgggcctagt gcagaacaaa acctgtcttc  4020
tcccgacccc gatattcgca aaaatgctaa agcttttat accgatttac tcaaacgact  4080
ttacaagctg gatgtacatt tgataggtgg ggctttatat tcttattggc cgatagatta  4140
cacaaagaca attgataaaa aaggcgattg ggaacgcagc gttgaaagtg ttcgagaagt  4200
tgctaaggtg gccgaagcct gtggagtgga tttctgccta gaggttctta atagatttga  4260
gaattattta attaacacag cacaagaggg tgtagatttt gtaaaacagg ttgaccataa  4320
caatgtaaag gtaatgcttg ataccttcca catgaatatt gaggaagata gtatcggagg  4380
tgcaatcagg actgcgggct cttacttggg acatttacac actggcgaat gtaatcgtaa  4440
agttcccggc agaggaagaa ttccatgggt agaaattggt gaggctcttg ctgacatagg  4500
ttataacggt agtgttgtta tggaaccttt tgttagaatg ggcggaactg tcggatctaa  4560
tattaaggtt tggcgtgaca ttagtaacgg tgcagatgag aaaatgctgg atagagaagc  4620
acaggccgca cttgatttct ccagatatgt attagaatgt cataaacact cctaagaatt  4680
c                                                                  4681
```

```
SEQ ID NO: 15          moltype = DNA  length = 4681
FEATURE                Location/Qualifiers
misc_feature           1..4681
                       note = Plasmid pR2
source                 1..4681
                       mol_type = other DNA
                       organism = synthetic construct
SEQUENCE: 15
cttaaggaac gtacagacgg cttaaaagcc tttaaaaacg tttttaaggg gtttgtagac  60
aaggtaaagg ataaaacagc acaattccaa gaaaaacacg atttagaacc taaaaagaac  120
gaatttgaac taactcataa ccgagaggta aaaaaagaac gaagtcgaga tcagggaatg  180
agtttataaa ataaaaaaag cacctgaaaa ggtgtctttt tttgatggtt ttgaacttgt  240
tctttcttat cttgatacat atagaaataa cgtcattttt attttagttg ctgaaaggtg  300
cgttgaagtg ttggtatgta tgtgttttaa agtattgaaa acccttaaaa ttggttgcac  360
agaaaaaccc catctgttaa agttataagt gactaaacaa ataactaaat agatgggggt  420
ttcttttaat attatgtgtc ctaatagtag catttattca gatgaaaaat caagggtttt  480
agtggacaag acaaaaagtg gaaaagtgag accatggaga gaaaagaaaa tcgctaatgt  540
tgattacttt gaacttctgc atattcttga atttaaaaag gctgaaagag taaaagattg  600
tgctgaaata ttagagtata aacaaaatcg tgaaacaggc gaaagaaagt tgtatcgagt  660
gtggttttgt aaatccaggc tttgtccaat gtgcaactgg aggagagcaa tgaaacatgg  720
cattcagtca caaaaggttg ttgctgaagt tattaaacaa aagccaacag ttcgttggtt  780
gtttctcaca ttaacagtta aaaatgttta tgatggcgaa gaattaaata agagtttgtc  840
agatatggct caaggatttc gccgaatgat gcaatataaa aaaattaata aaaatcttgt  900
tggttttatg cgtgcaacgg aagtgacaat aaataataaa gataattctt ataatcagca  960
catgcatgta ttggtatgtg tggaaccaac ttattttaag aatacagaaa actacgtgaa  1020
tcaaaaacaa tggattcaat tttggaaaaa ggcaatgaaa ttagactatg atccaaatgt  1080
aaaagttcaa atgattcgac cgaaaaataa atataaatcg gatatacaat cggcaattga  1140
cgaaactgca aaatatcctg taaaggatac ggattttatg accgatgatg aagaaaagaa  1200
tttgaaacgt ttgtctgatt tggaggaagg tttacaccgt aaaaggttaa tctcctatgg  1260
tggtttgtta aaagaaatac ataaaaaatt aaaccttgat gacacagaag aaggcgattt  1320
gattcataca gatgatgacg aaaaagccga tgaagatgga ttttctatta ttgcaatgtg  1380
gaattgggaa cggaaaaatt attttattaa agagtagttc aacaaacggg ccagtttgtt  1440
gaagattaga tgctataatt gttattaaaa ggattgaagg atgcttagga agacgagtta  1500
ttaatagctg aataagaacg gtgctctcca aatattctta tttagaaaag caaatctaaa  1560
attatctgaa aagggaagat ctttctaaag aggaaatggt gacagtagcg aaaagcatgc  1620
agggacaatc atcgaaataa ccgccaaagg ccaaacatga tttggccttt ttttcgttag  1680
acatcgtttc cctttagcct ttaattttag tatgatatgt aaatgatatt gaataaaagc  1740
taggaagtgt cgtaatgagc acaaaacctt tttacagaga tacgtgggcg gaaattgact  1800
tgtccgcgat aaaggaaaat gtcagcaata tgaaaaaaca tatcggtgaa catgtccact  1860
tgatggcagt tgtgaaagca aacgcctacg ggcatggtga tgcagaaaca gcaaaggctg  1920
ctcttgacgc aggtgcttca tgcttggccg tggccatttt ggatgaagcg atttcactgc  1980
gcaaaaaggg attgaaggcg cctatattgg tgcttggcgc ggttcccccg gagtatgtgg  2040
caatcgctgc tgagtatgac gtgaccttaa caggttattc tgttgaatgg cttcaggagg  2100
cagcccgcca cacgaaaaaa ggttctcttc attttcatct gaaggtcgat acggggatga  2160
acagacttgg tgtaaaaaca gaggaagaag ttcagaacgt gatggcaatt cttgaccgca  2220
accctcgttt aaagtgcaaa ggggtattta cccattttgc gacagcggat gaaaaagaaa  2280
```

-continued

```
gaggctattt cttaatgcag tttgagcgct ttaaagagct gattgctccg ctgccgttaa  2340
agaatctaat ggtccactgc gcgaacagcg ccgctggact ccggctgaaa aaaggctttt  2400
ttaatgcagt cagattcggc atcggcatgt atggccttcg cccgtctgct gacatgtcgg  2460
acgagatacc gtttcagctg cgtccggcat ttaccctgca ttcgacactg tcacatgtca  2520
aactgatcag aaaaggcgag agcgtcagct acggagccga gtacacagcg gaaaaagaca  2580
catggatcgg gacggtgcct gtaggctatg cggacggctg gctccgaaaa ttgaaaggga  2640
ccgacatcct tgtgaaggga aaacgcctga aaattgccgg ccgaatttgc atggaccaat  2700
ttatggtgga gctggatcag gaatatccgc cgggcacaaa agtcacatta ataggccggc  2760
agggggatga atatatttcc atggatgaga ttgcaggaag gctcgaaacc attaactatg  2820
aggtggcctg tacaataagt tcccgtgttc cccgtatgtt tttggaaaat gggagtataa  2880
tggaagtaag aaatccttta ttgcaggtaa atataagcaa ttaacttacc taaatggaga  2940
attcaatcta ttattaatct gttcagcaat cgggcgcgat tgctgaataa aagatacgag  3000
agacctctct tgtatctttt ttattttgag tggttttgtc cgttacacta gaaaaccgaa  3060
agacaataaa aattttattc ttgctgagtc tggctttcgg taagctagac aaaacggaca  3120
aaataaaaat tggcaagggt ttaaaggtgg agatttttg agtgatcttc tcaaaaaata  3180
ctacctgtcc cttgctgatt tttaaacgag cacgagagca aaaccccct ttgctgaggt  3240
ggcagagggc aggtttttt gtttcttttt tctcgtaaaa aaaagaaagg tcttaaaggt  3300
tttatggttt tggtcggcac tgccgacagc ctcgcagagc acacacttta tgaatataaa  3360
gtatagtgtg ttatacttta cttggaagtg gttgccggaa agagcgaaaa tgcctcacat  3420
ttgtgccacc taaaaaggag cgatttacat atgagttatg cagtttgtag aatgcaaaaa  3480
gtgaaatcat aatgataggt ggtatgtttt cgcttgaact tttaaataca gccattgaac  3540
atacggttga tttaataact gacaaacatc accctcttgc taaagcggcc aaggacgctg  3600
ccgccggggc tgtttgcgtt tttgccgtga tttcgtgtat cattggttta cttatttttt  3660
tgccaaagct gtaatggctg aaaattctta catttatatt tacattttta gaaatgggcg  3720
tgaaaaaaag cgcgcgatta tgtaaaatat aaagtgatag cggtaccatt ataggtagaa  3780
aggaggatta catatgaaac atggtatata ctacgcatat tgggaacaag aatgggaagc  3840
tgattacaaa tactatattg agaaggttgc aaagcttggt tttgatattc tagagattgc  3900
agcttcaccg ctaccttttt acagtgacat tcagattaat gagctcaagg catgtgccca  3960
tggcaatgga attacactta cggtaggcca tgggcctagt gcagaacaaa acctgtcttc  4020
tcccgacccc gatattcgca aaaatgctaa agctttttat accgatttac tcaaacgact  4080
ttacaagctg gatgtacatt tgataggtgg ggctttatat tcttattggc cgatagatta  4140
cacaaagaca attgataaaa aaggcgattg ggaacgcagc gttgaaagtg ttcgagaagt  4200
tgctaaggtg gccgaagcct gtggagtgga tttctgccta gaggttctta atagatttga  4260
gaattattta attaacacag cacaagaggg tgtagatttt gtaaaacagg ttgaccataa  4320
caatgtaaag gtaatgcttg ataccttcca catgaatatt gaggaagata gtatcggagg  4380
tgcaatcagg actgcgggct cttacttggg acatttacac actggcgaat gtaatcgtaa  4440
agttcccggc agaggaagaa ttccatgggt agaaattggt gaggctcttg ctgacatagg  4500
ttataacggt agtgttgtta tggaaccttt tgttagaatg ggcggaactg tcggatctaa  4560
tattaaggtt tggcgtgaca ttagtaacgg tgcagatgag aaaatgctgg atagagaagc  4620
acaggccgca cttgatttct ccagatatgt attagaatgt cataaacact cctaagaatt  4680
c                                                                 4681
```

```
SEQ ID NO: 16           moltype = DNA  length = 4681
FEATURE                 Location/Qualifiers
misc_feature            1..4681
                        note = Plasmid pR3
source                  1..4681
                        mol_type = other DNA
                        organism = synthetic construct
SEQUENCE: 16
cttaaggaac gtacagacgg cttaaaagcc tttaaaaacg tttttaaggg gtttgtagac  60
aaggtaaagg ataaaacagc acaattccaa gaaaaacacg atttagaacc taaaaagaac  120
gaatttgaac taactcataa ccgagaggta aaaaaagaac gaagtcgaga tcagggaatg  180
agtttataaa ataaaaaaag cacctgaaaa ggtgtctttt tttgatggtt ttgaacttgt  240
tctttcttat cttgatacat atagaaataa cgtcattttt attttagttg ctgaaaggtg  300
cgttgaagtg ttggtatgta tgtgttttaa agtattgaaa acccttaaaa ttggttgcac  360
agaaaaaccc catctgttaa agttataagt gactaaacaa ataactaaat agatgggggt  420
ttcttttaat attatgtgtc ctaatagtag catttattca gatgaaaaat caagggtttt  480
agtggacaag acaaaaagtg gaaaagtgag accatggaga gaaaagaaaa tcgctaatgt  540
tgattacttt gaacttctgc atattcttga atttaaaaag gctgaaagag taaaagattg  600
tgctgaaata ttagagtata aacaaaatcg tgaaacaggc gaaagaaagt tgtatcgagt  660
gtggttttgt aaatccaggc tttgtccaat gtgcaactgg aggagagcaa tgaaacatgg  720
cattcagtca caaaaggttg ttgctgaagt tattaaacaa aagccaacag ttcgttggtt  780
gtttctcaca ttaacagtta aaaatgttta tgatggcgaa gaattaaata agagtttgtc  840
agatatggct caaggatttc gccgaatgat gcaatataaa aaaattaata aaaatcttgt  900
tggttttatg cgtgcaacgg aagtgacaat aaataataaa gataattctt ataatcagca  960
catgcatgta ttggtatgtg tggaaccaac ttattttaag aatacagaaa actacgtgaa  1020
tcaaaaacaa tggattcaat tttggaaaaa ggcaatgaaa ttagactatg atccaaatgt  1080
aaaagttcaa atgattcgac cgaaaaataa atataaatcg gatatacaat cggcaattga  1140
cgaaactgca aaatatcctg taaaggatac ggattttatg accgatgatg aagaaaagaa  1200
tttgaaacgt ttgtctgatt tggaggaagg tttacaccgt aaaaggttaa tctcctatgg  1260
tggtttgtta aaagaaatac ataaaaaatt aaaccttgat gacacagaag aaggcgattt  1320
gattcataca gatgatgacg aaaaagccga tgaagatgga ttttctatta ttgcaatgtg  1380
gaattgggaa cggaaaaatt attttattaa agagtagttc aacaaacggg ccagtttgtt  1440
gaagattaga tgctataatt gttattaaaa ggattgaagg atgcttagga agacgagtta  1500
ttaatagctg aataagaacg gtgctctcca aatattctta tttagaaaag caaatctaaa  1560
attatctgaa aagggaagat ctttctaaag aggaaatggt gacagtagcg aaaagcatgc  1620
agggacaatc atcgaaataa ccgccaaagg ccaaacatga tttggccttt ttttcgttag  1680
acatcgtttc cctttagcct ttaattttag tatgatatgt aaatgatatt gaataaaagc  1740
```

-continued

```
taggaagtgt cgtaatgagc acaaaacctt tttacagaga tacgtgggcg gaaattgact  1800
tgtccgcgat aaaggaaaat gtcagcaata tgaaaaaaca tatcggtgaa catgtccact  1860
tgatggcagt tgtgaaagca aacgcctacg ggcatggtga tgcagaaaca gcaaaggctg  1920
ctcttgacgc aggtgcttca tgcttggccg tggccatttt ggatgaagcg atttcactgc  1980
gcaaaaaggg attgaaggcg cctatattgg tgcttggcgc ggttcccccg gagtatgtgg  2040
caatcgctgc tgagtatgac gtgaccttaa caggttattc tgttgaatgg cttcaggagg  2100
cagcccgcca cacgaaaaaa ggttctcttc attttcatct gaaggtcgat acggggatga  2160
acagacttgg tgtaaaaaca gaggaagaag ttcagaacgt gatggcaatt cttgaccgca  2220
accctcgttt aaagtgcaaa ggggtattta cccattttgc gacagcggat gaaaaagaaa  2280
gaggctattt cttaatgcag tttgagcgct ttaaagagct gattgctccg ctgccgttaa  2340
agaatctaat ggtccactgc gcgaacagcg ccgctggact ccggctgaaa aaaggctttt  2400
ttaatgcagt cagattcggc atcggcatgt atggccttcg cccgtctgct gacatgtcgg  2460
acgagatacc gtttcagctg cgtccggcat ttaccctgca ttcgacactg tcacatgtca  2520
aactgatcag aaaaggcgag agcgtcagct acggagccga gtacacagcg gaaaaagaca  2580
catggatcgg gacggtgcct gtaggctatg cggacggctg gctccgaaaa ttgaaaggga  2640
ccgacatcct tgtgaaggga aaacgcctga aaattgccgg ccgaatttgc atggaccaat  2700
ttatggtgga gctggatcag gaatatccgc cgggcacaaa agtcacatta ataggccggc  2760
agggggatga atatatttcc atggatgaga ttgcaggaag gctcgaaacc attaactatg  2820
aggtggcctg tacaataagt tcccgtgttc cccgtatgtt tttggaaaat gggagtataa  2880
tggaagtaag aaatccttta ttgcaggtaa atataagcaa ttaacttacc taaatggaga  2940
attcaatcta ttattaatct gttcagcaat cgggcgcgat tgctgaataa aagatacgag  3000
agacctctct tgtatctttt ttattttgag tggttttgtc cgttacacta gaaaaccgaa  3060
agacaataaa aattttattc ttgctgagtc tggctttcgg taagctagac aaaacggaca  3120
aaataaaaat tggcaagggt ttaaaggtgg agatttttg agtgatcttc tcaaaaaata  3180
ctacctgtcc cttgctgatt tttaaacgag cacgagagca aaaccccccct ttgctgaggt  3240
ggcagagggc aggtttttt gtttcttttt tctcgtaaaa aaaagaaagg tcttaaaggt  3300
tttatggttt tggtcggcac tgccgacagc ctcgcagagc acacacttta tgaatataaa  3360
gtatagtgtg ttatacttta cttggaagtg gttgccggaa agagcgaaaa tgcctcacat  3420
ttgtgccacc taaaaaggag cgatttacat atgagttatg cagtttgtag aatgcaaaaa  3480
gtgaaatcat aatgataggt ggtatgtttt cgcttgaact tttaaataca gccattgaac  3540
atacggttga tttaataact gacaaacatc accctcttgc taaagcggcc aaggacgctg  3600
ccgccggggc tgtttgcgtt tttgccgtga tttcgtgtat cattggttta cttatttttt  3660
tgccaaagct gtaatggctg aaaattctta catttatatt tacattttta gaaatgggcg  3720
tgaaaaaaag cgcgcgatta tgtaaaatat aaagtgatag cggtaccatt ataggtagaa  3780
aggaggattc gaaatgaaac atggtatata ctacgcatat tgggaacaag aatgggaagc  3840
tgattacaaa tactatattg agaaggttgc aaagcttggt tttgatattc tagagattgc  3900
agcttcaccg ctaccttttt acagtgacat tcagattaat gagctcaagg catgtgccca  3960
tggcaatgga attacactta cggtaggcca tgggcctagt gcagaacaaa acctgtcttc  4020
tcccgacccc gatattcgca aaaatgctaa agctttttat accgatttac tcaaacgact  4080
ttacaagctg gatgtacatt tgataggtgg ggctttatat tcttattggc cgatagatta  4140
cacaaagaca attgataaaa aaggcgattg ggaacgcagc gttgaaagtg ttcgagaagt  4200
tgctaaggtg gccgaagcct gtggagtgga tttctgccta gaggttctta atagatttga  4260
gaattattta attaacacag cacaagaggg tgtagatttt gtaaaacagg ttgaccataa  4320
caatgtaaag gtaatgcttg ataccttcca catgaatatt gaggaagata gtatcggagg  4380
tgcaatcagg actgcgggct cttacttggg acatttacac actggcgaat gtaatcgtaa  4440
agttcccggc agaggaagaa ttccatgggt agaaattggt gaggctcttg ctgacatagg  4500
ttataacggt agtgttgtta tggaaccttt tgttagaatg ggcggaactg tcggatctaa  4560
tattaaggtt tggcgtgaca ttagtaacgg tgcagatgag aaaatgctgg atagagaagc  4620
acaggccgca cttgatttct ccagatatgt attagaatgt cataaacact cctaagaatt  4680
c                                                                  4681
```

```
SEQ ID NO: 17          moltype = DNA  length = 1170
FEATURE                Location/Qualifiers
source                 1..1170
                       mol_type = genomic DNA
                       organism = Bacillus subtilis
SEQUENCE: 17
atgagcacaa aacctttta cagagatacg tgggcggaaa ttgacttgtc cgcgataaag  60
gaaaatgtca gcaatatgaa aaaacatatc ggtgaacatg tccacttgat ggcagttgtg  120
aaagcaaacg cctacgggca tggtgatgca gaaacagcaa aggctgctct tgacgcaggt  180
gcttcatgct tggccgtggc cattttggat gaagcgattt cactgcgcaa aaagggattg  240
aaggcgccta tattggtgct tggcgcggtt cccccggagt atgtggcaat cgctgctgag  300
tatgacgtga ccttaacagg ttattctgtt gaatggcttc aggaggcagc ccgccacacg  360
aaaaaaggtt ctcttcattt tcatctgaag gtcgatacgg ggatgaacag acttggtgta  420
aaaacagagg aagaagttca gaacgtgatg gcaattcttg accgcaaccc tcgtttaaag  480
tgcaaagggg tatttaccca ttttgcgaca gcggatgaaa aagaaagagg ctatttctta  540
atgcagtttg agcgctttaa agagctgatt gctccgctgc cgttaaagaa tctaatggtc  600
cactgcgcga acagcgccgc tggactccgg ctgaaaaaag gcttttttaa tgcagtcaga  660
ttcggcatcg gcatgtatgg ccttcgcccg tctgctgaca tgtcggacga gataccgttt  720
cagctgcgtc cggcatttac cctgcattcg acactgtcac atgtcaaact gatcagaaaa  780
ggcgagagcg tcagctacgg agccgagtac acagcggaaa aagacacatg gatcgggacg  840
gtgcctgtag gctatgcgga cggctggctc cgaaaattga aagggaccga catccttgtg  900
aagggaaaac gcctgaaaat tgccggccga atttgcatgg accaatttat ggtggagctg  960
gatcaggaat atccgccggg cacaaaagtc acattaatag gccggcaggg ggatgaatat  1020
atttccatgg atgagattgc aggaaggctc gaaaccatta actatgaggt ggcctgtaca  1080
ataagttccc gtgttccccg tatgtttttg gaaaatggga gtataatgga agtaagaaat  1140
cctttattgc aggtaaatat aagcaattaa                                  1170

SEQ ID NO: 18          moltype = DNA  length = 1197
```

-continued

```
FEATURE                 Location/Qualifiers
source                  1..1197
                        mol_type = genomic DNA
                        organism = Bacillus subtilis
SEQUENCE: 18
gtgaaaaata aatggctgtc ttttttttcg ggtaaggtcc agcttgaatt gacgggaaga  60
gggattgagc ggctccttaa tgaatgcaca agacagggga ttccggtctt tcatgtcaaa  120
aaaaagaaag aagccgtatc gttatatata cagcttcagg atgtacatgc ctttcggcgg  180
gtaagaagta aatttaaatg taaagcccga tttatcaatc ggaagggatt tcccttcctg  240
ttgctgaaat caaagctgaa tatagggttt acgatcggtt ttgcgatttt tttcattctt  300
ttgtttttgc tgtccaatat ggtgtggaaa attgatgtga caggcgctaa gcctgaaaca  360
gaacatcaaa tgaggcagca tcttaatgaa atcggcgtca aaaagggccg tctgcagttt  420
ttaatgatgt cgcccgaaaa aatacagaaa tcattaacca atggaataga caatatcact  480
tgggtcggag ttgatctgaa ggggacgacc attcatatga aagttgtgga gaaaaatgag  540
cccgaaaaag aaaaatatgt tagcccgcgc aatattgtcg ccaaaaagaa agcaaccatt  600
acgagaatgt ttgtgcaaaa aggacagccc atggccgcca tacacgatca tgttgaaaag  660
ggacagctgc ttgtttcggg actgatcggc agcgaagacc atcagcagga agtcgcctca  720
aaagcagaaa tttatggaga aacctggtat agatcagaag tgacagtccc gcttgaaaca  780
ttatttaacg tctatacggg caaagtaagg acaaagcaca agctttcttt tggttctttg  840
gcaatcccga tctgggggat gacgtttaaa aaagaggaat tgaagcatcc aaaaacagaa  900
caagaaaagc attcgcttca ttttctcgga tttaagctcc ctgtatccta tgtcaaagag  960
caaacgagag aaagtgaaga ggctttgcga aaatatacaa aagaagaagc agttcaagaa  1020
ggcattaaat tgggtaaaca ggatgtagag gataaaatag gcgaaaacgg cgaggtgaaa  1080
agtgaaaaag ttttgcacca gactgttgag aatggtaaag taaagttgat tattctctac  1140
caagttatag aagatatcgt tcaaaccaca cctattgtca gggagactga agaatga     1197

SEQ ID NO: 19           moltype = DNA  length = 4579
FEATURE                 Location/Qualifiers
source                  1..4579
                        mol_type = genomic DNA
                        organism = Bacillus subtilis
SEQUENCE: 19
tgacaatatg tctcctgtca ttatgtcctt cacactctga tcaaacgtga ccagctgttt  60
ttcttccgtg aaattcatga caaaaatata atcattgtcc tgatcctgcc tcgcttgtac  120
ggagacgcct tttccgtgcc gaaccggaaa aactggagag agagacaggt ctgtgatcag  180
accctcatag aaatcacgct gaaattgatc ctccaaacgc gcgccgataa aatacgcctt  240
gccctgctga tactcatggc ttgtgaccgc tggcgtgcgc gcataaaaat cttcttgata  300
caccgcttcc actgaagctg tctttacatc aatcacggtt gcataatcct tcatttcata  360
tatttggctg cggtagctga cagcgtttcg atccttcgga tacagggtgt ccgtttcaag  420
aggctcaact ccaaatatag cttgaaatcg atatctctgc agtcgcgatg attaattaat  480
tcagaacgct cggttgccgc cgggcgtttt ttatgcagca atggcaagaa cgtcccgggg  540
agctcctaac ttataggggt aacacttaaa aaagaatcaa taacgataga aaccgctcct  600
aaagcaggtg catttttttcc taacgaagaa ggcaatagtt cacatttatt gtctaaatga  660
gaatggactc tagaagaaac ttcgttttta atcgtattta aaacaatggg atgagattca  720
attatatgat ttctcaagat aacagcttct atatcaaatg tattaaggat attggttaat  780
ccaattccga tataaaagcc aaagttttga agtgcattta acatttctac atcattttta  840
tttgcgcgtt ccacaatctc ttttcgagaa atattctttt cttctttaga gagcgaagcc  900
agtaacgctt tttcagaagc atataattcc caacagcctc gatttccaca gctgcatttg  960
ggtccattaa aatctatcgt catatgaccc atttccccag aaaaaccctg aacaccttta  1020
tacaattcgt tgttaataac aagtccagtt ccaattccga tattaatact gatgtaaacg  1080
atgttttcat agttttttgt cataccaaat actttttcac cgtatgctcc tgcattagct  1140
tcattttcaa caaaaaccgg aacattaaac tcactctcaa ttaaaaactg caaatctttg  1200
atattccaat ttaagttagg catgaaaata atttgctgat gacgatctac aaggcctgga  1260
acacaaattc ctattccgac tagaccataa ggggactcag gcatatgggt tacaaaacca  1320
tgaataagtg caaataaaat ctcttttact tcactagcgg aagaactaga caagtcagaa  1380
gtcttctcga gaataatatt tccttctaag tcggttagaa ttccgttaag atagtcgact  1440
cctatatcaa taccaatcga gtagcctgca ttcttattaa aaacaagcat tacaggtctt  1500
ctgccgcctc tagattgccc tgccccaatt tcaaaaataa aatctttttc aagcagtgta  1560
tttacttgag aggagacagt agacttgttt aatcctgtaa tctcagagag agttgccctg  1620
gagacagggg agttcttcaa aatttcatct aatattaatt tttgattcat tttttttact  1680
aaagcttgat ctgcaatttg aataataacc actcctttgt ttatccaccg aactaagttg  1740
gtgttttttg aagcttgaat tagatattta aaagtatcat atctaatatt ataactaaat  1800
tttctaaaaa aaacattgaa ataaacattt attttgtata tgatgagata aagttagttt  1860
attggataaa caaactaact caattaagat agttgatgga taaacttgtt cacttaaatc  1920
aaagggggaa atgacaaatg gtccaaacta gtgatatcta aaaatcaaag ggggaaatgg  1980
gatccaaagg aggccataat atgagtcaga aaacagacgc acctttagaa tcgtatgaag  2040
tgaacggcgc aacaattgcc gtgctgccag aagaaataga cggcaaaatc tgttccaaaa  2100
ttattgaaaa agattgcgtg ttttatgtaa acatgaagcc gctgcaaatt gtcgacagaa  2160
gctgccgatt ttttggatca agctatgcgg gaagaaaagc aggaacttat gaagtgacaa  2220
aaatttcaca caagccgccg atcatggtgg acccttcgaa ccaaatcttt ttattcccta  2280
cactttcttc gacaagaccc caatgcggct ggatttccca tgtgcatgta aaagaattca  2340
aagcgactga attcgacgat acggaagtga cgttttccaa tgggaaaacg atggagctgc  2400
cgatctctta taattcgttc gagaaccagg tataccgaac agcgtggctc agaaccaaat  2460
tccaagacag aatcgaccac cgcgtgccga aaagacagga atttatgctg tacccgaaag  2520
aagagcggac gaagatgatt tatgatttta ttttgcgtga gctcggggaa cggtattaga  2580
aaaatagccg cgggcggccg cactcttcct ttttcaatat tattgaagca tttatcaggg  2640
ttattgtctc atgagcggat acatatttga atgtatttag aaaaataaac aaataggggt  2700
tccgcgcaca tttccccgaa aagtgccacc tgacgtctaa gaaaccatta ttatcatgac  2760
attaacctat aaaaataggc gtatcacgag gccctttcgt cttcaagaat tgatcctcta  2820
```

-continued

```
gcacaaaaag aaaaacgaaa tgatacacca atcagtgcaa aaaaagatat aatgggagat  2880
aagacggttc gtgttcgtgc tgacttgcac catatcataa aaatcgaaac agcaaagaat  2940
ggcggaaacg taaaagaagt tatggaaata agacttagaa gcaaacttaa gagtgtgttg  3000
atagtgcagt atcttaaaat tttgtataat aggaattgaa gttaaattag atgctaaaaa  3060
tttgtaatta agaaggagtg attacatgaa caaaaatata aaatattctc aaaacttttt  3120
aacgagtgaa aaagtactca accaaataat aaaacaattg aatttaaaag aaaccgatac  3180
cgtttacgaa attggaacag gtaaagggca tttaacgacg aaactggcta aaataagtaa  3240
acaggtaacg tctattgaat tagacagtca tctattcaac ttatcgtcag aaaaattaaa  3300
actgaatact cgtgtcactt taattcacca agatattcta cagtttcaat tccctaacaa  3360
acagaggtat aaaattgttg ggagtattcc ttaccattta agcacacaaa ttattaaaaa  3420
agtggttttt gaaagccatg cgtctgacat ctatctgatt gttgaagaag gattctacaa  3480
gcgtaccttg gatattcacc gaacactagg gttgctcttg cacactcaag tctcgattca  3540
gcaattgctt aagctgccag cggaatgctt tcatcctaaa ccaaaagtaa acagtgtctt  3600
aataaaactt acccgccata ccacagatgt tccagataaa tattggaagc tatatacgta  3660
ctttgtttca aaatgggtca atcgagaata tcgtcaactg tttactaaaa atcagtttca  3720
tcaagcaatg aaacacgcca aagtaaacaa tttaagtacc gttacttatg agcaagtatt  3780
gtctattttt aatagttatc tattatttaa cgggaggaaa taattctatg agtcgctttt  3840
gtaaatttgg aaagttacac gttactaaag ggaatgtaga taaattatta ggtatactac  3900
tgacagcttc caaggagcta aagaggtccc tagactctag acccggggat ctctgcagtc  3960
gggaagatct ggtaatgact ctctagcttg aggcatcaaa taaaacgaaa ggctcagtcg  4020
aaagactggg cctttcgttt tatctgttgt ttgtcggtga acgctctcct gagtaggaca  4080
aatccgccgc tctagctaag cagaaggcca tcctgacgga tggccttttt gcgtttctac  4140
aaactcttgt taactctaga gctgcctgcc gcgtttcggt gatgaagatc ttcccgatga  4200
ttaattaatt cagaacgctc ggttgccgcc gggcgttttt tatgcagcaa tggcaagaac  4260
gttgctctag agcggccgca tcgattcaca gtggcaatct cccccgtatt cgtttgaaat  4320
gtgccacatt aacagcgccg ggtgatgtcc gtatcgttct gctaataagc ggttgatgtg  4380
ccgtgttttt tctcggtaga ctttagatgt gaggcagtgg ttgtgccttc cgccgtgcag  4440
ctgtttgacg cgggaggcat tgacgcgcaa aacttccgga taggtttgcg acagccaggc  4500
cggacgggct ccgctcggcg ttgctaatat gacccggccg cctatactgt gaatccgctc  4560
aaaaatatca tccagccat                                              4579

SEQ ID NO: 20          moltype = DNA  length = 36
FEATURE                Location/Qualifiers
misc_feature           1..36
                       note = Primer
source                 1..36
                       mol_type = other DNA
                       organism = synthetic construct
SEQUENCE: 20
ttaccttctc tcttctaagt accgttcgta tagcat                           36

SEQ ID NO: 21          moltype = DNA  length = 36
FEATURE                Location/Qualifiers
misc_feature           1..36
                       note = Primer
source                 1..36
                       mol_type = other DNA
                       organism = synthetic construct
SEQUENCE: 21
caagcaaagc tgttttatct accgttcgta taatgt                           36

SEQ ID NO: 22          moltype = DNA  length = 27
FEATURE                Location/Qualifiers
misc_feature           1..27
                       note = Primer
source                 1..27
                       mol_type = other DNA
                       organism = synthetic construct
SEQUENCE: 22
tacaaagcaa aagcgaaaat gaccatc                                     27

SEQ ID NO: 23          moltype = DNA  length = 36
FEATURE                Location/Qualifiers
misc_feature           1..36
                       note = Primer
source                 1..36
                       mol_type = other DNA
                       organism = synthetic construct
SEQUENCE: 23
atgctatacg aacggtactt agaagagaga aggtaa                           36

SEQ ID NO: 24          moltype = DNA  length = 36
FEATURE                Location/Qualifiers
misc_feature           1..36
                       note = Primer
source                 1..36
                       mol_type = other DNA
                       organism = synthetic construct
SEQUENCE: 24
```

-continued

```
acattatacg aacggtagat aaaacagctt tgcttg                        36

SEQ ID NO: 25          moltype = DNA  length = 26
FEATURE                Location/Qualifiers
misc_feature           1..26
                       note = Primer
source                 1..26
                       mol_type = other DNA
                       organism = synthetic construct
SEQUENCE: 25
cagctgatag gattcttgct cgctta                                   26

SEQ ID NO: 26          moltype = DNA  length = 23
FEATURE                Location/Qualifiers
misc_feature           1..23
                       note = Primer
source                 1..23
                       mol_type = other DNA
                       organism = synthetic construct
SEQUENCE: 26
tgataggtgg tatgttttcg ctt                                      23

SEQ ID NO: 27          moltype = DNA  length = 36
FEATURE                Location/Qualifiers
misc_feature           1..36
                       note = Primer
source                 1..36
                       mol_type = other DNA
                       organism = synthetic construct
SEQUENCE: 27
ataaatacca tgcttcatgt gtacattcct ctctta                        36

SEQ ID NO: 28          moltype = DNA  length = 36
FEATURE                Location/Qualifiers
misc_feature           1..36
                       note = Primer
source                 1..36
                       mol_type = other DNA
                       organism = synthetic construct
SEQUENCE: 28
taagagagga atgtacacat gaaacatggt atatac                        36

SEQ ID NO: 29          moltype = DNA  length = 27
FEATURE                Location/Qualifiers
misc_feature           1..27
                       note = Primer
source                 1..27
                       mol_type = other DNA
                       organism = synthetic construct
SEQUENCE: 29
gaattcttag gagtgtttat gacattc                                  27

SEQ ID NO: 30          moltype = DNA  length = 50
FEATURE                Location/Qualifiers
misc_feature           1..50
                       note = Primer
source                 1..50
                       mol_type = other DNA
                       organism = synthetic construct
SEQUENCE: 30
tagaatgcaa aaagtgaaat cataatgata ggtggtatgt tttcgcttga         50

SEQ ID NO: 31          moltype = DNA  length = 50
FEATURE                Location/Qualifiers
misc_feature           1..50
                       note = Primer
source                 1..50
                       mol_type = other DNA
                       organism = synthetic construct
SEQUENCE: 31
cgtctgtacg ttccttaagg aattcttagg agtgtttatg acattctaat         50

SEQ ID NO: 32          moltype = DNA  length = 50
FEATURE                Location/Qualifiers
misc_feature           1..50
                       note = Primer
source                 1..50
                       mol_type = other DNA
                       organism = synthetic construct
```

```
SEQUENCE: 32
attagaatgt cataaacact cctaagaatt ccttaaggaa cgtacagacg            50

SEQ ID NO: 33          moltype = DNA  length = 47
FEATURE                Location/Qualifiers
misc_feature           1..47
                       note = Primer
source                 1..47
                       mol_type = other DNA
                       organism = synthetic construct
SEQUENCE: 33
tcaagcgaaa acataccacc tatcattatg atttcacttt ttgcatt               47

SEQ ID NO: 34          moltype = DNA  length = 50
FEATURE                Location/Qualifiers
misc_feature           1..50
                       note = Primer
source                 1..50
                       mol_type = other DNA
                       organism = synthetic construct
SEQUENCE: 34
aaatctaaaa ttatctgaaa agggaagatc tttctaaaga ggaaatggtg            50

SEQ ID NO: 35          moltype = DNA  length = 50
FEATURE                Location/Qualifiers
misc_feature           1..50
                       note = Primer
source                 1..50
                       mol_type = other DNA
                       organism = synthetic construct
SEQUENCE: 35
ttgctgaaca gattaataat agattgaatt ctccatttag gtaagttaat            50

SEQ ID NO: 36          moltype = DNA  length = 50
FEATURE                Location/Qualifiers
misc_feature           1..50
                       note = Primer
source                 1..50
                       mol_type = other DNA
                       organism = synthetic construct
SEQUENCE: 36
attaacttac ctaaatggag aattcaatct attattaatc tgttcagcaa            50

SEQ ID NO: 37          moltype = DNA  length = 50
FEATURE                Location/Qualifiers
misc_feature           1..50
                       note = Primer
source                 1..50
                       mol_type = other DNA
                       organism = synthetic construct
SEQUENCE: 37
caccatttcc tctttagaaa gatcttccct tttcagataa ttttagattt            50

SEQ ID NO: 38          moltype = DNA  length = 65
FEATURE                Location/Qualifiers
misc_feature           1..65
                       note = Synthetized 5'UTR of the DPEase
source                 1..65
                       mol_type = other DNA
                       organism = synthetic construct
SEQUENCE: 38
agcggtacca ttataggtaa gagaggaatg tacacatgaa acatggtata tactacgcat  60
attgg                                                              65

SEQ ID NO: 39          moltype = DNA  length = 65
FEATURE                Location/Qualifiers
misc_feature           1..65
                       note = Synthetized 5'UTR of the DPEase
source                 1..65
                       mol_type = other DNA
                       organism = synthetic construct
SEQUENCE: 39
agcggtacca ttataggtag aaaggaggat tacatatgaa acatggtata tactacgcat  60
attgg                                                              65

SEQ ID NO: 40          moltype = DNA  length = 65
FEATURE                Location/Qualifiers
misc_feature           1..65
                       note = Synthetized 5'UTR of the DPEase
```

-continued

```
source                  1..65
                        mol_type = other DNA
                        organism = synthetic construct
SEQUENCE: 40
agcggtacca ttataggtag aaaggaggat tcgaaatgaa acatggtata tactacgcat  60
attgg                                                              65

SEQ ID NO: 41           moltype = DNA  length = 16
FEATURE                 Location/Qualifiers
misc_feature            1..16
                        note = 5'UTR of the DPEase gene
source                  1..16
                        mol_type = other DNA
                        organism = synthetic construct
SEQUENCE: 41
agagaggaat gtacac                                                  16

SEQ ID NO: 42           moltype = DNA  length = 16
FEATURE                 Location/Qualifiers
misc_feature            1..16
                        note = 5'UTR of the DPEase gene
source                  1..16
                        mol_type = other DNA
                        organism = synthetic construct
SEQUENCE: 42
gaaaggagga ttcgaa                                                  16

SEQ ID NO: 43           moltype = DNA  length = 16
FEATURE                 Location/Qualifiers
misc_feature            1..16
                        note = 5'UTR of the DPEase gene
source                  1..16
                        mol_type = other DNA
                        organism = synthetic construct
SEQUENCE: 43
gaaaggagga ttatgg                                                  16

SEQ ID NO: 44           moltype = DNA  length = 16
FEATURE                 Location/Qualifiers
misc_feature            1..16
                        note = 5'UTR of the DPEase gene
source                  1..16
                        mol_type = other DNA
                        organism = synthetic construct
SEQUENCE: 44
gaaaggagga ttgtcg                                                  16

SEQ ID NO: 45           moltype = DNA  length = 16
FEATURE                 Location/Qualifiers
misc_feature            1..16
                        note = 5'UTR of the DPEase gene
source                  1..16
                        mol_type = other DNA
                        organism = synthetic construct
SEQUENCE: 45
gaaaggagga tttagt                                                  16

SEQ ID NO: 46           moltype = DNA  length = 16
FEATURE                 Location/Qualifiers
misc_feature            1..16
                        note = 5'UTR of the DPEase gene
source                  1..16
                        mol_type = other DNA
                        organism = synthetic construct
SEQUENCE: 46
gaaaggagga ttgagg                                                  16

SEQ ID NO: 47           moltype = DNA  length = 16
FEATURE                 Location/Qualifiers
misc_feature            1..16
                        note = 5'UTR of the DPEase gene
source                  1..16
                        mol_type = other DNA
                        organism = synthetic construct
SEQUENCE: 47
agaaaggagg attaaa                                                  16

SEQ ID NO: 48           moltype = DNA  length = 16
FEATURE                 Location/Qualifiers
```

-continued

```
misc_feature            1..16
                        note = 5'UTR of the DPEase gene
source                  1..16
                        mol_type = other DNA
                        organism = synthetic construct
SEQUENCE: 48
gaaaggagga tttcgt                                                16

SEQ ID NO: 49           moltype = DNA  length = 16
FEATURE                 Location/Qualifiers
misc_feature            1..16
                        note = 5'UTR of the DPEase gene
source                  1..16
                        mol_type = other DNA
                        organism = synthetic construct
SEQUENCE: 49
gaaaggagga tttttg                                                16
```

GENETICALLY MODIFIED BACILLUS SUBTILIS STRAIN, OPTIMIZED VECTORS, AND USES THEREOF

CROSS-REFERENCE TO RELATED APPLICATIONS

This is a Division of application Ser. No. 16/762,030 filed May 6, 2020, which in turn is a national stage entry of PCT/EP2018/080328 filed Nov. 6, 2018, which claims priority to EP 17306533.5 filed Nov. 6, 2017. The disclosure of the prior applications is hereby incorporated by reference herein in its entirety.

REFERENCE TO AN ELECTRONIC SEQUENCE LISTING

The present application contains a Sequence Listing that has been submitted electronically and is hereby incorporated by reference in its entirety. The electronic Sequence Listing is named Sequence_Listing_ST26, was created on Mar. 20, 2024, and is 86,798 bytes in size.

The present invention relates to a genetically modified *Bacillus subtilis* strain which has been transformed with an optimized vector, mainly for producing a D-psicose 3-epimerase.

D-psicose, also called D-allulose, is a rare sugar epimer of fructose. It can be found in nature but at very low concentrations like in edible mushrooms, in jackfruit, in wheat and in *Itea* plants.

At the opposite of fructose, the metabolism of psicose in humans is partly absorbed and metabolized in energy, and partly excreted unchanged in the urine and in the faeces.

D-psicose has a noncaloric nature, a sweet taste equivalent to sucrose, a positive effect on the reduction of the glycemic response, an antiobesity effect, and the like. It is then particularly useful for preventing lifestyle-related diseases, such as diabetes or obesity.

D-psicose is very difficult to chemically synthetize. Therefore, interconversion between D-fructose and D-psicose by epimerization using the enzymes named D-psicose 3-epimerases has been considered as an attractive way of D-psicose production.

In that purpose, it has been provided improved variants of D-psicose 3-epimerase which are weak-acid stable, thermostable, and which have higher catalysis efficiency and turnover for the substrate D-fructose (PCT/EP2014/068628). This international application also discloses a host cell (such as *Escherichia coli* or *Bacillus subtilis*) having a nucleic acid coding for the said improved variants of D-psicose 3-epimerase.

Another strategy has been to clone and express the D-psicose-3-epimerase from *Clostridium cellulolyticum* in *Escherichia coli* (Cloning, Expression, and Characterization of a D-psicose-3-epimerase from *Clostridium cellulolyticum* H10, Journal of Agricultural and Food Chemistry, 2011, 59, 7785-7792, Wanmeng Fu et al.).

It has also been disclosed the cloning and expression of D-psicose-3-epimerase from *Clostridium scindens* (ATCC 35704) in *Bacillus subtilis*. The selection of the recombinant strains of *Bacillus subtilis* which have been transformed with a plasmid expressing the gene coding for D-psicose-3-epimerase is based on D-alanine defective selection marker (CN104894047).

It is appeared however to the inventors of the present invention that these strategies were not appropriate for industrial application, notably because of the low activity of the enzyme expression systems in the strains of *Bacillus subtilis*.

Therefore, there is still a need for improved D-psicose-3-epimerase production, as well as a need for improved D-psicose production. The methods have to be appropriate for industrial application and cost-effective. The methods have also to comply with safety and environment regulations.

Thus, the present invention aims to provide a method for improving D-psicose-3-epimerase production, as well as a method for improving D-psicose production, which are appropriate for industrial application, cost-effective, and which comply with safety and environment regulations.

The present invention relies on the unexpected results of the inventors showing that for improving D-psicose-3-epimerase production, as well as D-psicose production, it was necessary (i) not only to develop an optimized strain of *Bacillus subtilis*, but also (ii) to develop an optimized vector for higher D-psicose-3-epimerase expression.

The present invention also relies on the unexpected results of the inventors relative to an optimized fermentation medium for higher D-psicose-3-epimerase expression.

The objects of the present invention are therefore an optimized *Bacillus subtilis* strain, an optimized nucleic acid molecule comprising a nucleic acid sequence coding for D-psicose 3-epimerase, an optimized recombinant expression vector, an optimized recombinant host cell, and uses thereof in a method for producing a D-psicose 3-epimerase and in a method for producing D-psicose. The methods of obtaining the optimized and recombinant *Bacillus subtilis* strains are also an object of the present invention, as well as the optimized fermentation medium.

In a first aspect, the present invention relates thus to a genetically modified *Bacillus subtilis* strain wherein the alanine racemase alrA gene is inactivated, and having at least a further gene inactivation chosen among the inactivation of the sporulation yqfD gene, and/or the inactivation of the erythromycin resistance EmR-comK gene cassette.

The term "*Bacillus subtilis* strain" according to the invention means any strains of bacteria belonging to the genus *Bacillus* and the species *subtilis*. Cells of these organisms are less than 1 μm wide, sporangia are not swollen, and spores are ellipsoidal. *Bacillus subtilis* can be identified by several methods, such as the one described in Biochemical Test and Identification of *Bacillus subtilis*, Aryal S. 2016. www.microbiologyinfo.com/biochemical-test-andidentification-of-*bacillus-subtilis*/. In an embodiment of the invention, the "*Bacillus subtilis* strain" is isolated and/or purified.

The term "alanine racemase alrA gene" according to the invention means the gene coding for the enzyme D-alanine racemase, such enzyme catalyzing the chemical reaction from L-alanine to D-alanine. The "alrA" gene is also named "dal" gene, and is represented by SEQ ID NO: 17. SEQ ID NO: 17 (1.17 kb DNA fragment) contains the entire alrA structural gene (coding the D-alanine racemase identified in GenBank, under the number CAB12271.1) and regulatory signals for its expression. Within a large part of the bacteria, D-alanine is an important component of the glycan subunits to form the cell wall (composed of peptidoglycans). Alanine is usually found as the L-stereoisomer in nature, making the conversion to D-alanine by the cytoplasmic D-alanine racemase (alrA) essential for cell growth. Lack of the enzyme leads to rapid cell lysis due to a failure in the initial step of peptidoglycan biosynthesis. According to the invention, the genetically modified *Bacillus subtilis* strain is intended to be transformed with a vector in which the D-alanine racemase gene has been inserted. Therefore a *Bacillus subtilis* strain, in which the alrA gene is deleted (meaning that the *Bacillus subtilis* is "D-alanine defective"), and which has been successfully transformed with the said vector is able to grow without D-alanine supplementation. The main advantage of this strategy is to provide direct selection for the recombinant *Bacillus subtilis* in complex media without antibiotics. Moreover, as the D-alanine racemase is involved in the cell wall metabolism, the loss of the activity leads to the cell lysis, preventing the accumulation of a population of *Bacillus subtilis* (cells) which have lost the vector. In the present invention, the terms "alrA gene", "dal gene", "alanine racemase gene", alanine racemase alrA gene and "D-alanine racemase gene" can be used instead of another.

The term "sporulation yqfD gene" according to the invention means the gene which acts during the stage IV of the endospore maturation. The exact function of this gene is unknown, but its inactivation/deletion leads to a complete sporulation abortion. This "yqfD gene" is represented by SEQ ID NO: 18. *Bacillus* genus bacteria are known to produce a dedicated, very resistant and non-reproductive structure to enter in a state of dormancy: the endospores. Bacterial endospores keeps all material the cell needs to recover a living cell when favorable conditions will appear. The endospores are the perfect dissemination factor for the strain and their formation is a serious risk for environmental and health contamination. It is important to have a strain wherein the endospore forming pathway is aborted, notably for *Bacillus* strain which are intended to be used for industrial application. Therefore, a *Bacillus subtilis* strain wherein the sporulation yqfD gene is deleted complies with safety and environment regulations. To determine if a strain is sporulation deficient, a heat treatment can be applied to the strain; if the strain can produce bright spores then the strain is not sporulation deficient, whereas if the strain cannot produce bright spores then the strain is sporulation deficient.

The term "erythromycin resistance EmR-comK gene cassette" means a cassette containing the EmR gene and the comK gene. Surprisingly, it has indeed been found by the inventors that some *Bacillus subtilis* strain are resistant to erythromycin. In the *Bacillus subtilis* strain of the present invention, the EmR-comK gene cassette is inactivated, notably removed. Then, the "deletion of erythromycin resistance EmR-comK gene cassette" means the "removal of erythromycin resistance EmR-comK gene cassette". The above-mentioned cassette is represented by SEQ ID NO: 19. To determine if a strain is resistant or sensitive to erythromycin, the following test can be applied: contacting the strain with high concentration of erythromycin (for example 5 μg/mL); if the strain is still able to cultivate then the strain is resistant to erythromycin, whereas if the strain is not able to cultivate then the strain is sensitive to erythromycin. Therefore, a *Bacillus subtilis* strain wherein the erythromycin resistance gene is deleted complies with safety and environment regulations.

In an embodiment, the present invention relates thus to a genetically modified *Bacillus subtilis* strain wherein the alanine racemase alrA gene represented by SEQ ID NO: 17 or a sequence having at least 80% of identity with SEQ ID NO: 17 is inactivated, and having at least a further gene inactivation chosen among the inactivation of the sporulation yqfD gene represented by SEQ ID NO: 18 or a sequence having at least 80% of identity with SEQ ID NO: 18, and/or the inactivation of the erythromycin resistance EmR-comK gene cassette represented by SEQ ID NO: 19 or a sequence having at least 80% of identity with SEQ ID NO: 19. The percentage of identity between two sequences (A) and (B) can be obtained by dividing the full number of identical amino acid residues aligned by the full number of residues contained in the longest sequence between the sequence (A) and (B). Said alignment of sequences can be carried out by well-known methods, for example using the algorithm for global alignment of Needleman Wunsch. The term "at least 80% of identity" means 80, 81, 82, 83, 84, 85, 86, 87, 88, 89, 90, 91, 92, 93, 94, 95, 96, 97, 98, 99 and 100% of identity, notably 90%, preferably 95% and even more preferably 99% with SEQ ID NO: 17, SEQ ID NO: 18 and SEQ ID NO: 19.

The term "inactivated" and "gene inactivation" according to the invention means that the gene is deleted or inactivated by one or several mutations. The mutagenesis may be site-directed and/or random. The mutagenesis can be insertion, deletion, substitution of one or several nucleotides. In a preferred embodiment, "inactivated" and "gene inactivation" means that the gene is deleted. In another preferred embodiment, it means that the locus is deleted. In a preferred embodiment, the gene(s) is/are knocked-out. Deletion of the gene can be achieved by any technics known from the skilled person, for example a gene can be knocked-out by the Cre-Lox system, by any other site-specific recombinase systems (for example FLP, Dre) or by analogous methods such as MazF based system (i.e. by using a MazF cassette).

In an embodiment, the genetically modified *Bacillus subtilis* strain is a strain wherein the alanine racemase alrA gene and the sporulation yqfD gene are inactivated, notably by a deletion of the genes. An example of such a *Bacillus subtilis* strain is the strain which has been deposited at the National Collection of Microorganisms Cultures on Oct. 18, 2017 under the accession number CNCM I-5252. This strain is called BsR4 in the example of the present invention.

In another embodiment, the genetically modified *Bacillus subtilis* strain is a strain wherein the alanine racemase alrA gene and the erythromycin resistance EmR-comK gene cassette are inactivated, notably by a deletion of the genes. An example of such a *Bacillus subtilis* strain is the strain which has been deposited at the National Collection of Microorganisms Cultures on Oct. 18, 2017 under the accession number CNCM I-5251. This strain is called BsR3 in the example of the present invention.

In another and preferred embodiment, the genetically modified *Bacillus subtilis* strain is a strain wherein the alanine racemase alrA gene, the erythromycin resistance EmR-comK gene cassette, and the sporulation yqfD gene are inactivated, notably by a deletion of the genes. An example of such a strain is the strain which has been deposited at the National Collection of Microorganisms Cultures on Oct. 18, 2017 under the accession number CNCM I-5253. This strain is called BsR5 in the example of the present invention.

The above-mentioned strains BsR3, BsR4 and BsR5 have been deposited at the National Collection of Microorganisms Cultures of the Pasteur Institute, located at Institut Pasteur, 25, 28 rue du Docteur Roux, 75724 Paris Cedex 15, France.

In a second aspect, the present invention relates to a method of obtaining a genetically modified *Bacillus subtilis* strain as mentioned above, comprising mutagenesis or genetic transformation of a *Bacillus subtilis* strain. Notably, such method allows obtaining the strains BsR3, BsR4 and BsR5.

The term "genetic transformation" according to the present invention means notably genes deletion.

In an embodiment, the present invention relates thus to a method of obtaining a *Bacillus subtilis* which is D-alanine defective ($alrA^-$) and erythromycin sensitive and/or sporulation deficient, preferably a *Bacillus subtilis* which is D-alanine defective ($alrA^-$) and erythromycin sensitive and sporulation deficient.

In an embodiment, the said method of obtaining a genetically modified *Bacillus subtilis* strain, notably the strain BsR4, comprises the following steps:

(a) the alanine racemase alrA gene is deleted in a *Bacillus subtilis*, preferably by a Cre/Lox system, in order to provide a D-alanine defective *Bacillus subtilis* (alrA-);

(b) the sporulation yqfD gene is deleted, preferably by using a MazF based system, in order to provide a *Bacillus subtilis* which is sporulation deficient, and D-alanine defective ($alrA^-$).

In this embodiment, the step (b) is preferably performed on *Bacillus subtilis* strain obtained in step (a). In an embodiment, the strain obtained in step (b) is erythromycin sensitive or erythromycin resistant, preferably erythromycin resistant.

A *Bacillus subtilis* which is sporulation deficient, and D-alanine defective ($alrA^-$) can be obtained, for example, as described in Example 3.2.a.

In another embodiment, the said method of obtaining a genetically modified *Bacillus subtilis* strain, notably the strain BsR3, comprises the following steps:

(a) the alanine racemase alrA gene is deleted in a *Bacillus subtilis*, preferably by a Cre/Lox system, in order to provide a D-alanine defective *Bacillus subtilis* (alrA-);

(b) the erythromycin resistance EmR-comK gene cassette is removed/deleted, preferably by using a MazF based system, in order to provide an erythromycin sensitive and a D-alanine defective *Bacillus subtilis* ($alrA^-$).

In this embodiment, the step (b) is preferably performed on *Bacillus subtilis* strain obtained in step (a). In an embodiment, the strain obtained in step (b) is sporulation deficient or sporulation efficient, preferably sporulation deficient.

A *Bacillus subtilis* which is erythromycin sensitive, and D-alanine defective ($alrA^-$) can be obtained, for example, as described in Example 3.1.

In a preferred and another embodiment, the said method of obtaining a genetically modified *Bacillus subtilis* strain, notably the strain BsR5, comprises the following steps:

(a) the alanine racemase alrA gene is deleted in a *Bacillus subtilis*, preferably by a Cre/Lox system, in order to provide a D-alanine defective *Bacillus subtilis* (alrA-);

(b) the erythromycin resistance EmR-comK gene cassette is removed/deleted, preferably by using a MazF based system, in order to provide an erythromycin sensitive and a D-alanine defective *Bacillus subtilis* ($alrA^-$);

(c) the sporulation yqfD gene is deleted, preferably by using a MazF based system, in order to provide a *Bacillus subtilis* which is erythromycin sensitive, sporulation deficient, and D-alanine defective ($alrA^-$).

A *Bacillus subtilis* which is erythromycin sensitive, sporulation deficient, and D-alanine defective ($alrA^-$) can be obtained, for example, as described in Example 3.2.b.

In this embodiment, the step (b) is preferably performed on *Bacillus subtilis* strain obtained in step (a) and the step (c) is preferably performed on *Bacillus subtilis* strain obtained in step (b). In another embodiment, the deletion of the sporulation yqfD gene can be performed before the deletion of the erythromycin resistance EmR-comK gene cassette.

In a third aspect, the present invention relates to an isolated nucleic acid molecule comprising a nucleic acid sequence coding for D-psicose 3-epimerase and a sequence comprising or consisting of SEQ ID NO: 1 or of SEQ ID NO: 2.

SEQ ID NO: 1 and SEQ ID NO: 2 correspond to sequence of optimized 5' untranslated region (5' UTR) for D-psicose 3-epimerase expression. Such sequences are upstream of the nucleic acid sequence coding for D-psicose 3-epimerase. In a preferred embodiment, SEQ ID NO: 1 or SEQ ID NO: 2 are directly upstream of the ATG codon of nucleic acid sequence coding for D-psicose 3-epimerase. In that embodiment, the last base of SEQ ID NO: 1 or SEQ ID NO: 2 is then followed by the first base of the ATG codon of nucleic acid sequence coding for D-psicose 3-epimerase. Sequences comprising or consisting of SEQ ID NO: 1 or of SEQ ID NO: 2 are operably linked to the nucleic acid sequence coding for D-psicose 3-epimerase. The term "operably linked" according to the invention means that sequences comprising or consisting of SEQ ID NO: 1 or of SEQ ID NO: 2 is attached or linked to the sequence coding for D-psicose 3-epimerase in such a manner as to allow these sequences comprising or consisting of SEQ ID NO: 1 or of SEQ ID NO: 2 to control the expression of D-psicose 3-epimerase. SEQ ID NO: 1 or SEQ ID NO: 2 are non-coding sequences, contrary to nucleic acid sequence coding for D-psicose 3-epimerase. More precisely, SEQ ID NO: 1 or SEQ ID NO: 2 are optimized ribosome binding sites.

The term "D-psicose 3-epimerase" or "DPEase" according to the invention refers to the ketose 3-epimerase whose D-psicose is the optimum substrate. It refers to an enzyme which has the ability to modify D-fructose into D-psicose.

In a preferred embodiment, the present invention relates to an isolated nucleic acid molecule comprising a nucleic acid sequence coding for D-psicose 3-epimerase and a sequence comprising or consisting of SEQ ID NO: 2.

In an embodiment, the nucleic acid sequence coding for D-psicose 3-epimerase is chosen among the nucleic acid of SEQ ID NO: 3, SEQ ID NO:4 or the nucleic acid coding for SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13, and is preferably SEQ ID NO: 4. SEQ ID NO: 5 to SEQ ID NO: 13 correspond to the nucleic acid coding for the optimized variants disclosed in PCT/EP2014/068628, i.e optimized variants having a serine residue at position 211.

The term "nucleic acid" according to the invention may be DNA or RNA. The term "DNA" includes cDNA, gDNA or artificially synthetized DNA. The DNA may be single strand or double strand. In a preferred embodiment, the nucleic acid of the present invention is DNA. It will be understood that as a result of the degeneracy of the genetic code, a multitude of nucleotide sequences may code a given protein. In an embodiment, the said nucleic acid molecule is artificial.

According to the present invention, the nucleic acid coding for D-psicose 3-epimerase can be present in the host cell as an episomic sequence or can be incorporated into its chromosome. The nucleic acid coding for D-psicose 3-epimerase can also be present in the host cell in one copy or in several copies.

The present invention also relates to an expression cassette of a nucleic acid molecule as mentioned above. In that embodiment, this expression cassette comprises all elements required for expression of D-psicose 3-epimerase, in particular all the elements required for transcription and translation in the host cell.

In a fourth aspect, the present invention relates to a recombinant expression vector comprising a nucleic acid molecule as mentioned above, or an expression cassette of a nucleic acid molecule as mentioned above. In another embodiment, the said recombinant expression vector comprises or consists of SEQ ID NO: 14, SEQ ID NO: 15 or SEQ ID NO: 16.

The term "a recombinant expression vector" means a vector which comprises the elements required/necessary for its expression, namely which allows expressing the D-psicose 3-epimerase in the host cell. Preferably the vector is a self-replicable vector. In particular, the vector or the expression cassette also comprises a promoter sequence (for example the promotor P43), a terminator sequence and optionally an enhancer.

A "vector" according to the invention can be a plasmid, a phage, a phagemid, a cosmid, a virus, YAC, BAC, . . . . In a preferred embodiment the vector is a plasmid. In a preferred embodiment, the vector is an integration vector suitable to incorporate the sequence coding for D-psicose 3-epimerase into the chromosome of the host cell. More preferably, the recombinant expression vector of the invention comprises or consists of SEQ ID NO: 16.

In a fifth aspect, the present invention relates to a recombinant host cell comprising a nucleic acid as above-mentioned, or a recombinant expression vector as above-mentioned.

The term "host cell" according to the invention can be a prokaryote or a eukaryote host cell. In a particular embodiment, the host cell is a GRAS (Generally Recognized As Safe) strain, more preferably *Bacillus subtilis* strain. In a preferred embodiment, the host cell is a genetically modified *Bacillus subtilis* strain as defined above.

In an embodiment, the cell is non-human and non-embryonic.

In an embodiment, the host cell is cultured under conditions such that the D-psicose 3-epimerase is expressed by the host cell. In a preferred embodiment, the D-psicose 3-epimerase is recovered from the culture media.

In a preferred embodiment, the present invention relates to a recombinant host cell comprising a recombinant expression vector comprising or consisting of SEQ ID NO: 16.

In an embodiment, the host cell is a genetically modified *Bacillus subtilis* strain deposited at the National Collection of Microorganisms Cultures on Oct. 18, 2017 under the Number CNCM I-5251 which comprises a nucleic acid comprising or consisting of SEQ ID NO: 14. This refers to the strain called BsR3 which has been transformed with the plasmid called pR1.

In another embodiment, the host cell is a genetically modified *Bacillus subtilis* strain deposited at the National Collection of Microorganisms Cultures on Oct. 18, 2017 under the Number CNCM I-5251 which comprises a nucleic acid comprising or consisting of SEQ ID NO: 15. This refers to the strain called BsR3 which has been transformed with the plasmid called pR2.

In another embodiment, the host cell is a genetically modified *Bacillus subtilis* strain deposited at the National Collection of Microorganisms Cultures on Oct. 18, 2017 under the Number CNCM I-5251 which comprises a nucleic acid comprising or consisting of SEQ ID NO: 16. This refers to the strain called BsR3 which has been transformed with the plasmid called pR3.

In another embodiment, the host cell is a genetically modified *Bacillus subtilis* strain deposited at the National Collection of Microorganisms Cultures on Oct. 18, 2017 under the Number CNCM I-5252 which comprises a nucleic acid comprising or consisting of SEQ ID NO: 14. This refers to the strain called BsR4 which has been transformed with the plasmid called pR1.

In another embodiment, the host cell is a genetically modified *Bacillus subtilis* strain deposited at the National Collection of Microorganisms Cultures on Oct. 18, 2017 under the Number CNCM I-5252 which comprises a nucleic acid comprising or consisting of SEQ ID NO: 15. This refers to the strain called BsR4 which has been transformed with the plasmid called pR2.

In another embodiment, the host cell is a genetically modified *Bacillus subtilis* strain deposited at the National Collection of Microorganisms Cultures on Oct. 18, 2017 under the Number CNCM I-5252 which comprises a nucleic acid comprising or consisting of SEQ ID NO: 16. This refers to the strain called BsR4 which has been transformed with the plasmid called pR3.

In another embodiment, the host cell is a genetically modified *Bacillus subtilis* strain deposited at the National Collection of Microorganisms Cultures on Oct. 18, 2017 under the Number CNCM I-5253 which comprises a nucleic acid comprising or consisting of SEQ ID NO: 14. This refers to the strain called BsR5 which has been transformed with the plasmid called pR1.

In another embodiment, the host cell is a genetically modified *Bacillus subtilis* strain deposited at the National Collection of Microorganisms Cultures on Oct. 18, 2017 under the Number CNCM I-5253 which comprises a nucleic acid comprising or consisting of SEQ ID NO: 15. This refers to the strain called BsR5 which has been transformed with the plasmid called pR2.

In another and preferred embodiment, the host cell is a genetically modified *Bacillus subtilis* strain deposited at the National Collection of Microorganisms Cultures on Oct. 18, 2017 under the Number CNCM I-5253 which comprises a nucleic acid comprising or consisting of SEQ ID NO: 16. This refers to the strain called BsR5 which has been transformed with the plasmid called pR3.

The term "a host cell which is a genetically modified *Bacillus subtilis* strain and which comprises a nucleic acid" means that the said genetically modified *Bacillus subtilis* strain has been transformed with a nucleic acid or with a vector comprising a nucleic acid. As used herein, the terms "transformed" can means "stably transformed" and refers to a cell into which a nucleotide sequence has been introduced by human intervention. The term "transform" or "transforming" or "transformed" can also be understood by meaning "modification" or "modifying" or "modified"; but also meaning "transfection" or "transfecting" or "transfected" and "transduction" or "transducing" or "transduced" according to the used vector.

In a sixth aspect, the present invention relates to a method of obtaining a recombinant *Bacillus subtilis* expressing D-psicose 3-epimerase, as mentioned above, comprises the following steps:

(a) obtaining a genetically modified *Bacillus subtilis* strain wherein the alanine racemase alrA gene is inactivated, and having at least a further gene inactivation chosen among the inactivation of the sporulation yqfD gene, and/or the inactivation of the erythromycin resistance EmR-comK gene cassette;

(b) transforming the said genetically modified *Bacillus subtilis* obtained in step (a) with a vector comprising a nucleic acid molecule comprising a nucleic acid sequence coding for D-psicose 3-epimerase and a sequence comprising or consisting of SEQ ID NO: 1 or of SEQ ID NO: 2.

In an embodiment, the method of obtaining a recombinant *Bacillus subtilis* expressing D-psicose 3-epimerase, as mentioned above, comprises the following steps:

(a) obtaining a genetically modified *Bacillus subtilis* strain wherein the alanine racemase alrA gene and the sporulation yqfD gene are inactivated;

(b) transforming the said genetically modified *Bacillus subtilis* obtained in step (a) with a vector comprising a nucleic acid molecule comprising a nucleic acid sequence coding for D-psicose 3-epimerase and a sequence comprising or consisting of SEQ ID NO: 1 or of SEQ ID NO: 2.

In an embodiment, the method of obtaining a recombinant *Bacillus subtilis* expressing D-psicose 3-epimerase, as mentioned above, comprises the following steps:

(a) obtaining a genetically modified *Bacillus subtilis* strain wherein the alanine racemase alrA gene and the erythromycin resistance EmR-comK gene cassette are inactivated;

(b) transforming the said genetically modified *Bacillus subtilis* obtained in step (a) with a vector comprising a nucleic acid molecule comprising a nucleic acid sequence coding for D-psicose 3-epimerase and a sequence comprising or consisting of SEQ ID NO: 1 or of SEQ ID NO: 2.

In a preferred embodiment, the method of obtaining a recombinant *Bacillus subtilis* expressing D-psicose 3-epimerase, as mentioned above, comprises the following steps:

(a) obtaining a genetically modified *Bacillus subtilis* strain wherein the alanine racemase alrA gene, the erythromycin resistance EmR-comK gene cassette, and the sporulation yqfD gene are inactivated;

(b) transforming the said genetically modified *Bacillus subtilis* obtained in step (a) with a vector comprising a nucleic acid molecule comprising a nucleic acid sequence coding for D-psicose 3-epimerase and a sequence comprising or consisting of SEQ ID NO: 1 or of SEQ ID NO: 2.

In a preferred embodiment, the method of obtaining a recombinant *Bacillus subtilis* expressing D-psicose 3-epimerase, as mentioned above, comprises the following steps:

(a) obtaining a genetically modified *Bacillus subtilis* strain wherein the alanine racemase alrA gene, the erythromycin resistance EmR-comK gene cassette, and the sporulation yqfD gene are inactivated;

(b) transforming the said genetically modified *Bacillus subtilis* obtained in step (a) with a vector comprising or consisting of SEQ ID NO: 16.

In a preferred embodiment, the method of obtaining a recombinant *Bacillus subtilis* expressing D-psicose 3-epimerase, as mentioned above, comprises the following steps:

(a) deleting the alanine racemase alrA gene in a *Bacillus subtilis*, preferably by a Cre/Lox system, in order to provide a D-alanine defective *Bacillus subtilis* (alrA-);

(b) deleting the erythromycin resistance EmR-comK gene cassette in the *Bacillus subtilis* strain obtained in step (a), preferably by using a MazF based system, in order to provide an erythromycin sensitive and a D-alanine defective *Bacillus subtilis* ($alrA^-$);

(c) deleting the sporulation yqfD gene in the *Bacillus subtilis* strain obtained in step (b), preferably by using a MazF based system, in order to provide a *Bacillus subtilis* which is erythromycin sensitive, sporulation deficient, and D-alanine defective ($alrA^-$);

(d) transforming the said genetically modified *Bacillus subtilis* obtained in step (c) with a vector comprising or consisting of SEQ ID NO: 16.

In a seventh aspect, the present invention relates to a method for producing a D-psicose 3-epimerase, notably by a fermentation process, comprising culturing the recombinant host cell as mentioned above, and optionally recovering the produced D-psicose 3-epimerase from the resulting culture.

The present invention also relates to the use of a nucleic acid, an expression cassette, an expression vector, or a host cell as mentioned above for producing a D-psicose 3-epimerase according to the present invention.

In an embodiment, such method for producing a D-psicose 3-epimerase comprises the following steps:

culturing the recombinant host cell as mentioned above in a suitable culture medium comprising a sugar concentration of at least 60 g/L, notably 60 g/L;

and optionally recovering the produced D-psicose 3-epimerase from the resulting culture.

In an embodiment, the suitable culture medium is a suitable fermentation medium.

In a preferred embodiment, the sugar is the glucose. The inventors of the present invention have also surprisingly found that the use of a glucose concentration of about 60 g/L is an optimized concentration for the production of D-psicose 3-epimerase according to the present invention. This quantity is particularly adapted for a batch of 20 L, and will be adapted if necessary for other batches. Other components of suitable medium will be apparent to skilled person. For example an appropriate medium can also comprises yeast, $KH_2PO_4$, $MgSO_4$, $2H_2O$, $MnSO_4$, $H_2O$, . . . . Advantageously, a culture medium contains a carbon source (such as glucose), a nitrogen source (such as yeast, yeast extract(s) or amino acids), salts (such as ammonium sulfate, micronutrients (such as iron and magnesium salt), and organic vitamins if necessary. Other specific culture conditions, such as temperature, pH and the like, may be those that are used for the host cell selected for expression, and will be apparent to skilled person. For example, the temperature may be above 30° C. (notably 36.5-37.5° C.) and pH around 6.

In a preferred embodiment, culturing is carried out in batch culture.

In a preferred embodiment, the host cell used in the method for producing a D-psicose 3-epimerase is the genetically modified *Bacillus subtilis* strain deposited at the National Collection of Microorganisms Cultures on Oct. 18, 2017 under the Number CNCM I-5253 which comprises a nucleic acid comprising or consisting of SEQ ID NO: 16 (i.e. the strain called BsR5 which has been transformed with the plasmid called pR3).

In an eighth aspect, the present invention relates to the use of a D-psicose 3-epimerase obtained according to the present invention for producing D-psicose.

In an embodiment, the present invention relates to a method for producing a D-psicose comprising:

(a) culturing the recombinant host cell as defined above;

(b) recovering the produced D-psicose 3-epimerase from the resulting culture;

(c) contacting the D-psicose 3-epimerase obtained in step (b) with D-fructose in conditions suitable for D-psicose 3-epimerase activity; and (d) optionally recovering the produced D-psicose.

In a preferred embodiment, the recombinant host cell used in the method for producing a D-psicose is the genetically modified *Bacillus subtilis* strain deposited at the National Collection of Microorganisms Cultures on Oct. 18, 2017 under the Number CNCM I-5253 which comprises a nucleic acid comprising or consisting of SEQ ID NO: 16 (i.e. the strain called BsR5 which has been transformed with the plasmid called pR3).

Suitable conditions for producing D-psicose can be defined by the skilled person.

The Table 1 below mentions the sequences used in the present invention.

| Sequence number | Sequences |
| --- | --- |
| SEQ ID NO: 1, optimized ribosome binding sites | AGAAAGGAGGATTACAT |
| SEQ ID NO: 2, optimized translation initiation region | AGAAAGGAGGATTCGAA |
| SEQ ID NO: 3, nucleic acid coding for DPEase H10 from literature | ATGAAACATGGTATATACTACGCATATTGGGAACAAGAATGGGAAGCTGATT<br>ACAAATACTATATTGAGAAGGTTGCAAAGCTTGGTTTTGATATTCTAGAGAT<br>TGCAGCTTCACCGCTACCTTTTTACAGTGACATTCAGATTAATGAGCTCAAG<br>GCATGTGCCCATGGCAATGGAATTACACTTACGGTAGGCCATGGGCCTAGTG<br>CAGAACAAAACCTGTCTTCTCCCGACCCCGATATTCGCAAAAATGCTAAAGC<br>TTTTTATACCGATTTACTCAAACGACTTTACAAGCTGGATGTACATTTGATAG<br>GTGGGGCTTTATATTCTTATTGGCCGATAGATTACACAAAGACAATTGATAA<br>AAAAGGCGATTGGGAACGCAGCGTTGAAAGTGTTCGAGAAGTTGCTAAGGT<br>GGCCGAAGCCTGTGGAGTGGATTTCTGCCTAGAGGTTCTTAATAGATTTGAG<br>AATTATTTAATTAACACAGCACAAGAGGGTGTAGATTTTGTAAAACAGGTTG<br>ACCATAACAATGTAAAGGTAATGCTTGATACCTTCCATATGAATATTGAGGA<br>AGATAGTATCGGAGGTGCAATCAGGACTGCGGGCTCTTACTTGGGACATTTA<br>CACACTGGCGAATGTAATCGTAAAGTTCCCGGCAGAGGAAGAATTCCATGG<br>GTAGAAATTGGTGAGGCTCTTGCTGACATAGGTTATAACGGTAGTGTTGTTA<br>TGGAACCTTTTGTTAGAATGGGCGGAACTGTCGGATCTAATATTAAGGTTTG<br>GCGTGACATTAGTAACGGTGCAGATGAGAAAATGCTGGATAGAGAAGCACA<br>GGCCGCACTTGATTTCTCCAGATATGTATTAGAATGTCATAAACACTCCTGA |
| SEQ ID NO: 4, nucleic acid coding for DPEase H10 de novo synthetized | CATATGAAACATGGTATATACTACGCATATTGGGAACAAGAATGGGAAGCT<br>GATTACAAATACTATATTGAGAAGGTTGCAAAGCTTGGTTTTGATATTCTAG<br>AGATTGCAGCTTCACCGCTACCTTTTTACAGTGACATTCAGATTAATGAGCTC<br>AAGGCATGTGCCCATGGCAATGGAATTACACTTACGGTAGGCCATGGGCCTA<br>GTGCAGAACAAAACCTGTCTTCTCCCGACCCCGATATTCGCAAAAATGCTAA<br>AGCTTTTTATACCGATTTACTCAAACGACTTTACAAGCTGGATGTACATTTGA<br>TAGGTGGGGCTTTATATTCTTATTGGCCGATAGATTACACAAAGACAATTGA<br>TAAAAAAGGCGATTGGGAACGCAGCGTTGAAAGTGTTCGAGAAGTTGCTAA<br>GGTGGCCGAAGCCTGTGGAGTGGATTTCTGCCTAGAGGTTCTTAATAGATTT<br>GAGAATTATTTAATTAACACAGCACAAGAGGGTGTAGATTTTGTAAAACAGG<br>TTGACCATAACAATGTAAAGGTAATGCTTGATACCTTCCACATGAATATTGA<br>GGAAGATAGTATCGGAGGTGCAATCAGGACTGCGGGCTCTTACTTGGGACAT<br>TTACACACTGGCGAATGTAATCGTAAAGTTCCCGGCAGAGGAAGAATTCCAT<br>GGGTAGAAATTGGTGAGGCTCTTGCTGACATAGGTTATAACGGTAGTGTTGT<br>TATGGAACCTTTTGTTAGAATGGGCGGAACTGTCGGATCTAATATTAAGGTT<br>TGGCGTGACATTAGTAACGGTGCAGATGAGAAAATGCTGGATAGAGAAGCA<br>CAGGCCGCACTTGATTTCTCCAGATATGTATTAGAATGTCATAAACACTCCCT<br>CGAG<br>Underlined zones are the slight modifications, in comparison with SEQ ID NO: 3 (insertion for the restriction sites for NdeI/XhoI and the mutation T558C |
| SEQ ID NO: 5, which corresponds to the sequence of SEQ ID NO: 2 (having a serine residue at position 211) of PCT/EP2014/068628 | MKHGIYYAYWEQEWEADYKYYIEKVAKLGFDILEIAASPLPFYSDIQINELKAC<br>AHGNGITLTVGHGPSAEQNLSSPDPDIRKNAKAFYTDLLKRLYKLDVHLIGGAL<br>YSYWPIDYTKTIDKKGDWERSVESVREVAKVAEACGVDFCLEVLNRFENYLINT<br>AQEGVDFVKQVDHNNVKVMLDTFHMNIEEDSIGGAIRTAGSYLGHLHTSECNR<br>KVPGRGRIPWVEIGEALADIGYNGSVVMEPFVRMGGTVGSNIKVWRDISNGAD<br>EKMLDREAQAALDFSRYVLECHKHS |
| SEQ ID NO: 6, which corresponds to the sequence of SEQ ID NO: 4 (having a serine residue at position 211) of PCT/EP2014/068628 | MKHGIYYAYWEQEWEADYKYYIEKVAKLGFDILEIAASPLPFYSDIQINELKAC<br>AHGNGITLTVGHGPSAEQNLSSPDPDIRKNAKAFYTDLLKRLYKLDVHLIGGAL<br>YSYWPIDYTKTIDKKGDWERSVESVREVAKVAEACGVDFCLEVLNRFENYLINT<br>AQEGVDFVKQVDHNNVKVMLDTFHMNIEEDSIGGAIRTAGSYLGHLHTSECNR<br>KVPGRGRIPWVEIGEALADIGYNGSVVMEPFVRMGGTVGSNIKVWRDISNGAD<br>EKMLDREAQAALDFSRYVLECHKHS |
| SEQ ID NO: 7, which corresponds to the sequence of SEQ ID NO: 5 (having a serine residue at position 211) of PCT/EP2014/068628 | MKHGIYYAYWEQEWEADYKYYIEKVAKLGFDILEIAASPLPFYSDNQINELKAC<br>ARGNGITLTVGHGPSAEQNLSSPDPYIRKNAKAFYTDLLKRLYKLDVHLIGGAIY<br>SYWPVDYTKTIDKKGDWERSVESVREVAQVAEACGVDFCLEVLNRFENYLINT<br>AQEGVDFVKQVGHDNVKVMLDTFHMNIEEDSIGGAIRTAGSYLGHLHTSECNR<br>KVPGKGRIPWIEIGEALADIGYNGSVVMEPFVRMGGTVGSNIKVWRDISNGADE<br>EKLDREAQAALNFSRYVLGNRKL |
| SEQ ID NO: 8, which corresponds to the sequence of SEQ ID NO: 6 (having a serine residue at position 211) of PCT/EP2014/068628 | MKHGIYYAYWEQEWAADYKRYVEKAAKLGFDILEVGAAPLPDYSAQEVKELK<br>KCADDNGIQLTAGYGPAFNHNMGSSDPKIREEALQWYKRLFEVMAGLDIHLIG<br>GALYSYWPVDFATANKEEDWKHSVEGMQILAPIASQYGINLGMEVLNRFESHIL<br>NTSEEGVKFVTEVGMDNVKVMLDTFHMNIEESSIGDAIRHAGKLLGHFHTSECN<br>RMVPGKGRTPWREIGDALREIEYDGTVVMEPFVRMGGQVGSDIKVWRDISKGA<br>GEDRLDEDARRAVEFQRYMLEWK |
| SEQ ID NO: 9, which corresponds to the sequence of SEQ ID NO: 7 (having a serine residue at position 211) of PCT/EP2014/068628 | MKHGIYYSYWEHEWSAKFGPYIEKVAKLGFDIIEVAAHHINEYSDAELATIRKS<br>AKDNGIILTAGIGPSKTKNLSSEDAAVRAAGKAFFERTLSNVAKLDIHTIGGALH<br>SYWPIDYSQPVDKAGDYARGVEGINGIADFANDLGINLCIEVLNRFENHVLNTA<br>AEGVAFVKDVGKNNVKVMLDTFHMNIEEDSFGDAIRTAGPLLGHFHTSESNRR<br>VPGKGRMPWHEIGLALRDINYTGAVIMEPFVKTGGTIGSDIKVWRDLSGGADIA<br>KMDEDARNALAFSRFVLG |

-continued

| Sequence number | Sequences |
|---|---|
| SEQ ID NO: 10, which corresponds to the sequence of SEQ ID NO: 8 (having a serine residue at position 211) of PCT/EP2014/068628 | MKYGIYYAYWEKEWNGDYKYYIDKISKLGFDILEISCGAFSDYYTKDQELIDIG<br>KYAKEKGVTLTAGYGPHFNESLSSSEPNTQKQAISFWKETLRKLKLMDIHIVGG<br>ALYGYWPVDYSKPFDKKRDLENSIKNMKIISQYAEEYDIMMGMEVLNRFEGYM<br>LNTCDEALAYVEEVGSSNVGVMLDTFHMNIEEDNIAAAIRKAGDRLYHFHISEG<br>NRKVPGKGMLPWNEIGQALRDINYQHAAVMEPFVMQGGTVGHDIKIWRDIIGN<br>CSEVTLDMDAQSALHFVKHVFEV |
| SEQ ID NO: 11, which corresponds to the sequence of SEQ ID NO: 9 (having a serine residue at position 211) of PCT/EP2014/068628 | MRYFKEEVAGMKYGIYFAYWTKEWFADYKKYMDKVSALGFDVLEISCAALRD<br>VYTTKEQLIELREYAKEKGLVLTAGYGPTKAENLCSEDPEAVRRAMTFFKDLLP<br>KLQLMDIHILGGGLYSYWPVDFTINNDKQGDRARAVRNLRELSKTAEECDVVL<br>GMEVLNRYEGYILNTCEEAIDFVDEIGSSHVKIMLDTFHMNIEETNMADAIRKA<br>GDRLGHLHLSEQNRLVPGKGSLPWAEIGQALRDINYQGAAVMEPFVMQGGTIG<br>SEIKVWRDMVPDLSEEALDRDAKGALEFCRHVFGI |
| SEQ ID NO: 12, which corresponds to the sequence of SEQ ID NO: 10 (having a serine residue at position 211) of PCT/EP2014/068628 | MNKVGMFYTYWSTEWMVDFPATAKRIAGLGFDLMEISLGEFHNLSDAKKREL<br>KAVADDLGLTVMCCIGLKSEYDFASPDKSVRDAGTEYVKRLLDDCHLLGAPVF<br>AGLTFCAWPQSPPLDMKDKRPYVDRAIESVRRVIKVAEDYGIIYALEVVNRFEQ<br>WLCNDAKEAIAFADAVDSPACKVQLDTFHMNIEETSFRDAILACKGKMGHFHL<br>SEANRLPPGEGRLPWDEIFGALKEIGYDGTIVMEPFMRKGGSVSRAVGVWRDM<br>SNGATDEEMDERARRSLQFVRDKLA |
| SEQ ID NO: 13, which corresponds to the sequence of SEQ ID NO: 11 (having a serine residue at position 211) of PCT/EP2014/068628 | MKNPVGIISMQFIRPFTSESLHFLKKSRALGFDFIELLVPEPEDGLDAAEVRRICEG<br>EGLGLVLAARVNLORSIASEEAAARAG<br>GRDYLKYCIEAAEALGATIVGGPLYGEPLVFAGRPPFPWTAEQIATRAARTVEG<br>LAEVAPLAASAGKVFGLEPLNRFETDIVNTTAQAIEVVDAVGSPGLGVMLDTFH<br>MNMEERSIPDAIRATGARLVHFQANENHRGFPGTGTMDWTAIARALGQAGYAG<br>PVSLEPFRRDDERVALPIAHWRAPHEDEDEKLRAGLGLIRSAITLAEVTH |
| SEQ ID NO: 14, plasmid pR1 | CTTAAGGAACGTACAGACGGCTTAAAAGCCTTTAAAAACGTTTTTAAGGGGT<br>TTGTAGACAAGGTAAAGGATAAAACAGCACAATTCCAAGAAAAACACGATT<br>TAGAACCTAAAAAGAACGAATTTGAACTAACTCATAACCGAGAGGTAAAAA<br>AAGAACGAAGTCGAGATCAGGGAATGAGTTTATAAAATAAAAAAAGCACCT<br>GAAAAGGTGTCTTTTTTTGATGGTTTTGAACTTGTTCTTTCTTATCTTGATACA<br>TATAGAAATAACGTCATTTTTATTTTAGTTGCTGAAAGGTGCGTTGAAGTGTT<br>GGTATGTATGTGTTTTAAAGTATTGAAAACCCTTAAAATTGGTTGCACAGAA<br>AAACCCCATCTGTTAAAGTTATAAGTGACTAAACAAATAACTAAATAGATGG<br>GGGTTTCTTTTAATATTATGTGTCCTAATAGTAGCATTTATTCAGATGAAAAA<br>TCAAGGGTTTTAGTGGACAAGACAAAAAGTGGAAAAGTGAGACCATGGAGA<br>GAAAAGAAAATCGCTAATGTTGATTACTTTGAACTTCTGCATATTCTTGAATT<br>TAAAAAGGCTGAAAGAGTAAAAGATTGTGCTGAAATATTAGAGTATAAACA<br>AAATCGTGAAACAGGCGAAAGAAAGTTGTATCGAGTGTGGTTTTGTAAATCC<br>AGGCTTTGTCCAATGTGCAACTGGAGGAGAGCAATGAAACATGGCATTCAGT<br>CACAAAAGGTTGTTGCTGAAGTTATTAAACAAAAGCCAACAGTTCGTTGGTT<br>GTTTCTCACATTAACAGTTAAAAATGTTTATGATGGCGAAGAATTAAATAAG<br>AGTTTGTCAGATATGGCTCAAGGATTTCGCCGAATGATGCAATATAAAAAAA<br>TTAATAAAAATCTTGTTGGTTTTATGCGTGCAACGGAAGTGACAATAAATAA<br>TAAAGATAATTCTTATAATCAGCACATGCATGTATTGGTATGTGTGGAACCA<br>ACTTATTTTAAGAATACAGAAAACTACGTGAATCAAAAACAATGGATTCAAT<br>TTTGGAAAAAGGCAATGAAATTAGACTATGATCCAAATGTAAAAGTTCAAAT<br>GATTCGACCGAAAAATAAATATAAATCGGATATACAATCGGCAATTGACGA<br>AACTGCAAAATATCCTGTAAAGGATACGGATTTTATGACCGATGATGAAGAA<br>AAGAATTTGAAACGTTTGTCTGATTTGGAGGAAGGTTTACACCGTAAAAGGT<br>TAATCTCCTATGGTGGTTTGTTAAAAGAAATACATAAAAAATTAAACCTTGA<br>TGACACAGAAGAAGGCGATTTGATTCATACAGATGATGACGAAAAAGCCGA<br>TGAAGATGGATTTTCTATTATTGCAATGTGGAATTGGGAACGGAAAAATTAT<br>TTTATTAAAGAGTAGTTCAACAAACGGGCCAGTTTGTTGAAGATTAGATGCT<br>ATAATTGTTATTAAAAGGATTGAAGGATGCTTAGGAAGACGAGTTATTAATA<br>GCTGAATAAGAACGGTGCTCTCCAAATATTCTTATTTAGAAAAGCAAATCTA<br>AAATTATCTGAAAAGGGAAGATCTTTCTAAAGAGGAAATGGTGACAGTAGC<br>GAAAAGCATGCAGGGACAATCATCGAAATAACCGCCAAAGGCCAAACATGA<br>TTTGGCCTTTTTTTCGTTAGACATCGTTTCCCTTTAGCCTTTAATTTTAGTATG<br>ATATGTAAATGATATTGAATAAAAGCTAGGAAGTGTCGTAATGAGCACAAA<br>ACCTTTTTACAGAGATACGTGGGCGGAAATTGACTTGTCCGCGATAAAGGAA<br>AATGTCAGCAATATGAAAAAACATATCGGTGAACATGTCCACTTGATGGCAG<br>TTGTGAAAGCAAACGCCTACGGGCATGGTGATGCAGAAACAGCAAAGGCTG<br>CTCTTGACGCAGGTGCTTCATGCTTGGCCGTGGCCATTTTGGATGAAGCGATT<br>TCACTGCGCAAAAAGGGATTGAAGGCGCCTATATTGGTGCTTGGCGCGGTTC<br>CCCCGGAGTATGTGGCAATCGCTGCTGAGTATGACGTGACCTTAACAGGTTA<br>TTCTGTTGAATGGCTTCAGGAGGCAGCCCGCCACACGAAAAAAGGTTCTCTT<br>CATTTTCATCTGAAGGTCGATACGGGGATGAACAGACTTGGTGTAAAAACAG<br>AGGAAGAAGTTCAGAACGTGATGGCAATTCTTGACCGCAACCCTCGTTTAAA<br>GTGCAAAGGGGTATTTACCCATTTTGCGACAGCGGATGAAAAAGAAAGAGG<br>CTATTTCTTAATGCAGTTTGAGCGCTTTAAAGAGCTGATTGCTCCGCTGCCGT<br>TAAAGAATCTAATGGTCCACTGCGCGAACAGCGCCGCTGGACTCCGGCTGAA<br>AAAAGGCTTTTTTAATGCAGTCAGATTCGGCATCGGCATGTATGGCCTTCGC<br>CCGTCTGCTGACATGTCGGACGAGATACCGTTTCAGCTGCGTCCGGCATTTA<br>CCCTGCATTCGACACTGTCACATGTCAAACTGATCAGAAAAGGCGAGAGCGT<br>CAGCTACGGAGCCGAGTACACAGCGGAAAAAGACACATGGATCGGGACGGT<br>GCCTGTAGGCTATGCGGACGGCTGGCTCCGAAAATTGAAAGGGACCGACAT<br>CCTTGTGAAGGGAAAACGCCTGAAAATTGCCGGCCGAATTTGCATGGACCA<br>ATTTATGGTGGAGCTGGATCAGGAATATCCGCCGGGCACAAAAGTCACATTA |

-continued

| Sequence number | Sequences |
|---|---|
| | ATAGGCCGGCAGGGGGATGAATATATTTCCATGGATGAGATTGCAGGAAGG |
| | CTCGAAACCATTAACTATGAGGTGGCCTGTACAATAAGTTCCCGTGTTCCCC |
| | GTATGTTTTTGGAAAATGGGAGTATAATGGAAGTAAGAAATCCTTTATTGCA |
| | GGTAAATATAAGCAATTAACTTACCTAAATGGAGAATTCAATCTATTATTAA |
| | TCTGTTCAGCAATCGGGCGCGATTGCTGAATAAAAGATACGAGAGACCTCTC |
| | TTGTATCTTTTTTATTTTGAGTGGTTTTGTCCGTTACACTAGAAAACCGAAAG |
| | ACAATAAAAATTTTATTCTTGCTGAGTCTGGCTTTCGGTAAGCTAGACAAAA |
| | CGGACAAAATAAAAATTGGCAAGGGTTTAAAGGTGGAGATTTTTTGAGTGAT |
| | CTTCTCAAAAAATACTACCTGTCCCTTGCTGATTTTTAAACGAGCACGAGAG |
| | CAAAACCCCCCTTTGCTGAGGTGGCAGAGGGCAGGTTTTTTTGTTTCTTTTTT |
| | CTCGTAAAAAAAAGAAAGGTCTTAAAGGTTTTATGGTTTTGGTCGGCACTGC |
| | CGACAGCCTCGCAGAGCACACACTTTATGAATATAAAGTATAGTGTGTTATA |
| | CTTTACTTGGAAGTGGTTGCCGGAAAGAGCGAAAATGCCTCACATTTGTGCC |
| | ACCTAAAAAGGAGCGATTTACATATGAGTTATGCAGTTTGTAGAATGCAAAA |
| | AGTGAAATCATAATGATAGGTGGTATGTTTTCGCTTGAACTTTTAAATACAG |
| | CCATTGAACATACGGTTGATTTAATAACTGACAAACATCACCCTCTTGCTAA |
| | AGCGGCCAAGGACGCTGCCGCCGGGGCTGTTTGCGTTTTTGCCGTGATTTCG |
| | TGTATCATTGGTTTACTTATTTTTTTGCCAAAGCTGTAATGGCTGAAAATTCT |
| | TACATTTATATTTACATTTTTAGAAATGGGCGTGAAAAAAAGCGCGCGATTA |
| | TGTAAAATATAAAGTGATAGCGGTACCATTATAGGT**AAGAGAGGAATGTAC** |
| | **AC**ATGAAACATGGTATATACTACGCATATTGGGAACAAGAATGGGAAGCTG |
| | ATTACAAATACTATATTGAGAAGGTTGCAAAGCTTGGTTTTGATATTCTAGA |
| | GATTGCAGCTTCACCGCTACCTTTTTACAGTGACATTCAGATTAATGAGCTCA |
| | AGGCATGTGCCCATGGCAATGGAATTACACTTACGGTAGGCCATGGGCCTAG |
| | TGCAGAACAAAACCTGTCTTCTCCCGACCCCGATATTCGCAAAAATGCTAAA |
| | GCTTTTTATACCGATTTACTCAAACGACTTTACAAGCTGGATGTACATTTGAT |
| | AGGTGGGGCTTTATATTCTTATTGGCCGATAGATTACACAAAGACAATTGAT |
| | AAAAAAGGCGATTGGGAACGCAGCGTTGAAAGTGTTCGAGAAGTTGCTAAG |
| | GTGGCCGAAGCCTGTGGAGTGGATTTCTGCCTAGAGGTTCTTAATAGATTTG |
| | AGAATTATTTAATTAACACAGCACAAGAGGGTGTAGATTTTGTAAAACAGGT |
| | TGACCATAACAATGTAAAGGTAATGCTTGATACCTTCCACATGAATATTGAG |
| | GAAGATAGTATCGGAGGTGCAATCAGGACTGCGGGCTCTTACTTGGGACATT |
| | TACACACTGGCGAATGTAATCGTAAAGTTCCCGGCAGAGGAAGAATTCCATG |
| | GGTAGAAATTGGTGAGGCTCTTGCTGACATAGGTTATAACGGTAGTGTTGTT |
| | ATGGAACCTTTTGTTAGAATGGGCGGAACTGTCGGATCTAATATTAAGGTTT |
| | GGCGTGACATTAGTAACGGTGCAGATGAGAAAATGCTGGATAGAGAAGCAC |
| | AGGCCGCACTTGATTTCTCCAGATATGTATTAGAATGTCATAAACACTCCTA |
| | AGAATTC |
| SEQ ID NO: 15, plasmid pR2 | CTTAAGGAACGTACAGACGGCTTAAAAGCCTTTAAAAACGTTTTTAAGGGGT |
| | TTGTAGACAAGGTAAAGGATAAAACAGCACAATTCCAAGAAAAACACGATT |
| | TAGAACCTAAAAAGAACGAATTTGAACTAACTCATAACCGAGAGGTAAAAA |
| | AAGAACGAAGTCGAGATCAGGGAATGAGTTTATAAAATAAAAAAAGCACCT |
| | GAAAAGGTGTCTTTTTTTTGATGGTTTTGAACTTGTTCTTTCTTATCTTGATACA |
| | TATAGAAATAACGTCATTTTTATTTTAGTTGCTGAAAGGTGCGTTGAAGTGTT |
| | GGTATGTATGTGTTTTAAAGTATTGAAAACCCTTAAAATTGGTTGCACAGAA |
| | AAACCCCATCTGTTAAAGTTATAAGTGACTAAACAAATAACTAAATAGATGG |
| | GGGTTTCTTTTAATATTATGTGTCCTAATAGTAGCATTTATTCAGATGAAAAA |
| | TCAAGGGTTTTAGTGGACAAGACAAAAAGTGGAAAAGTGAGACCATGGAGA |
| | GAAAAGAAAATCGCTAATGTTGATTACTTTGAACTTCTGCATATTCTTGAATT |
| | TAAAAAGGCTGAAAGAGTAAAAGATTGTGCTGAAATATTAGAGTATAAACA |
| | AAATCGTGAAACAGGCGAAAGAAAGTTGTATCGAGTGTGGTTTTGTAAATCC |
| | AGGCTTTGTCCAATGTGCAACTGGAGGAGAGCAATGAAACATGGCATTCAGT |
| | CACAAAAGGTTGTTGCTGAAGTTATTAAACAAAAGCCAACAGTTCGTTGGTT |
| | GTTTCTCACATTAACAGTTAAAAATGTTTATGATGGCGAAGAATTAAATAAG |
| | AGTTTGTCAGATATGGCTCAAGGATTTCGCCGAATGATGCAATATAAAAAAA |
| | TTAATAAAAATCTTGTTGGTTTTATGCGTGCAACGGAAGTGACAATAAATAA |
| | TAAAGATAATTCTTATAATCAGCACATGCATGTATTGGTATGTGTGGAACCA |
| | ACTTATTTTAAGAATACAGAAAACTACGTGAATCAAAAACAATGGATTCAAT |
| | TTTGGAAAAAGGCAATGAAATTAGACTATGATCCAAATGTAAAAGTTCAAAT |
| | GATTCGACCGAAAAATAAATATAAATCGGATATACAATCGGCAATTGACGA |
| | AACTGCAAAATATCCTGTAAAGGATACGGATTTTATGACCGATGATGAAGAA |
| | AAGAATTTGAAACGTTTGTCTGATTTGGAGGAAGGTTTACACCGTAAAAGGT |
| | TAATCTCCTATGGTGGTTTGTTAAAAGAAATACATAAAAAATTAAACCTTGA |
| | TGACACAGAAGAAGGCGATTTGATTCATACAGATGATGACGAAAAAGCCGA |
| | TGAAGATGGATTTTCTATTATTGCAATGTGGAATTGGGAACGGAAAAATTAT |
| | TTTATTAAAGAGTAGTTCAACAAACGGGCCAGTTTGTTGAAGATTAGATGCT |
| | ATAATTGTTATTAAAAGGATTGAAGGATGCTTAGGAAGACGAGTTATTAATA |
| | GCTGAATAAGAACGGTGCTCTCCAAATATTCTTATTTAGAAAAGCAAATCTA |
| | AAATTATCTGAAAAGGGAAGATCTTTCTAAAGAGGAAATGGTGACAGTAGC |
| | GAAAAGCATGCAGGGACAATCATCGAAATAACCGCCAAAGGCCAAACATGA |
| | TTTGGCCTTTTTTTCGTTAGACATCGTTTCCCTTTAGCCTTTAATTTTAGTATG |
| | ATATGTAAATGATATTGAATAAAAGCTAGGAAGTGTCGTAATGAGCACAAA |
| | ACCTTTTTACAGAGATACGTGGGCGGAAATTGACTTGTCCGCGATAAAGGAA |
| | AATGTCAGCAATATGAAAAAACATATCGGTGAACATGTCCACTTGATGGCAG |
| | TTGTGAAAGCAAACGCCTACGGGCATGGTGATGCAGAAACAGCAAAGGCTG |
| | CTCTTGACGCAGGTGCTTCATGCTTGGCCGTGGCCATTTTGGATGAAGCGATT |
| | TCACTGCGCAAAAAGGGATTGAAGGCGCCTATATTGGTGCTTGGCGCGGTTC |

-continued

| Sequence number | Sequences |
|---|---|
| | CCCCGGAGTATGTGGCAATCGCTGCTGAGTATGACGTGACCTTAACAGGTTA |
| | TTCTGTTGAATGGCTTCAGGAGGCAGCCCGCCACACGAAAAAAGGTTCTCTT |
| | CATTTTCATCTGAAGGTCGATACGGGGATGAACAGACTTGGTGTAAAAACAG |
| | AGGAAGAAGTTCAGAACGTGATGGCAATTCTTGACCGCAACCCTCGTTTAAA |
| | GTGCAAAGGGGTATTTACCCATTTTGCGACAGCGGATGAAAAAGAAAGAGG |
| | CTATTTCTTAATGCAGTTTGAGCGCTTTAAAGAGCTGATTGCTCCGCTGCCGT |
| | TAAAGAATCTAATGGTCCACTGCGCGAACAGCGCCGCTGGACTCCGGCTGAA |
| | AAAAGGCTTTTTTAATGCAGTCAGATTCGGCATCGGCATGTATGGCCTTCGC |
| | CCGTCTGCTGACATGTCGGACGAGATACCGTTTCAGCTGCGTCCGGCATTTA |
| | CCCTGCATTCGACACTGTCACATGTCAAACTGATCAGAAAAGGCGAGAGCGT |
| | CAGCTACGGAGCCGAGTACACAGCGGAAAAAGACACATGGATCGGGACGGT |
| | GCCTGTAGGCTATGCGGACGGCTGGCTCCGAAAATTGAAAGGGACCGACAT |
| | CCTTGTGAAGGGAAAACGCCTGAAAATTGCCGGCCGAATTTGCATGGACCA |
| | ATTTATGGTGGAGCTGGATCAGGAATATCCGCCGGGCACAAAAGTCACATTA |
| | ATAGGCCGGCAGGGGGATGAATATATTTCCATGGATGAGATTGCAGGAAGG |
| | CTCGAAACCATTAACTATGAGGTGGCCTGTACAATAAGTTCCCGTGTTCCCC |
| | GTATGTTTTTGGAAAATGGGAGTATAATGGAAGTAAGAAATCCTTTATTGCA |
| | GGTAAATATAAGCAATTAACTTACCTAAATGGAGAATTCAATCTATTATTAA |
| | TCTGTTCAGCAATCGGGCGCGATTGCTGAATAAAAGATACGAGAGACCTCTC |
| | TTGTATCTTTTTTATTTTGAGTGGTTTTGTCCGTTACACTAGAAAACCGAAAG |
| | ACAATAAAAATTTTATTCTTGCTGAGTCTGGCTTTCGGTAAGCTAGACAAAA |
| | CGGACAAAATAAAAATTGGCAAGGGTTTAAAGGTGGAGATTTTTTGAGTGAT |
| | CTTCTCAAAAAATACTACCTGTCCCTTGCTGATTTTTAAACGAGCACGAGAG |
| | CAAAACCCCCCTTTGCTGAGGTGGCAGAGGGCAGGTTTTTTTGTTTCTTTTTT |
| | CTCGTAAAAAAAAGAAAGGTCTTAAAGGTTTTATGGTTTTGGTCGGCACTGC |
| | CGACAGCCTCGCAGAGCACACACTTTATGAATATAAAGTATAGTGTGTTATA |
| | CTTTACTTGGAAGTGGTTGCCGGAAAGAGCGAAAATGCCTCACATTTGTGCC |
| | ACCTAAAAAGGAGCGATTTACATATGAGTTATGCAGTTTGTAGAATGCAAAA |
| | AGTGAAATCATAATGATAGGTGGTATGTTTTCGCTTGAACTTTTAAATACAG |
| | CCATTGAACATACGGTTGATTTAATAACTGACAAACATCACCCTCTTGCTAA |
| | AGCGGCCAAGGACGCTGCCGCCGGGGCTGTTTGCGTTTTTGCCGTGATTTCG |
| | TGTATCATTGGTTTACTTATTTTTTTGCCAAAGCTGTAATGGCTGAAAATTCT |
| | TACATTTATATTTACATTTTTAGAAATGGGCGTGAAAAAAAGCGCGCGATTA |
| | TGTAAAATATAAAGTGATAGCGGTACCATTATAGGT**AGAAAGGAGGATTAC** |
| | **AT**ATGAAACATGGTATATACTACGCATATTGGGAACAAGAATGGGAAGCTG |
| | ATTACAAATACTATATTGAGAAGGTTGCAAAGCTTGGTTTTGATATTCTAGA |
| | GATTGCAGCTTCACCGCTACCTTTTTACAGTGACATTCAGATTAATGAGCTCA |
| | AGGCATGTGCCCATGGCAATGGAATTACACTTACGGTAGGCCATGGGCCTAG |
| | TGCAGAACAAAACCTGTCTTCTCCCGACCCCGATATTCGCAAAAATGCTAAA |
| | GCTTTTTATACCGATTTACTCAAACGACTTTACAAGCTGGATGTACATTTGAT |
| | AGGTGGGGCTTTATATTCTTATTGGCCGATAGATTACACAAAGACAATTGAT |
| | AAAAAAGGCGATTGGGAACGCAGCGTTGAAAGTGTTCGAGAAGTTGCTAAG |
| | GTGGCCGAAGCCTGTGGAGTGGATTTCTGCCTAGAGGTTCTTAATAGATTTG |
| | AGAATTATTTAATTAACACAGCACAAGAGGGTGTAGATTTTGTAAAACAGGT |
| | TGACCATAACAATGTAAAGGTAATGCTTGATACCTTCCACATGAATATTGAG |
| | GAAGATAGTATCGGAGGTGCAATCAGGACTGCGGGCTCTTACTTGGGACATT |
| | TACACACTGGCGAATGTAATCGTAAAGTTCCCGGCAGAGGAAGAATTCCATG |
| | GGTAGAAATTGGTGAGGCTCTTGCTGACATAGGTTATAACGGTAGTGTTGTT |
| | ATGGAACCTTTTGTTAGAATGGGCGGAACTGTCGGATCTAATATTAAGGTTT |
| | GGCGTGACATTAGTAACGGTGCAGATGAGAAAATGCTGGATAGAGAAGCAC |
| | AGGCCGCACTTGATTTCTCCAGATATGTATTAGAATGTCATAAACACTCCTA |
| | AGAATTC |
| SEQ ID NO: 16, plasmid | CTTAAGGAACGTACAGACGGCTTAAAAGCCTTTAAAAACGTTTTTAAGGGGT |
| pR3 | TTGTAGACAAGGTAAAGGATAAAACAGCACAATTCCAAGAAAAACACGATT |
| | TAGAACCTAAAAAGAACGAATTTGAACTAACTCATAACCGAGAGGTAAAAA |
| | AAGAACGAAGTCGAGATCAGGGAATGAGTTTATAAAATAAAAAAAGCACCT |
| | GAAAAGGTGTCTTTTTTTGATGGTTTTGAACTTGTTCTTTCTTATCTTGATACA |
| | TATAGAAATAACGTCATTTTTATTTTAGTTGCTGAAAGGTGCGTTGAAGTGTT |
| | GGTATGTATGTGTTTTAAAGTATTGAAAACCCTTAAAATTGGTTGCACAGAA |
| | AAACCCCATCTGTTAAAGTTATAAGTGACTAAACAAATAACTAAATAGATGG |
| | GGGTTTCTTTTAATATTATGTGTCCTAATAGTAGCATTTATTCAGATGAAAAA |
| | TCAAGGGTTTTAGTGGACAAGACAAAAAGTGGAAAAGTGAGACCATGGAGA |
| | GAAAAGAAAATCGCTAATGTTGATTACTTTGAACTTCTGCATATTCTTGAATT |
| | TAAAAAGGCTGAAAGAGTAAAAGATTGTGCTGAAATATTAGAGTATAAACA |
| | AAATCGTGAAACAGGCGAAAGAAAGTTGTATCGAGTGTGGTTTTGTAAATCC |
| | AGGCTTTGTCCAATGTGCAACTGGAGGAGAGCAATGAAACATGGCATTCAGT |
| | CACAAAAGGTTGTTGCTGAAGTTATTAAACAAAAGCCAACAGTTCGTTGGTT |
| | GTTTCTCACATTAACAGTTAAAAATGTTTATGATGGCGAAGAATTAAATAAG |
| | AGTTTGTCAGATATGGCTCAAGGATTTCGCCGAATGATGCAATATAAAAAAA |
| | TTAATAAAAATCTTGTTGGTTTTATGCGTGCAACGGAAGTGACAATAAATAA |
| | TAAAGATAATTCTTATAATCAGCACATGCATGTATTGGTATGTGTGGAACCA |
| | ACTTATTTTAAGAATACAGAAAACTACGTGAATCAAAAACAATGGATTCAAT |
| | TTTGGAAAAAGGCAATGAAATTAGACTATGATCCAAATGTAAAAGTTCAAAT |
| | GATTCGACCGAAAAATAAATATAAATCGGATATACAATCGGCAATTGACGA |
| | AACTGCAAAATATCCTGTAAAGGATACGGATTTTATGACCGATGATGAAGAA |
| | AAGAATTTGAAACGTTTGTCTGATTTGGAGGAAGGTTTACACCGTAAAAGGT |
| | TAATCTCCTATGGTGGTTTGTTAAAAGAAATACATAAAAAATTAAACCTTGA |

-continued

| Sequence number | Sequences |
| --- | --- |
| | TGACACAGAAGAAGGCGATTTGATTCATACAGATGATGACGAAAAAGCCGA<br>TGAAGATGGATTTTCTATTATTGCAATGTGGAATTGGGAACGGAAAAATTAT<br>TTTATTAAAGAGTAGTTCAACAAACGGGCCAGTTTGTTGAAGATTAGATGCT<br>ATAATTGTTATTAAAAGGATTGAAGGATGCTTAGGAAGACGAGTTATTAATA<br>GCTGAATAAGAACGGTGCTCTCCAAATATTCTTATTTAGAAAAGCAAATCTA<br>AAATTATCTGAAAAGGGAAGATCTTTCTAAAGAGGAAATGGTGACAGTAGC<br>GAAAAGCATGCAGGGACAATCATCGAAATAACCGCCAAAGGCCAAACATGA<br>TTTGGCCTTTTTTTCGTTAGACATCGTTTCCCTTTAGCCTTTAATTTTAGTATG<br>ATATGTAAATGATATTGAATAAAAGCTAGGAAGTGTCGTAATGAGCACAAA<br>ACCTTTTTACAGAGATACGTGGGCGGAAATTGACTTGTCCGCGATAAAGGAA<br>AATGTCAGCAATATGAAAAAACATATCGGTGAACATGTCCACTTGATGGCAG<br>TTGTGAAAGCAAACGCCTACGGGCATGGTGATGCAGAAACAGCAAAGGCTG<br>CTCTTGACGCAGGTGCTTCATGCTTGGCCGTGGCCATTTTGGATGAAGCGATT<br>TCACTGCGCAAAAAGGGATTGAAGGCGCCTATATTGGTGCTTGGCGCGGTTC<br>CCCCGGAGTATGTGGCAATCGCTGCTGAGTATGACGTGACCTTAACAGGTTA<br>TTCTGTTGAATGGCTTCAGGAGGCAGCCCGCCACACGAAAAAAGGTTCTCTT<br>CATTTTCATCTGAAGGTCGATACGGGGATGAACAGACTTGGTGTAAAAACAG<br>AGGAAGAAGTTCAGAACGTGATGGCAATTCTTGACCGCAACCCTCGTTTAAA<br>GTGCAAAGGGGTATTTACCCATTTTGCGACAGCGGATGAAAAAGAAAGAGG<br>CTATTTCTTAATGCAGTTTGAGCGCTTTAAAGAGCTGATTGCTCCGCTGCCGT<br>TAAAGAATCTAATGGTCCACTGCGCGAACAGCGCCGCTGGACTCCGGCTGAA<br>AAAAGGCTTTTTTAATGCAGTCAGATTCGGCATCGGCATGTATGGCCTTCGC<br>CCGTCTGCTGACATGTCGGACGAGATACCGTTTCAGCTGCGTCCGGCATTTA<br>CCCTGCATTCGACACTGTCACATGTCAAACTGATCAGAAAAGGCGAGAGCGT<br>CAGCTACGGAGCCGAGTACACAGCGGAAAAAGACACATGGATCGGGACGGT<br>GCCTGTAGGCTATGCGGACGGCTGGCTCCGAAAATTGAAAGGGACCGACAT<br>CCTTGTGAAGGGAAAACGCCTGAAAATTGCCGGCCGAATTTGCATGGACCA<br>ATTTATGGTGGAGCTGGATCAGGAATATCCGCCGGGCACAAAAGTCACATTA<br>ATAGGCCGGCAGGGGGATGAATATATTTCCATGGATGAGATTGCAGGAAGG<br>CTCGAAACCATTAACTATGAGGTGGCCTGTACAATAAGTTCCCGTGTTCCCC<br>GTATGTTTTTGGAAAATGGGAGTATAATGGAAGTAAGAAATCCTTTATTGCA<br>GGTAAATATAAGCAATTAACTTACCTAAATGGAGAATTCAATCTATTATTAA<br>TCTGTTCAGCAATCGGGCGCGATTGCTGAATAAAAGATACGAGAGACCTCTC<br>TTGTATCTTTTTTATTTTGAGTGGTTTTGTCCGTTACACTAGAAAACCGAAAG<br>ACAATAAAAATTTTATTCTTGCTGAGTCTGGCTTTCGGTAAGCTAGACAAAA<br>CGGACAAAATAAAAATTGGCAAGGGTTTAAAGGTGGAGATTTTTTGAGTGAT<br>CTTCTCAAAAAATACTACCTGTCCCTTGCTGATTTTTAAACGAGCACGAGAG<br>CAAAACCCCCCTTTGCTGAGGTGGCAGAGGGCAGGTTTTTTTGTTTCTTTTTT<br>CTCGTAAAAAAAAGAAAGGTCTTAAAGGTTTTATGGTTTTGGTCGGCACTGC<br>CGACAGCCTCGCAGAGCACACACTTTATGAATATAAAGTATAGTGTGTTATA<br>CTTTACTTGGAAGTGGTTGCCGGAAAGAGCGAAAATGCCTCACATTTGTGCC<br>ACCTAAAAAGGAGCGATTTACATATGAGTTATGCAGTTTGTAGAATGCAAAA<br>AGTGAAATCATAATGATAGGTGGTATGTTTTCGCTTGAACTTTTAAATACAG<br>CCATTGAACATACGGTTGATTTAATAACTGACAAACATCACCCTCTTGCTAA<br>AGCGGCCAAGGACGCTGCCGCCGGGGCTGTTTGCGTTTTTGCCGTGATTTCG<br>TGTATCATTGGTTTACTTATTTTTTTGCCAAAGCTGTAATGGCTGAAAATTCT<br>TACATTTATATTTACATTTTTAGAAATGGGCGTGAAAAAAAGCGCGCGATTA<br>TGTAAAATATAAAGTGATAGCGGTACCATTATAGGT**AGAAAGGAGGATTCG**<br>**AA**ATGAAACATGGTATATACTACGCATATTGGGAACAAGAATGGGAAGCTG<br>ATTACAAATACTATATTGAGAAGGTTGCAAAGCTTGGTTTTGATATTCTAGA<br>GATTGCAGCTTCACCGCTACCTTTTTACAGTGACATTCAGATTAATGAGCTCA<br>AGGCATGTGCCCATGGCAATGGAATTACACTTACGGTAGGCCATGGGCCTAG<br>TGCAGAACAAAACCTGTCTTCTCCCGACCCCGATATTCGCAAAAATGCTAAA<br>GCTTTTTATACCGATTTACTCAAACGACTTTACAAGCTGGATGTACATTTGAT<br>AGGTGGGGCTTTATATTCTTATTGGCCGATAGATTACACAAAGACAATTGAT<br>AAAAAAGGCGATTGGGAACGCAGCGTTGAAAGTGTTCGAGAAGTTGCTAAG<br>GTGGCCGAAGCCTGTGGAGTGGATTTCTGCCTAGAGGTTCTTAATAGATTTG<br>AGAATTATTTAATTAACACAGCACAAGAGGGTGTAGATTTTGTAAAACAGGT<br>TGACCATAACAATGTAAAGGTAATGCTTGATACCTTCCACATGAATATTGAG<br>GAAGATAGTATCGGAGGTGCAATCAGGACTGCGGGCTCTTACTTGGGACATT<br>TACACACTGGCGAATGTAATCGTAAAGTTCCCGGCAGAGGAAGAATTCCATG<br>GGTAGAAATTGGTGAGGCTCTTGCTGACATAGGTTATAACGGTAGTGTTGTT<br>ATGGAACCTTTTGTTAGAATGGGCGGAACTGTCGGATCTAATATTAAGGTTT<br>GGCGTGACATTAGTAACGGTGCAGATGAGAAAATGCTGGATAGAGAAGCAC<br>AGGCCGCACTTGATTTCTCCAGATATGTATTAGAATGTCATAAACACTCCTA<br>AGAATTC |
| SEQ ID NO: 17, alrA gene | ATGAGCACAAAACCTTTTTACAGAGATACGTGGGCGGAAATTGACTTGTCCG<br>CGATAAAGGAAAATGTCAGCAATATGAAAAAACATATCGGTGAACATGTCC<br>ACTTGATGGCAGTTGTGAAAGCAAACGCCTACGGGCATGGTGATGCAGAAA<br>CAGCAAAGGCTGCTCTTGACGCAGGTGCTTCATGCTTGGCCGTGGCCATTTT<br>GGATGAAGCGATTTCACTGCGCAAAAAGGGATTGAAGGCGCCTATATTGGT<br>GCTTGGCGCGGTTCCCCCGGAGTATGTGGCAATCGCTGCTGAGTATGACGTG<br>ACCTTAACAGGTTATTCTGTTGAATGGCTTCAGGAGGCAGCCCGCCACACGA<br>AAAAAGGTTCTCTTCATTTTCATCTGAAGGTCGATACGGGGATGAACAGACT<br>TGGTGTAAAAACAGAGGAAGAAGTTCAGAACGTGATGGCAATTCTTGACCG<br>CAACCCTCGTTTAAAGTGCAAAGGGGTATTTACCCATTTTGCGACAGCGGAT<br>GAAAAAGAAAGAGGCTATTTCTTAATGCAGTTTGAGCGCTTTAAAGAGCTGA |

-continued

| Sequence number | Sequences |
|---|---|
| | TTGCTCCGCTGCCGTTAAAGAATCTAATGGTCCACTGCGCGAACAGCGCCGC<br>TGGACTCCGGCTGAAAAAGGCTTTTTAATGCAGTCAGATTCGGCATCGGC<br>ATGTATGGCCTTCGCCCGTCTGCTGACATGTCGGACGAGATACCGTTTCAGC<br>TGCGTCCGGCATTTACCCTGCATTCGACACTGTCACATGTCAAACTGATCAG<br>AAAA<br>GGCGAGAGCGTCAGCTACGGAGCCGAGTACACAGCGGAAAAAGACACATGG<br>ATCGGGACGGTGCCTGTAGGCTATGCGGACGGCTGGCTCCGAAAATTGAAA<br>GGGACCGACATCCTTGTGAAGGGAAAACGCCTGAAAATTGCCGGCCGAATT<br>TGCATGGACCAATTTATGGTGGAGCTGGATCAGGAATATCCGCCGGGCACAA<br>AAGTCACATTAATAGGCCGGCAGGGGGATGAATATATTTCCATGGATGAGAT<br>TGCAGGAAGGCTCGAAACCATTAACTATGAGGTGGCCTGTACAATAAGTTCC<br>CGTGTTCCCCGTATGTTTTTGGAAAATGGGAGTATAATGGAAGTAAGAAATC<br>CTTTATTGCAGGTAAATATAAGCAATTAA |
| SEQ ID NO: 18, yqfD gene | GTGAAAAATAAATGGCTGTCTTTTTTTTCGGGTAAGGTCCAGCTTGAATTGA<br>CGGGAAGAGGGATTGAGCGGCTCCTTAATGAATGCACAAGACAGGGGATTC<br>CGGTCTTTCATGTCAAAAAAAAGAAAGAAGCCGTATCGTTATATATACAGCT<br>TCAGGATGTACATGCCTTTCGGCGGGTAAGAAGTAAATTTAAATGTAAAGCC<br>CGATTTATCAATCGGAAGGGATTTCCCTTCCTGTTGCTGAAATCAAAGCTGA<br>ATATAGGGTTTACGATCGGTTTTGCGATTTTTTTCATTCTTTTGTTTTTGCTGT<br>CCAATATGGTGTGGAAAATTGATGTGACAGGCGCTAAGCCTGAAACAGAAC<br>ATCAAATGAGGCAGCATCTTAATGAAATCGGCGTCAAAAAGGGCCGTCTGC<br>AGTTTTTAATGATGTCGCCCGAAAAAATACAGAAATCATTAACCAATGGAAT<br>AGACAATATCACTTGGGTCGGAGTTGATCTGAAGGGGACGACCATTCATATG<br>AAAGTTGTGGAGAAAAATGAGCCCGAAAAAGAAAAATATGTTAGCCCGCGC<br>AATATTGTCGCCAAAAAGAAAGCAACCATTACGAGAATGTTTGTGCAAAAA<br>GGACAGCCCATGGCCGCCATACACGATCATGTTGAAAAGGGACAGCTGCTT<br>GTTTCGGGACTGATCGGCAGCGAAGACC<br>ATCAGCAGGAAGTCGCCTCAAAAGCAGAAATTTATGGAGAAACCTGGTATA<br>GATCAGAAGTGACAGTCCCGCTTGAAACATTATTTAACGTCTATACGGGCAA<br>AGTAAGGACAAAGCACAAGCTTTCTTTTGGTTCTTTGGCAATCCCGATCTGG<br>GGGATGACGTTTAAAAAAGAGGAATTGAAGCATCCAAAAACAGAACAAGAA<br>AAGCATTCGCTTCATTTTCTCGGATTTAAGCTCCCTGTATCCTATGTCAAAGA<br>GCAAACGAGAGAAAGTGAAGAGGCTTTGCGAAAATATACAAAAGAAGAAG<br>CAGTTCAAGAAGGCATTAAATTGGGTAAACAGGATGTAGAGGATAAAATAG<br>GCGAAAACGGCGAGGTGAAAAGTGAAAAAGTTTTGCACCAGACTGTTGAGA<br>ATGGTAAAGTAAAGTTGATTATTCTCTACCAAGTTATAGAAGATATCGTTCA<br>AACCACACCTATTGTCAGGGAGACTGAAGAATGA |
| SEQ ID NO: 19, EmR-comK cassette | TGACAATATGTCTCCTGTCATTATGTCCTTCACACTCTGATCAAACGTGACCA<br>GCTGTTTTTCTTCCGTGAAATTCATGACAAAAATATAATCATTGTCCTGATCC<br>TGCCTCGCTTGTACGGAGACGCCTTTTCCGTGCCGAACCGGAAAAACTGGAG<br>AGAGAGACAGGTCTGTGATCAGACCCTCATAGAAATCACGCTGAAATTGATC<br>CTCCAAACGCGCGCCGATAAAATACGCCTTGCCCTGCTGATACTCATGGCTT<br>GTGACCGCTGGCGTGCGCGCATAAAAATCTTCTTGATACACCGCTTCCACTG<br>AAGCTGTCTTTACATCAATCACGGTTGCATAATCCTTCATTTCATATATTTGG<br>CTGCGGTAGCTGACAGCGTTTCGATCCTTCGGATACAGGGTGTCCGTTTCAA<br>GAGGCTCAACTCCAAATATAGCTTGAAATCGATATCTCTGCAGTCGCGATGA<br>TTAATTAATTCAGAACGCTCGGTTGCCGCCGGGCGTTTTTTATGCAGCAATG<br>GCAAGAACGTCCCGGGGAGCTCCTAAC<br>TTATAGGGGTAACACTTAAAAAAGAATCAATAACGATAGAAACCGCTCCTA<br>AAGCAGGTGCATTTTTTCCTAACGAAGAAGGCAATAGTTCACATTTATTGTCT<br>AAATGAGAATGGACTCTAGAAGAAACTTCGTTTTTAATCGTATTTAAAACAA<br>TGGGATGAGATTCAATTATATGATTTCTCAAGATAACAGCTTCTATATCAAAT<br>GTATTAAGGATATTGGTTAATCCAATTCCGATATAAAAGCCAAAGTTTTGAA<br>GTGCATTTAACATTTCTACATCATTTTTATTTGCGCGTTCCACAATCTCTTTTC<br>GAGAAATATTCTTTTCTTCTTTAGAGAGCGAAGCCAGTAACGCTTTTTCAGAA<br>GCATATAATTCCCAACAGCCTCGATTTCCACAGCTGCATTTGGGTCCATTAA<br>AATCTATCGTCATATGACCCATTTCCCCAGAAAAACCCTGAACACCTTTATA<br>CAATTCGTTGTTAATAACAAGTCCAGTTCCAATTCCGATATTAATACTGATGT<br>AAACGATGTTTTCATAGTTTTTTGTCATACCAAATACTTTTTCACCGTATGCT<br>CCTGCATTAGCTTCATTTTCAACAAAAACCGGAACATTAAACTCACTCTCAA<br>TTAAAAACTGCAAATCTTTGATATTCCAATTTAAGTTAGGCATGAAAATAAT<br>TTGCTGATGACGATCTACAAGGCCTGGAACACAAATTCCTATTCCGACTAGA<br>CCATAAGGGGACTCAGGCATATGGGTTACAAAACCATGAATAAGTGCAAAT<br>AAAATCTCTTTTACTTCACTAGCGGAAGAACTAGACAAGTCAGAAGTCTTCT<br>CGAGAATAATATTTCCTTCTAAGTCGGTTAGAATTCCGTTAAGATAGTCGACT<br>CCTATATCAATACCAATCGAGTAGCCTGCATTCTTATTAAAAACAAGCATTA<br>CAGGTCTTCTGCCGCCTCTAGATTGCCCTGCCCCAATTTCAAAAATAAAATCT<br>TTTTCAAGCAGTGTATTTACTTGAGAGGAGACAGTAGACTTGTTTAATCCTGT<br>AATCTCAGAGAGAGTTGCCCTGGAGACAGGGGAGTTCTTCAAAATTTCATCT<br>AATATTAATTTTTGATTCATTTTTTTTACTAAAGCTTGATCTGCAATTTGAATA<br>ATAACCACTCCTTTGTTTATCCACCGAACTAAGTTGGTGTTTTTTGAAGCTTG<br>AATTAGATATTTAAAAGTATCATATCTAATATTATAACTAAATTTTCTAAAAA<br>AAACATTGAAATAAACATTTATTTTGTATATGATGAGATAAAGTTAGTTTATT<br>GGATAAACAAACTAACTCAATTAAGATAGTTGATGGATAAACTTGTTCACTT<br>AAATCAAAGGGGGAAATGACAAATGGTCCAAACTAGTGATATCTAAAAATC<br>AAAGGGGGAAATGGGATCCAAAGGAGGCCATAATATGAGTCAGAAAACAG<br>ACGCACCTTTAGAATCGTATGAAGTGAACGGCGCAACAATTGCCGTGCTGCC |

-continued

| Sequence number | Sequences |
|---|---|
| | AGAAGAAATAGACGGCAAAATCTGTTCCAAAATTATTGAAAAAGATTGCGT<br>GTTTTATGTAAACATGAAGCCGCTGCAAATTGTCGACAGAAGCTGCCGATTT<br>TTTGGATCAAGCTATGCGGGAAGAAAAGCAGGAACTTATGAAGTGACAAAA<br>ATTTCACACAAGCCGCCGATCATGGTGGACCCTTCGAACCAAATCTTTTTATT<br>CCCTACACTTTCTTCGACAAGACCCCAATGCGGCTGGATTTCCCATGTGCATG<br>TAAAAGAATTCAAAGCGACTGAATTCGACGATACGGAAGTGACGTTTTCCAA<br>TGGGAAAACGATGGAGCTGCCGATCTCTTATAATTCGTTCGAGAACCAGGTA<br>TACCGAACAGCGTGGCTCAGAACCAAATTCCAAGACAGAATCGACCACCGC<br>GTGCCGAAAAGACAGGAATTTATGCTGTACCCGAAAGAAGAGCGGACGAAG<br>ATGATTTATGATTTTATTTTGCGTGAGCTCGGGGAACGGTATTAGAAAAATA<br>GCCGCGGGCGGCCGCACTCTTCCTTTTTCAATATTATTGAAGCATTTATCAGG<br>GTTATTGTCTCATGAGCGGATACATATTTGAATGTATTTAGAAAAATAAACA<br>AATAGGGGTTCCGCGCACATTTCCCCGAAAAGTGCCACCTGACGTCTAAGAA<br>ACCATTATTATCATGACATTAACCTATAAAAATAGGCGTATCACGAGGCCCT<br>TTCGTCTTCAAGAATTGATCCTCTAGCACAAAAAGAAAAACGAAATGATACA<br>CCAATCAGTGCAAAAAAAGATATAATGGGAGATAAGACGGTTCGTGTTCGT<br>GCTGACTTGCACCATATCATAAAAATCGAAACAGCAAAGAATGGCGGAAAC<br>GTAAAAGAAGTTATGGAAATAAGACTTAGAAGCAAACTTAAGAGTGTGTTG<br>ATAGTGCAGTATCTTAAAATTTTGTATAATAGGAATTGAAGTTAAATTAGAT<br>GCTAAAAATTTGTAATTAAGAAGGAGTGATTACATGAACAAAAATATAAAA<br>TATTCTCAAAACTTTTTAACGAGTGAAAAAGTACTCAACCAAATAATAAAAC<br>AATTGAATTTAAAAGAAACCGATACCGTTTACGAAATTGGAACAGGTAAAG<br>GGCATTTAACGACGAAACTGGCTAAAATAAGTAAACAGGTAACGTCTATTG<br>AATTAGACAGTCATCTATTCAACTTATCGTCAGAAAAATTAAA<br>ACTGAATACTCGTGTCACTTTAATTCACCAAGATATTCTACAGTTTCAATTCC<br>CTAACAAACAGAGGTATAAAATTGTTGGGAGTATTCCTTACCATTTAAGCAC<br>ACAAATTATTAAAAAAGTGGTTTTTGAAAGCCATGCGTCTGACATCTATCTG<br>ATTGTTGAAGAAGGATTCTACAAGCGTACCTTGGATATTCACCGAACACTAG<br>GGTTGCTCTTGCACACTCAAGTCTCGATTCAGCAATTGCTTAAGCTGCCAGC<br>GGAATGCTTTCATCCTAAACCAAAAGTAAACAGTGTCTTAATAAAACTTACC<br>CGCCATACCACAGATGTTCCAGATAAATATTGGAAGCTATATACGTACTTTG<br>TTTCAAAATGGGTCAATCGAGAATATCGTCAACTGTTTACTAAAAATCAGTT<br>TCATCAAGCAATGAAACACGCCAAAGTAAACAATTTAAGTACCGTTACTTAT<br>GAGCAAGTATTGTCTATTTTTAATAGTTATCTATTATTTAACGGGAGGAAATA<br>ATTCTATGAGTCGCTTTTGTAAATTTGGAAAGTTACACGTTACTAAAGGGAA<br>TGTAGATAAATTATTAGGTATACTACTGACAGCTTCCAAGGAGCTAAAGAGG<br>TCCCTAGACTCTAGACCCGGGGATCTCTGCAGTCGGGAAGATCTGGTAATGA<br>CTCTCTAGCTTGAGGCATCAAATAAAACGAAAGGCTCAGTCGAAAGACTGG<br>GCCTTTCGTTTTATCTGTTGTTTGTCGGTGAACGCTCTCCTGAGTAGGACAAA<br>TCCGCCGCTCTAGCTAAGCAGAAGGCCATCCTGACGGATGGCCTTTTTGCGT<br>TTCTACAAACTCTTGTTAACTCTAGAGCTGCCTGCCGCGTTTCGGTGATGAAG<br>ATCTTCCCGATGATTAATTAATTCAGAACGCTCGGTTGCCGCCGGGCGTTTTT<br>TATGCAGCAATGGCAAGAACGTTGCTCTAGAGCGGCCGCATCGATTCACAGT<br>GGCAATCTCCCCCGTATTCGTTTGAAATGTGCCACATTAACAGCGCCGGGTG<br>ATGTCCGTATCGTTCTGCTAATAAGCGGTTGATGTGCCGTGTTTTTTCTCGGT<br>AGACTTTAGATGTGAGGCAGTGGTTGTGCCTTCCGCCGTGCAGCTGTTTGAC<br>GCGGGAGGCATTGACGCGCAAAACTTCCGGATAGGTTTGCGACAGCCAGGC<br>CGGACGGGCTCCGCTCGGCGTTGCTAATATGACCCGGCCGCCTATACTGTGA<br>ATCCGCTCAAAAATATCATCCAGCCAT |
| SEQ ID NO: 20, primer P1 | 5-TTACCTTCTCTCTTCTAAGTACCGTTCGTATAGCAT-3<br>-lox71-spc-lox66 cassette |
| SEQ ID NO: 21, primer P2 | 5-CAAGCAAAGCTGTTTTATCTACCGTTCGTATAATGT-3<br>-lox71-spc-lox66 cassette |
| SEQ ID NO: 22, primer P3 | 5-TACAAAGCAAAAGCGAAAATGACCATC-3<br>-Upstream homology arm |
| SEQ ID NO: 23, primer P4 | 5-ATGCTATACGAACGGTACTTAGAAGAGAGAAGGTAA-3<br>-Upstream homology arm |
| SEQ ID NO: 24, primer P5 | 5-ACATTATACGAACGGTAGATAAAACAGCTTTGCTTG-3<br>-Downstream homology arm |
| SEQ ID NO: 25, primer P6 | 5-CAGCTGATAGGATTCTTGCTCGCTTA-3<br>-Downstream homology arm |
| SEQ ID NO: 26, primer P7 | 5-TGATAGGTGGTATGTTTTCGCTT-3<br>-Promoter p43 |
| SEQ ID NO: 27 primer P8 | 5-ATAAATACCATGCTTCATGTGTACATTCCTCTCTTA-3<br>-Promoter p43 |
| SEQ ID NO: 28, primer P9 | 5-TAAGAGAGGAATGTACACATGAAACATGGTATATAC-3<br>-Primers DPEase Cc |
| SEQ ID NO: 29, primer P10 | 5-GAATTCTTAGGAGTGTTTATGACATTC-3<br>-Primers DPEase Cc |
| SEQ ID NO: 30, primer P11 | 5-TAGAATGCAAAAAGTGAAATCATAATGATAGGTGGTATGTTTTCGCTTGA-<br>3<br>-P43-DPEase expression cassette |
| SEQ ID NO: 31, primer P12 | 5-CGTCTGTACGTTCCTTAAGGAATTCTTAGGAGTGTTTATGACATTCTAAT-3<br>-P43-DPEase expression cassette |

-continued

| Sequence number | Sequences |
|---|---|
| SEQ ID NO: 32, primer P13 | 5-ATTAGAATGTCATAAACACTCCTAAGAATTCCTTAAGGAACGTACAGACG-3<br>-pUB110 vector backbone (according to P43-DPEase expression cassette) |
| SEQ ID NO: 33, primer P14- | 5-TCAAGCGAAAACATACCACCTATCATTATGATTTCACTTTTTGCATT-3<br>-pUB110 vector backbone (according to P43-DPEase expression cassette) |
| SEQ ID NO: 34, primer P15- | 5-AAATCTAAAATTATCTGAAAAGGGAAGATCTTTCTAAAGAGGAAATGGTG-3<br>-D-alanine racemase gene |
| SEQ ID NO: 35, primer P16 | 5-TTGCTGAACAGATTAATAATAGATTGAATTCTCCATTTAGGTAAGTTAAT-3<br>-D-alanine racemase gene |
| SEQ ID NO: 36, primer P17- | 5-ATTAACTTACCTAAATGGAGAATTCAATCTATTATTAATCTGTTCAGCAA-3<br>-PpuB110 vector backbone (according to D-alanine racemase) |
| SEQ ID NO: 37, primer P18 | 5-CACCATTTCCTCTTTAGAAAGATCTTCCCTTTTCAGATAATTTTAGATTT-3<br>-PpuB110 vector backbone (according to D-alanine racemase) |
| SEQ ID NO: 38 | AGCGGTACCATTATAGGT**AAGAGAGGAATGTACAC**ATGAAACATGGTATATACTACGCATATTGG |
| SEQ ID NO: 39 | AGCGGTACCATTATAGGT**AGAAAGGAGGATTACAT**ATGAAACATGGTATATACTACGCATATTGG |
| SEQ ID NO: 40 | AGCGGTACCATTATAGGT**AGAAAGGAGGATTCGAA**ATGAAACATGGTATATACTACGCATATTGG |

FIGURES

FIG. 1 represents an example of a strategy for the deletion of the alrA structural gene.

FIG. 2 represents the construction of the plasmid pUB-P43-DPEase-alrA also named vector/plasmid pR1.

FIG. 3 represents an outline of the vectors/plasmids pR1/pR2/pR3. The sequence region modified with respect to translational efficiency in pR2/pR3 is outlined as a black box.

FIG. 4 represents a PCR analysis of the beta-galactosidase genomic locus (ganA1/ganA2; wild type product: 2.1Kb). DNA was applied from three independent colonies of BsR, and two collection strain as *B. subtilis* 1A751 and type 168 strain; M1, gene ruler 100 bp; M2, gene ruler 1Kb ladder.

FIG. 5 represents a flow scheme for the cassette EmR-ComK removal using MazF cassette. X indicates on crossing-over event.

FIG. 6 represents a PCR analysis of the EmR-ComK cassette in BsR clones using gan locus specific primers. 1: BsR original strain, 2-5: Em sensitive clones, M: GeneRuler 1 kb ladder.

FIG. 7A represents a PCR analysis of D-alanine auxotrophic yqfD (BsR4) mutant candidate clones using specific yqfD region primers.

FIG. 7B represents a genetic setup of sporulation locus yqfD before and after the deletion and location of analytic primers. 1-5 BsR4. #1-5 (1.7 kb product indicates deletion of yqfD); 6: BsR original strain expected for yqfD wild type); M: GeneRuler 1 kb ladder.

FIGS. 8A-8B represent a phenotype analysis of ΔyqfD (BsR4) on LB+D-alanine supplementation. FIG. 8A represents the BsR4 strain and FIG. 8B represents the BsR strain. For each figure, the left side is before heat treatment, and the right side is after heat treatment.

FIGS. 9A-9B represent the phenotypic screening of BsR5 mutant candidates via loss of D-alanine prototrophy. Clones that have successfully excised the integrated mutagenesis cassette should no longer be able to grow on LB (FIG. 9B) but strictly depend on medium supplemented with D-alanine (FIG. 9A).

FIG. 10 represents a schematic overview of the strain platform filiation and genetic events applied.

FIG. 11 represents an overview of the Working Cell Bank preparation

FIG. 12 represents an overview of the strain cultivation providing the D-psicose 3-epimerase and its stabilization step.

The following Examples are provided in order to demonstrate and further illustrate certain embodiments and aspects of the present invention and are not to be construed as limiting the scope thereof.

EXAMPLES

Example 1: Construction of a Recombinant *Bacillus subtilis* Producing a D-Psicose Epimerase from *Clostridium cellulolyticum* H10

Within a large part of the bacteria, D-alanine is an important component of the glycan subunits to form the cell wall (peptidoglycan).

Alanine is usually found as the L-stereoisomer in nature, making the conversion to D-alanine by the cytoplasmic D-alanine racemase (alrA) essential for cell growth.

Lack of the enzyme leads to rapid cell lysis due to a failure in the initial step of peptidoglycan biosynthesis.

The entire alrA structural gene (GenBank, no. CAB12271.1) and regulatory signals for its expression were contained within the 1.17 kb DNA fragment (SEQ ID NO: 17).

1. Construction of the *Bacillus subtilis* Host Named BsR

Fusion of the antibiotic resistance marker cassette with long-flanking homology regions by PCR was done as described by Shevchuk et al. (Nikolai A. Shevchuk et al. Nucleic Acids Research, 2004(32):e19). In brief, it was carried out as follows.

The lox71-spc-lox66 cassette was amplified from vector p7S6 using P1/P2 primer pair. Two additional primer pairs (P3/P4 and P5/P6) were used to amplify about 900 bp DNA fragments flanking the D-alanine racemase region for deletion at its front and back ends.

Extensions of 32 nucleotides (nt) that were complementary to the 5' and 3'ends of the amplified marker cassette were added to the 5' end of the reverse and forward primers of the front and back flanking regions, respectively. Finally, the two flanking homology regions and the lox71-spc-lox66 cassette were fused by PCR.

The PCR product was directly transformed into the *B. subtilis* host (the PCR product has been recombined with the *B. subtilis* chromosome due to the two flanking homology fragments).

Transformants clones were selected on LB agar enriched with both spectinomycin (Spc) (100 μg/mL) and D-alanine (200 μg/mL).

A positive clone which provides the phenotype [alrA$^-$; Spc$^R$] was selected for further modification.

Then the antibiotic-resistant gene Spc was knocked out by the Cre/Lox system.

Finally, a *Bacillus subtilis* host [alrA$^-$] in which the alanine racemase alrA gene is deleted is obtained (FIG. 1). This *Bacillus subtilis* is named BsR.

2. Construction of the Recombinant Plasmid and the Antibiotic Free *B. subtilis* DPEase Producer The *Bacillus subtilis* endogenous promotor P43 was amplified from the well-known strain *Bacillus subtilis* 168 chromosome using the primer pair P7/P8. The D-psicose 3-epimerase gene of *Clostridium cellulolyticum* $H_{10}$ (ATCC 35319) (GenBank no CP001348.1) (sequence II) encoding the protein with locus tag YP_002505284 was de novo synthetized by with 1) integration of NdeI and XhoI restriction site at 5' and 3'terminus (for further gene cloning steps) and 2) a nucleotide substitution T558C to neutralize a NdeI restriction site (SEQ ID NO: 4).

The P43 promoter and D-psicose 3-epimerase gene were fused as an expression cassette via SOE-PCR (splicing overlap extension PCR) using P7 and P10 primers. Then the PCR-produced p43-DPEase cassette was cloned into pMD-19T vector.

The pUB110 plasmid was used with its original HpaII promotor in order to improve the expression.

The plasmid antibiotic resistance gene-free was constructed referring a method called simple cloning (Chun You et al. Appl. Environ. Microbiol. 2012, 78(5): 1593-1595) which is a sequence-independent method without the need for restriction and ligation enzymes.

The protocol consists of three steps:

(1) Linear DNA (P43-DPEase expression cassette and the appropriate zone of linear pUB110 vector backbone (the fragment outside Mob gene region)) were separately amplified by PCR with primers P11/P12 and P13/P14 respectively (P11/P12 contain the 40-50 bp overlapping termini of P13/P14).

(2) The DNA multimers was generated based on these DNA templates (target gene and corresponding vector) by POE-PCR (prolonged overlap extension PCR) without primers and (3) the POE-PCR products (pUB-P43-DPEase) were transformed into the *Bacillus subtilis* competent cells. Hit transformants were recovered on LB agar by adding 50 μg/mL kanamycin. Using the same method, D-alanine racemase gene was inserted replacing the Kanamycin (Km) and Bleomycin (Blm) antibiotic-resistant genes region.

D-alanine racemase gene and vector backbone were amplified via PCR with the P15/P16 and P17/P18 primers respectively.

The DNA multimers were transformed within *Bacillus subtilis* [alrA$^-$] competent cells, deficient in biosynthesizing D-alanine metabolite.

Finally, the plasmid pUB-P43-DPEase-alrA (SEQ ID NO: 14) (FIG. 2) was selected on LB agar without adding D-alanine.

The main advantage of this strategy is to provide direct selection for the plasmid in complex media without antibiotics.

As the D-alanine racemase involved in the cell wall metabolism, the loss of the activity leads to the cell lysis, preventing the accumulation of a population of cells which have lost the plasmid.

Example 2: Plasmid Optimization for Higher DPEase Expression

The experimental strategy has aimed at revealing the expression potential and intrinsic limitations of *Bacillus subtilis* as DPEase expression host (BsR), as obtained above.

The modifications introduced into the parental plasmid pUB-P43-DPEase-alrA (pR1) target by a translational efficiency (pR2, pR3).

This means for pR2/pR3, if the gene expression is "on" in a given cell at a given time point, more protein should be expected to be delivered at this moment.

1. Plasmid Optimization for the Ribosome Binding Sites (pR2)

As a template for generation of optimized DPEase expression constructs, the plasmid PUB-P43-DPEase-alrA (or pR1) was isolated from overnight cultivation in standard LB medium and the plasmid free strain was kept for further steps.

These plasmid preparations served as templates for PCR mediated insertion of variant ribosome binding sites and adjacent regions (FIG. 3). After successful mutagenesis PCR, the new plasmid was introduced back to the *B. subtilis* alrA deficient plasmid-free strain (BsR).

Successfully transformed clones were cultivated in standard LB medium and pass throughout a primary activity screening phase (Protocol #1).

Then, a plasmid DNA was prepared from overnight cultivations for electrophoresis and sequencing verification of the ribosome binding site zone change.

The upstream sequence identified in the pR2 clone that performs best in conjunction with the downstream DPEase open reading frame is shown below.

Nucleotide sequence of the 5' untranslated region upstream of the DPEase in pR1 (1) and pR2 (2). The ATG codon of the DPEase gene is shown underlined and the RBS modified region is in italic bold in Table 1 below.

TABLE 1

Nucleotide sequences of the 5' untranslated region upstream of the DPEase in pR1 (1) and pR2 (2)

| | |
|---|---|
| pR1 | 1-AGCGGTACCATTATAGGT**AAGAGAGGAATGTACAC**<u>ATG</u> AAACATGGTATATACTACGCATATTGG (SEQ ID NO: 38) |
| pR2 | 2-AGCGGTACCATTATAGGT**AGAAAGGAGGATTACAT**<u>ATG</u> AAACATGGTATATACTACGCATATTGG (SEQ ID NO: 39) |

Plasmid pR2 of SEQ ID NO: 15 contains an optimized sequence of SEQ ID NO: 1 or SEQ ID NO: 39.

Protocol #1: Enzymatic Detection of DPEase Activity

The analysis of DPEase screening samples was performed by applying a Fructose/Glucose Assay Kit from Megazymes (K-FRUGL).

Initial evaluation revealed that psicose does not give rise to any signal, thus, DPEase activities can be measured by following the reduction of fructose contents in the reactions. Briefly, samples were diluted 1:1000 freshly prior to the reaction.

Calibration glucose/fructose standards as well as a fructose/PBS mix were always included. Sugars could be detected in a linear range of 0-100 mg/L.

100 μL sample were transferred to an assay-plate (96 well MTP, flat-bottom).

90 μL reaction mix 1+2 (10 μL each of Solution 1&2, +70 μL milliQ (mQ) water) was added and allowed to incubate at RT for a few minutes.

20 μL reaction mix 3 (2 μL Solution 3+18 μL mQ water) was added and after 5 min the OD340 was read out as "blank" 20 μL reaction mix 4 (2 μL Solution 4+18 μL mQ water) was added and after 5 min the OD340 was read out as residual fructose.

The residual fructose was calculated with the help of the calibration standards, and the converted psicose estimated in comparison to the untreated fructose sample.

2. Establishment of Vector with Customized Translation Initiation (pR3)

The previous pR2 variant depicted in FIG. 3 served as parental plasmid for further optimization of the translation initiation region (spacer).

To this end, the proximal 4 nucleotides upstream of the DPEase open reading frame were randomized via PCR mutagenesis.

The resulting plasmids variants were introduced back to the *B. subtilis* alrA deficient plasmid-free strain (BsR) and cultivated onto standard LB agar plates.

In order to cover all possible 4 nucleotide combinations, a mutant bank of above 2000 clones was randomly picked and cultivated in 96-Deep well plates (DWP and assessed for DPEase expression in the primary activity screening phase (Protocol #1).

The best clone harboring the pR3 plasmid has been sequenced. (below)

Nucleotide sequences of the 5' untranslated region upstream of the DPEase in pR1 (1) and pR2 (2) and pR3 (3) are shown in Table 2 below. The ATG codon of the DPEase gene is shown underlined and the RBS modified region is in italic bold and the translation initiation region boxed.

TABLE 2

Nucleotide sequences of the 5′ untranslated region upstream of the DPEase in pR1 (1) and pR2 (2)

| | |
|---|---|
| pR1 | 1-AGCGGTACCATTATAGGT**AAGAGAGGAATGTACAC**ATGAAACAT GGTATATACTACGCATATTGG (SEQ ID NO: 38) |
| pR2 | 2-AGCGGTACCATTATAGGT**AGAAAGGAGGATTACAT**ATGAAACATG GTATATACTACGCATATTGG (SEQ ID NO: 39) |
| pR3 | 3-AGCGGTACCATTATAGGT**AGAAAGGAGGATT**CGAAATGAAACATG GTATATACTACGCATATTGG (SEQ ID NO: 40) |

Plasmid pR3 of SEQ ID NO: 16 contains an optimized sequence of SEQ ID NO: 2 or SEQ ID NO: 40.

3. Expression Screening and Enzyme Assay

A second activity screening phase has been done for more representative DPEase production. For the re-assessment, a selection of best performing clones was chosen for cultivation with larger volume.

Thus, the strain BsR strain previously transformed with pR1 and pR2 and pR3 plasmids were cultivated in shake flasks (Table 3).

Samples were taken at final point (16 h) and cells were collected by centrifugation at 6000 g for 15 minutes and the supernatant was discarded.

The cells pellets harboring *C. cellulolyticum* DPEase prepared by freeze-drying were vacuum freeze-dried, grinded and directly used as an enzyme powder.

Next, DPEase activity for each enzyme powders produced was done (following the method given below).

TABLE 3

Media composition used for the DPEase production from plating to production cultivations in shakeflasks at 37° C. at 200 rpm.

| Media comp.(g/L) | Plate | $1^{st}$ Seed culture | $2^{nd}$ Seed culture | Production |
|---|---|---|---|---|
| Trypton from milk casein (Biokar) | 10 | 10 | 10 | |
| Yeast Extract (BactoYE Difco, BD) | 5 | 5 | 5 | 15 |
| NaCl [7647-14-5] | 10 | 10 | 10 | 8 |
| Dextrose (Roquette Freres) | | | | 15 |
| $Na_2HPO_4$, $12H_2O$ [10039-32-4] | | | | 1 |
| $MgSO_4$, $7H_2O$ [10034-99-8] | | | | 1 |
| $MnSO_4$, $H_2O$ [10034-96-5] | | | | 0.008 |
| Antifoam (EROL18) | | | | 0.3 |
| pH adjustment (NaOH 4M) 7.4* | | no | no | no |

*pH is adjusted before heat sterilization. The effective cultivation initial pH is roughly 6.75

Incubation time were overnight for the plate, 16 h for the first seed culture, up to $Abs_{600nm}$ for second seed culture and 16 h for the production.

Method: DPEase Enzyme Assay Description

The DPEase activity was measured via determining the quantity of D-psicose produced using a whole-cell reaction.

One milliliter of the reaction mixture contained D-fructose (80 g/L) in 50 mM Tris-HCl, pH7.5, and 200 μL of enzyme solution; the cells were dissolved in tris-HCL.

The reaction was incubated at 60° C. for exactly 10 minutes and ended by boiling at 100° C. for exactly 10 minutes. The generated D-psicose in the mixture was detected via a Waters Alliance HPLC, fitted with aminex HPX-87$Ca^{2+}$ column (from Biorad) with dimensions 250×4 mm, #125-0094 and a refractive index detector (waters 410).

The column was eluted with pure water at a flow rate of 0.3 ml/min at 85° C. One unit of DPEase activity was defined as the amount of enzyme that catalyzed the production of 1 μmol of D-psicose per minute.

4. DPEase Performance Results

The best DPEase enzyme performances are gathered into the following Table 4:

TABLE 4

Results of strain BsR transformed with the plasmid pR1, pR2 or pR3

| | DPEase enzyme act. (U/mL) | n |
|---|---|---|
| BsR-pR1 | 10.57 | 5 |
| BsR-pR2 | 26.85 | 10 |
| BsR-pR3 | 38.85 | 20 |

n means the number of assays performed.

Initial strain (BsR), which is D-alanine racemase deficient, harboring the constructed PUB-P43-DPEase-alrA vector (pR1) showed a DPEase enzyme activity of about 10.57.

The two steps plasmid optimizations showed higher DPEase activity with about 26.85 U/mL and 38.85 U/mL for RBS region change (pR2) and translation initiation spacer optimization (pR3), respectively. Plasmid pR3 is the most promising plasmid.

Example 3: *Bacillus subtilis* BsR Improvement for DPEase Enzyme Expression Enhancement In parallel to the plasmid optimization, the strain itself, BsR, was optimized, especially for the regulatory and safety purposes.

Antibiotics sensitivity of the BsR showed the strain was able to grow when erythromycin was added at 5 μg/mL. This observation clearly indicates that the strain was erythromycin resistant ($Em^R$). This resistance has to be removed. *Bacillus* genus bacteria are known to produce a dedicated, very resistant and non-reproductive structure to enter in a state of dormancy: the endospores.

Bacterial endospores keeps all material the cell needs to recover a living cell when favorable conditions will appear.

The endospores are the perfect dissemination factor for the strain and is a serious risk for environmental and health contamination. For industrial uses of an endospore forming BsR, it is important to abort the endospore forming pathway.

1. Removal of the EmR-comK Cassette: Generation of BsR3

Aiming to develop an enzyme producer strain by molecular biology tools, the *Bacillus subtilis* BsR was tested for the applicability of different antibiotics (tetracycline, erythromycin and kanamycin) and sugars (xylose and mannitol) likely used as inducers of gene expression on some plasmids.

Surprisingly, BsR was able to cultivate on erythromycin even at a concentration that is applied for high copy plasmids (5 μg/mL) selection pressure and the strain showed a clear delayed cultivation on xylose, compare to *Bacillus subtilis* (wild-type).

As the *B. subtilis* beta-galactosidase gene lacA (also named ganA) can serve as integration site for heterologous expression cassettes and/or as a reporter gene to test promotor induction efficiencies, its functionality was tested on X-gal agar plate.

X-gal(5-bromo-4-chloro-3-indolyl-beta-D-galactopyranoside($C_{14}H_{15}BrClNO_6$)) which is an analog of lactose sensitives to beta-galactosidase (the enzyme cleaves the beta-glycosidic bond in D-lactose) is cleaved and galactose and 5-bromo-4-chloro-3-hydroxyindole are released.

The latter spontaneously dimerizes and is oxidized into 5,5'-dibromo-4,4'-dichloro-indigo (insoluble blue color).

Indeed, native lacA gene by growing the cells on agar containing the chromogenic substrate X-gal should have blue colored colonies, indicating the lacA gene is active. For BsR strain, no blue colonies were seen onto X-gal plate.

Thus, lacA PCR analysis was done compared to a *B. subtilis* strains (wild-type).

If wild type lacA gene is present, a 2.1 kb product should be provided. PCR analysis clearly showed a larger amplification band of about 5 kb indicating the lacA locus contained an insert in (FIG. 4).

This amplified fragment was amplified and blasted to reveal the existence of a cassette containing the EmR gene and a comK gene controlled by the xylose-inducible promoter PxylA.

To remove the EmR-comK cassette (PCR fragment of 6.2 kb), an *Escherichia coli* toxin gene MazF as a counter-selectable marker was used.

The MazF gene was placed under the control of an isopropyl-β-d-thiogalactopyranoside (IPTG)-inducible expression system and associated with the alrA gene to form the MazF cassette, which was flanked by three targeting sequences.

A double-crossover event between delivery vector and the chromosome integrated the MazF cassette in front of the targeted EmR-comK cassette, and yielded an IPTG-sensitive strain with D-alanine racemase. Another single-crossover event between the two ganA sequences led to the excision of the MazF cassette (FIG. 5).

Then clones were evaluated regarding the desired phenotypes of successful mutants a) no growth with erythromycin selection and b) no growth on medium lacking D-alanine.

The latter clones were successfully checked via PCR analysis for the desired EmR-comK cassette removal genotype with a 2.3 kB amplified fragment (FIG. 6).

Theses erythromycin sensitive ($Em^S$) and D-alanine auxotrophic clones were subsequently transformed with the DPEase expression plasmid pR3.

The resulting clones were able to growth on LB with no external D-alanine supplementation.

2. Spore Inactivation: Generation of BsR4 and BsR5

Previously to generate the BsR5 strain version which is erythromycin sensitive and sporulation deficient (double mutant $Em^S$ $Spo^-$), the impact of the endospore inactivation was evaluated with the strain BsR (containing EmR-comK cassette) leading to the single mutant named BsR4, $Em^R$ $spo^-$ genotyped.

The strategy to disrupt the sporulation metabolic cascade was to delete the yqfD essential gene, which acts during the stage IV (one of the later phase on sporulation process) of the endospore maturation, in order to abort the sporulation.

a—Generation of the Single Mutant Strain, BsR4

Establishment of a D-alanine racemase selectable mutagenesis cassette for deletion of the sporulation gene yqfD was generated and introduced into BsR devoid of the DPEase harbored plasmid.

The alrA cassette was done as the one used for the EmR-ComK cassette removal, with specific sequence for ydfD gene deletion.

Transformants were successfully selected by their capability to grow on medium with no D-alanine in.

These candidates were applied for IPTG induced counter selection that leads to clones devoid of the mutagenesis cassette as well as the yqfD sporulation gene (ΔyqfD).

The single mutants were identified by their D-alanine auxotrophy and by PCR analysis of the yqfD locus (FIG. 7A).

In order to evaluate the sporulation phenotype of BsR4 strain, the mutant clones were cultivated in LB+D-alanine medium for overnight growth.

Cultures were then spotted on sporulation agar plates (supplemented with D-alanine) to form large colonies.

The sporulation plates were incubated at 37° C. for 3 days and evaluated by microscopy. The BsR original strain had produced phase-bright spores, while the ΔyqfD mutant clones did not produce any phase bright spores indicating the sporulation defect (spores produced by mutants were dark instead of bright which indicates that they are unable to proceed to maturation).

To check that the mutant clones were not able to produce any mature (so viable) endospores, an overnight cultivation in LB+D-alanine was performed at 37° C.

The day after, 2×0.5 mL were sterile sampled into sterile tubes.

The first tube was directly spotted on a LB+D-alanine medium when the second was incubated at 80° C. for 30 minutes.

Heat treatment aims to kill vegetative cells, and only mature endospores can survive.

After the heat treatment, the broth was spotted onto the previous described plate (directly next to the previous unheattreated spots).

The plate was then incubated overnight at 37° C. for growth. As expected, only BsR wild type clone survived the heat treatment.

Only cellular debris was visible for the spots after heat treatment for BsR4 clone (FIG. 8A).

b—Generation of the Double Mutant Strain BsR5

The mutagenesis cassette targeting the sporulation locus yqfD that has already been successfully applied to generate the single mutant strain, BsR4, was introduced into the erythromycin sensitive strain, BsR3.

After successful genomic integration, mutant screening was initiated for the identification of clones that had excised the mutagenesis cassette from the genome, leading to clean deletion of yqfD gene.

As performed for BsR4 strain, the clones were selected for their inability to produce mature endospores. After an overnight cultivation, samples were spotted before and after the heat treatment onto LB+D-alanine plates then incubated for another night at 37° C.

The hit candidates that did not grow after heat treatment were picked and spotted to LB medium plate for their loss of D-alanine prototrophy and incubate overnight at 37° C.

The hits candidates were those which showed growth (FIG. 9A).

Finally, an industrial strain platform, BsR5, was obtained as a double mutant erythromycin sensitive and sporulation negative for respect environmental and safety regulations (FIG. 10)

3. DPEase Enzyme Production Performance Results

All the strains obtained (BsR3, BsR4 and BsR5) were transformed with hit plasmid pR3. They were cultivated regarding the following protocol (FIGS. 11 and 12):

Working Cell Bank Construction:

Working cell bank refers to a −80° C. frozen stock, in Nalgene® vials of 2 mL.

The process contains a petri dish cultivation on LB medium (trypton 10 g/L, Yeast extract 5 g/L, NaCl 5 g/L, pH 7.5 adjusted with 10N soda) at 37° C. for 16 h. A cellular suspension is prepared within a 5 or 10 mL of liquid LB+0.1 mM manganese ($MnCl_2$, $4H_2O$ [13446-34-9]) medium to obtain a≈10 O.D.$_{600nm}$ preparation. A 500 mL shake flask with 2 lateral baffles containing 50 mL liquid LB+0.1 mM manganese is sterilized at 121° C. for 21 minutes. The latter medium is inoculated to 0.1 O.D.$_{600nm}$ with the freshly interim suspension. The cultivation is incubated at 37° C. and 250 rpm (orbital=5 cm) and the growth is monitored with hourly O.D.$_{600nm}$ measurements. The procedure move one step ahead when the cultivation reaches O.D.$_{600nm}$ MAX/2. Then, the exact volume of the final culture is measured and the same volume of cryoprotectant (30% v/v) Glycerol [56-81-5]) is slowly added and mixed until good homogenization. The latter suspension is then aliquoted at 1.8 mL into 2 mL vials. The vials freshly filled up are rapidly stored into a −80° C. freezer and designed as a Working Cell Bank for further uses.

Strain Cultivation for DPEase Enzyme Production

As a seed culture, a 300 mL shake flask unbaffled was filled up with 30 mL LB medium supplemented with manganese and then heat sterilized at 121° C. for 20 minutes. 1.8 mL of a working cell bank tube was used for inoculation. The cultivation was incubated 4 h at 37° C. and 250 rpm (orbital=5 cm).

As a production cultivation, a 0.9 mL of the previous seed culture was used to inoculate a sterile 300 mL shake flask with 3 lateral baffles and 50 mL modified LB-ROQ medium (Dextrose monohydrate 15 g/L, Yeast extract 15/L, NaCl [7647-14-5] 8 g/L, $K_2HPO_4$ [7758-11-4] 7 g/L, $KH_2PO_4$ [7778-77-0] 1.3 g/L, $MgSO_4{\cdot}7H_2O$ [10034-99-8] 50 mg/L, $MnSO_4{\cdot}H_2O$ [10034-96-5] 0.4 mg/L and $MnCl_2{\cdot}4H_2O$ [13446-34-9] 19 mg/L. pH should be close to neutral. The culture was incubated at 37° C. and 250 rpm (orbital 5 cm) for 16 h. The DPEase enzyme assessment was done as detailed into example 2.

The best DPEase enzyme performances are gathered into the Table 5 below indicating the average value of the performance and the number of trials performed:

TABLE 5

Results of the strain BsR3 transformed with the plasmid pR3, the strain BsR4 transformed with the plasmid pR3 or the strain BsR5 transformed with the plasmid pR3 n means the number of assays performed.

| | Average value DPEase enzyme act. (U/mL) | n |
|---|---|---|
| BsR3-pR3 | 39.25 | 2 |
| BsR4-pR3 | 44.31 | 2 |
| BsR5-pR3 | 52.06 | 11 |

The successive DPEase enzyme productions with the different constructed strain platforms, BsR3 (single mutant $Em^S$), BsR4 (single mutant ΔyqfD)) and BsR5 (double mutant $Em^S$, ΔyqfD) when transformed with the plasmid pR3 (puB-P43-DPEase-alrA vector) leaded to progressively improved the performance.

Intermediate single mutation strains (BsR3 and BsR4) were assessed for the DPEase production to follow the impact of the genetic modifications. For these two strains, the performance was not affected.

The final strain, BsR5 transformed with the plasmid pR3, which is environmentally and safety optimized, leads to the better expression of the enzyme DPEase.

The strain might save resources expressing DPEase instead of produces erythromycin resistance tools and endospore full maturation processing machinery.

Example 4: Optimization of the Fermentation Medium for DPEase Enzyme Expression Enhancement

Material & Methods

The strain used in the strain BsR5 transformed with the plasmid pR3.

1.1 Production of Biomass

The production of biomass begins with a preculture step. Glucose (15 g/L), yeast extract (15 g/L) and NaCl (15 g/L) are dissolved in demineralized water (QS 1L). pH is not adjusted. The medium is placed in a baffled Erlenmeyer (2000 mL), then the erlenmeyers are autoclaved 20 minutes at 121° C., then inoculated in sterile conditions with 1 cryotube, then incubated at 37° C., during 4 hours, at 110 RPM.

The precultures are carried out in 2L erlenmeyers containing 0.5 L of medium. The erlenmeyers are incubated for 3 h at 37° C. and 110 RPM so as to obtain an optical density of between 0.5 and 1 or a DCW (dry cell weight) of between 0.07 and 0.18 g/L.

The production step consists of a "batch" type fermentation which is carried out with a complex medium based on glucose, yeast extract and salts. The management of the pO2 is special since the medium is micro-aerated: the OUR (oxygen consumption) is maintained around 7 mmol/l/h. To do this, the agitation and the aeration are weak and fixed (200 RPM and 9 L/min), which causes a zero pO2 during the ¾ of the production. During the fermentation, there is no addition of medium (fed). A regulation of pH 6 is set up with ammonia 20% (w/w).

1.2 Biomass Preparation-Grinding

Biomass is collected when glucose is completely consumed. At this point the enzymatic activity is maximal. The biomass is then centrifuged (10000 g/5 min) and washed with a 50 mM PBS buffer pH8. The cells are then broken in a ball mill (30 min/2 g beads/1 g washed must). The mixture obtained is filtered through a 0.45 μm filter in order to remove the debris. The solution obtained is stable for 7 days at 4° C.

1.3 Measurement of Activity

Enzymatic analysis is carried out under the following conditions: 800 μl of substrate (fructose 400 g/L in 50 mM PBS pH 8) are preincubated at 55° C. for 5 minutes. The necessary amount of enzymatic solution is added to start the reaction. The whole is incubated for 10 min at 55°. The reaction is then stopped by a passage during 10 minutes at 100° C. The measurement of the psicose produced is carried out by HPLC (Ca2+column at 65° C., H2O at 0.3 ml/min and refractometric detection) by measurement of the % area of psicose. The activity is expressed in μmol of psicose formed per ml of enzyme and per minute of reaction (U/ml).

Several fermentation medium were tested, and their compositions are detailed in Table 6 below.

TABLE 6

Fermentation medium tested

| Reference | Glucose (g/L) | Yeast (g/L) | $(NH_4)_2SO_4$ (g/L) | $KH_2PO_4$ (g/L) | $MgSO_4$ (g/L) | $MnSO_4$ (mg/L) | OUR maximal (mmol/h/L) | Time until complete glucose consumption (h) | Oxygen partial pressure ($PO_2$) | DPEase activity (U/mL) |
|---|---|---|---|---|---|---|---|---|---|---|
| F2 160808 | 15 | 15 | 1 | 1 | 1 | 8 | 8 | 8 | No regulation | 34.0 |
| F1 160811 | 15 | 15 | 1 | 1 | 1 | 8 | 8 | 9 | No regulation | 40.0 |
| F2 160811 | 15 | 15 | 1 | 1 | 1 | 8 | 8 | 9 | No regulation | 41.9 |
| F1 160817 | 30 | 30 | 2 | 2 | 2 | 16 | 7 | 16 | No regulation | 41.8 |
| F2 160817 | 30 | 15 | 1 | 1 | 1 | 8 | 7 | 16 | No regulation | 58.8 |
| F1 160823 | 15 | 15 | 1 | 1 | 1 | 8 | 3 | 16 | No regulation | 28.2 |
| F2 160823 | 15 | 15 | 1 | 1 | 1 | 8 | 3 | 13 | No regulation | 14.2 |
| F1 160906 | 45 | 15 | 1 | 1 | 1 | 8 | 8 | 23 | No regulation | 91.9 |
| F2 160906 | 30 | 15 | 1 | 1 | 1 | 8 | 8 | 17 | No regulation | 71.8 |
| F1 160919 | Fed | 15 | 1 | 1 | 1 | 8 | 8 | 23 | No regulation | 121.2 |
| F2 160919 | 60 | 15 | 1 | 1 | 1 | 8 | 8 | 28 | No regulation | 139.9 |
| F1 160926 | Fed | 15 | 1 | 1 | 1 | 8 | 8 | 27 | No regulation | 143.4 |
| F2 160926 | 45 | 15 | 1 | 1 | 1 | 8 | 8 | 22 | No regulation | 128.0 |
| F1 161003 | 45 | 15 | 1 |  | 1 | 8 | 8 | 20 | No regulation | 127.7 |
| F2 161005 | 45 | 15 | 1 | 1 | 1 | 8 | 8 | 21 | No regulation | 134.1 |
| F1 161011 | 45 | 15 | 1 | 1 | 1 | 8 | 9 | 21 | No regulation | 133.8 |
| F2 161011 | 100 | 15 | 1 | 1 | 1 | 8 | 8 | 71 | No regulation | 156.6 |
| F1 161026 | 60 | 15 | 1 | 1 | 1 | 8 | 80 | 15 | Regulated 5% | 71.7 |

TABLE 6-continued

| Fermentation medium tested | | | | | | | | | | |
|---|---|---|---|---|---|---|---|---|---|---|
| Reference | Glucose (g/L) | Yeast (g/L) | $(NH_4)_2SO_4$ (g/L) | $KH_2PO_4$ (g/L) | $MgSO_4$ (g/L) | $MnSO_4$ (mg/L) | OUR maximal (mmol/h/L) | Time until complete glucose consumption (h) | Oxygen partial pressure ($PO_2$) | DPEase activity (U/mL) |
| F2 161026 | 60 | 15 | 1 | 1 | 1 | 8 | 20 | 17 | No regulation | 134.7 |
| F1 161107 | Fed | 15 | 1 | 1 | 1 | 8 | 8 | 32 | No regulation | 143.0 |
| F2 161107 | 60 | 15 | 1 | 1 | 1 | 8 | 7 | 32 | No regulation | 133.5 |
| F1 161122 | Fed | 15 | 1 | 1 | 1 | 8 | 25 | 29 | No regulation | 166.7 |
| F2 161122 | 60 | 15 | 1 | 1 | 1 | 8 | 3 | 60 | No regulation | 129.3 |
| F2 170117 | Fed | 15 | 1 | 1 | 1 | 8 | 15 | 35 | No regulation | 125.6 |
| F1 170124 | Fed | 15 | 1 | 1 | 1 | 8 | 60 | 24 | Regulated 5% | 41.2 |

Thus, a fermentation medium comprising 60 g/L (medium called "F2 160919") leads to a DPEase activity of about 139.9 U/mL whereas a fermentation medium comprising 15 g/L (medium called "F1 160811") leads to a DPEase activity of about 40.0 U/mL.

These results prove the interest of using a fermentation medium comprising at least 60 g/L of sugar, notably glucose.

Example 5: Comparison of Several Mutated Nucleotide Sequences of 5'UTR

Mutations have been brought in the nucleotide sequences of the 5' untranslated region upstream of the ATG codon of the DPEase gene.

Results of the DPEase activity, tested according to the Standard Of Procedure (SOP), is detailed in Table 7 below.

TABLE 7

| DPEase activity of several variants | | | | |
|---|---|---|---|---|
| clone # | nt upstream of start codon | U/ml | U/ml | U/ml |
| original | AGAGAGGAATGTACAC (SEQ ID NO: 41) | 13.92 | 13.92 | 12.49 |
| I7 | GAAAGGAGGATTCGAA (SEQ ID NO: 42) | 58.44 | 58.44 | 62.87 |
| I9 | GAAAGGAGGATTATGG (SEQ ID NO: 43) | 77.4 | 77.4 | 81.51 |

TABLE 7-continued

| DPEase activity of several variants | | | | |
|---|---|---|---|---|
| clone # | nt upstream of start codon | U/ml | U/ml | U/ml |
| II1 | GAAAGGAGGATTGTCG (SEQ ID NO: 44) | 21.81 | 21.81 | 22.29 |
| II2 | GAAAGGAGGATTTAGT (SEQ ID NO: 45) | 55.72 | 55.72 | 57.39 |
| II3 | GAAAGGAGGATTGAGG (SEQ ID NO: 46) | 55.91 | 55.91 | 55.67 |
| II6 | AGAAAGGAGGATTAAA (SEQ ID NO: 47) | 73.25 | 73.25 | 75.43 |
| II7 | GAAAGGAGGATTTCGT (SEQ ID NO: 48) | 75.45 | 75.45 | 80.24 |
| II8 | GAAAGGAGGATTTTTG (SEQ ID NO: 49) | 49.79 | 49.79 | 51.95 |

Clones II6 and II7 provides the best DPEase activity after analysis according to SOP. However, assays under optimal fermentation conditions (see example 4) showed that mutations of the I7 clone lead to the best DPEase activity.

Thus, mutations of the I7 clone are the mutations present in the plasmid pR3.

The invention claimed is:

1. An isolated nucleic acid molecule comprising (i) a nucleic acid sequence coding for D-psicose 3-epimerase and (ii) the sequence comprising or consisting of SEQ ID NO: 1 or of SEQ ID NO: 2.

2. The isolated nucleic acid molecule according to claim 1, wherein the nucleic acid sequence coding for D-psicose 3-epimerase is selected from the group consisting of the nucleic acid sequence of SEQ ID NO: 3, the nucleic acid sequence of SEQ ID NO: 4, and the nucleic acid sequence encoding for SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13.

3. A recombinant expression vector comprising the isolated nucleic acid molecule according to claim 1, comprising or consisting of SEQ ID NO: 14, SEQ ID NO: 15 or SEQ ID NO: 16.

4. A recombinant host cell comprising the recombinant expression vector according to claim 3.

* * * * *